US009458127B2

(12) United States Patent
Toscano et al.

(10) Patent No.: US 9,458,127 B2
(45) Date of Patent: Oct. 4, 2016

(54) BIS-ACYLATED HYDROXYLAMINE DERIVATIVES

(71) Applicants: Cardioxyl Pharmaceuticals, Inc., Chapel Hill, NC (US); The Johns Hopkins University, Baltimore, MD (US)

(72) Inventors: John P. Toscano, Glen Arm, MD (US); Art Sutton, Baltimore, MD (US); Vincent J. Kalish, Annapolis, MD (US); Frederick Arthur Brookfield, Abingdon (GB); Stephen Martin Courtney, Abingdon (GB); Lisa Marie Frost, Abingdon (GB)

(73) Assignees: Cardioxyl Pharmaceuticals, Inc., Chapel Hill, NC (US); The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/667,622

(22) Filed: Mar. 24, 2015

(65) Prior Publication Data
US 2015/0197502 A1 Jul. 16, 2015

Related U.S. Application Data

(62) Division of application No. 12/962,544, filed on Dec. 7, 2010, now Pat. No. 9,018,411.

(60) Provisional application No. 61/291,224, filed on Dec. 30, 2009, provisional application No. 61/267,399, filed on Dec. 7, 2009.

(51) Int. Cl.
| | | |
|---|---|---|
| *C07C 233/01* | (2006.01) | |
| *C07C 271/08* | (2006.01) | |
| *C07C 317/28* | (2006.01) | |
| *C07D 333/34* | (2006.01) | |
| *C07C 259/06* | (2006.01) | |
| *C07C 259/10* | (2006.01) | |
| *C07C 311/51* | (2006.01) | |
| *C07C 311/53* | (2006.01) | |
| *C07C 317/14* | (2006.01) | |
| *C07D 207/16* | (2006.01) | |
| *C07D 213/40* | (2006.01) | |
| *C07D 213/71* | (2006.01) | |
| *C07D 295/205* | (2006.01) | |
| *C07D 307/82* | (2006.01) | |
| *C07D 309/12* | (2006.01) | |
| *C07C 233/64* | (2006.01) | |
| *C07C 317/32* | (2006.01) | |
| *C07D 295/215* | (2006.01) | |

(52) U.S. Cl.
CPC ........... *C07D 333/34* (2013.01); *C07C 233/01* (2013.01); *C07C 233/64* (2013.01); *C07C 259/06* (2013.01); *C07C 259/10* (2013.01); *C07C 271/08* (2013.01); *C07C 311/51* (2013.01); *C07C 311/53* (2013.01); *C07C 317/14* (2013.01); *C07C 317/28* (2013.01); *C07C 317/32* (2013.01); *C07D 207/16* (2013.01); *C07D 213/40* (2013.01); *C07D 213/71* (2013.01); *C07D 295/205* (2013.01); *C07D 295/215* (2013.01); *C07D 307/82* (2013.01); *C07D 309/12* (2013.01); *C07C 2101/08* (2013.01); *C07C 2101/14* (2013.01)

(58) Field of Classification Search
CPC . C07C 317/14; C07C 317/28; C07C 317/32; C07C 233/01; C07C 233/64; C07C 311/51; C07C 311/53; C07C 271/08; C07C 259/06; C07C 259/10; C07C 2101/08; C07C 2101/14; C07D 233/34; C07D 295/205; C07D 295/215; C07D 213/40; C07D 213/71; C07D 207/16; C07D 309/12; C07D 307/82
See application file for complete search history.

(56) References Cited

U.S. PATENT DOCUMENTS

| | | | |
|---|---|---|---|
| 3,215,687 | A | 11/1965 | Tsuchiya et al. |
| 3,219,428 | A | 11/1965 | Weil et al. |
| 3,382,243 | A | 5/1968 | Bell et al. |
| 3,458,570 | A | 7/1969 | Baker et al. |
| 3,498,967 | A | 3/1970 | De Montmollin et al. |
| 3,661,944 | A | 5/1972 | Dowalo et al. |
| 3,746,727 | A | 7/1973 | Pilgram et al. |

(Continued)

FOREIGN PATENT DOCUMENTS

| | | |
|---|---|---|
| DE | 1 768 511 | 10/1971 |
| EP | 0468690 | 1/1992 |

(Continued)

OTHER PUBLICATIONS

Nagasawa et al, J. Med. Chem., 1995, 38(11), 1872-1876.*
Achmatowicz, M. et al., "Structure-driven design and synthesis of chiral dioxocyclam derivatives", In Tetrahedron, vol. 61, No. 38, Sep. 2005, pp. 9031-9041.
Adams, K.F. et al., "HFSA guidelines for management of patients with heart failure caused by left ventricular systolic dysfunction—pharmacological approaches", In Journal of Cardiac Failure, vol. 5, No. 4, Dec. 1999, pp. 357-382.

(Continued)

*Primary Examiner* — Shailendra Kumar
(74) *Attorney, Agent, or Firm* — Byrne Poh LLP; Nina R. Horan

(57) ABSTRACT

The invention provides certain bis-acylated hydroxylamine derivative compounds, pharmaceutical compositions and kits comprising such compounds, and methods of using such compounds or pharmaceutical compositions. In particular, the invention provides methods of using such compounds or pharmaceutical compositions for treating, preventing, or delaying the onset and/or develop of a disease or condition. In some embodiments, the disease or condition is selected from cardiovascular diseases, ischemia, reperfusion injury, cancerous disease, pulmonary hypertension and conditions responsive to nitroxyl therapy.

31 Claims, 3 Drawing Sheets

(56) References Cited

U.S. PATENT DOCUMENTS

| | | | |
|---|---|---|---|
| 3,948,967 | A | 4/1976 | Krenzer et al. |
| 4,369,174 | A | 1/1983 | Nagai et al. |
| 4,405,357 | A | 9/1983 | Chang |
| 4,409,367 | A | 10/1983 | Beijleveld et al. |
| 4,539,321 | A | 9/1985 | Campbell |
| 4,663,351 | A | 5/1987 | Diamond |
| 4,798,824 | A | 1/1989 | Belzer et al. |
| 4,842,866 | A | 6/1989 | Horder et al. |
| 4,954,526 | A | 9/1990 | Keefer |
| 5,039,705 | A | 8/1991 | Keefer et al. |
| 5,212,204 | A | 5/1993 | Keefer et al. |
| 5,217,720 | A | 6/1993 | Sekigawa et al. |
| 5,278,192 | A | 1/1994 | Fung et al. |
| 5,532,256 | A | 7/1996 | Malamas et al. |
| 5,674,894 | A | 10/1997 | Currie et al. |
| 5,789,447 | A | 8/1998 | Wink, Jr. et al. |
| 5,814,656 | A | 9/1998 | Saavedra et al. |
| 5,977,146 | A | 11/1999 | Muller et al. |
| 6,083,515 | A | 7/2000 | Garvey et al. |
| 6,143,734 | A | 11/2000 | Garvey et al. |
| 6,184,238 | B1 | 2/2001 | Takano |
| RE37,116 | E | 3/2001 | Garvey et al. |
| 6,297,260 | B1 | 10/2001 | Bandarage et al. |
| 6,323,234 | B1 | 11/2001 | Garvey et al. |
| 6,420,409 | B1 | 7/2002 | Yamasaki et al. |
| 6,569,457 | B2 | 5/2003 | Ullah et al. |
| 6,638,534 | B1 | 10/2003 | Ishibashi et al. |
| 6,936,639 | B2 | 8/2005 | Wink et al. |
| 7,109,205 | B2 | 9/2006 | Riechers et al. |
| 7,368,469 | B2 | 5/2008 | Scholkens et al. |
| 7,863,262 | B2 | 1/2011 | Wink et al. |
| 8,268,890 | B2 | 9/2012 | Wink et al. |
| 8,674,132 | B2 | 3/2014 | Toscano et al. |
| RE45,314 | E | 12/2014 | Toscano et al. |
| 9,018,411 | B2 | 4/2015 | Toscano et al. |
| 9,115,064 | B2 | 8/2015 | Toscano et al. |
| 9,221,780 | B2 | 12/2015 | Toscano et al. |
| 2001/0053795 | A1 | 12/2001 | Bond |
| 2002/0010146 | A1 | 1/2002 | Garvey et al. |
| 2002/0016322 | A1 | 2/2002 | Bandarage et al. |
| 2002/0119977 | A1 | 8/2002 | Kanapure et al. |
| 2004/0038947 | A1 | 2/2004 | Wink et al. |
| 2004/0039063 | A1 | 2/2004 | Wink et al. |
| 2004/0077691 | A1 | 4/2004 | Wang et al. |
| 2005/0192254 | A1 | 9/2005 | Wink et al. |
| 2006/0014960 | A1 | 1/2006 | Beckmann et al. |
| 2007/0088043 | A1 | 4/2007 | Srinivas et al. |
| 2007/0299107 | A1 | 12/2007 | Toscano et al. |
| 2009/0163487 | A1 | 6/2009 | Toscano et al. |
| 2009/0246296 | A1 | 10/2009 | Wink et al. |
| 2009/0281067 | A1 | 11/2009 | Toscano, III et al. |
| 2009/0298795 | A1 | 12/2009 | Paolocci et al. |
| 2011/0081427 | A1 | 4/2011 | Wink et al. |
| 2011/0144067 | A1 | 6/2011 | Toscano et al. |
| 2011/0160200 | A1 | 6/2011 | Mazhari et al. |
| 2012/0201907 | A1 | 8/2012 | Wink et al. |
| 2014/0235636 | A1 | 8/2014 | Toscano et al. |
| 2015/0004259 | A1 | 1/2015 | Wink et al. |
| 2015/0141378 | A1 | 5/2015 | Toscano et al. |
| 2015/0336880 | A1 | 11/2015 | Toscano et al. |
| 2016/0002156 | A1 | 1/2016 | Toscano et al. |
| 2016/0046570 | A1 | 2/2016 | Toscano et al. |
| 2016/0081951 | A1 | 3/2016 | Mazhari et al. |

FOREIGN PATENT DOCUMENTS

| | | |
|---|---|---|
| GB | 1 258 792 | 12/1971 |
| GB | 1 330 609 | 9/1973 |
| GB | 1570362 | 7/1980 |
| JP | 44025772 | 10/1969 |
| JP | 2001-519809 | 10/2001 |
| JP | 2007-264108 | 10/2007 |
| WO | WO 9632946 | 10/1996 |
| WO | WO 9819996 | 5/1998 |
| WO | WO/98/29408 | 7/1998 |
| WO | WO 9841206 | 9/1998 |
| WO | WO 9843621 | 10/1998 |
| WO | WO 9932464 | 7/1999 |
| WO | WO 9933823 | 7/1999 |
| WO | WO 0028988 | 5/2000 |
| WO | WO 0067754 | 11/2000 |
| WO | WO 0145703 | 6/2001 |
| WO | WO 02060378 | 8/2002 |
| WO | WO 03020221 | 3/2003 |
| WO | WO 03045369 | 6/2003 |
| WO | WO/2005/074598 | 8/2005 |
| WO | WO/2007/002444 | 1/2007 |
| WO | WO/2007/067333 | 6/2007 |
| WO | WO/2007/109175 | 9/2007 |
| WO | WO/2007/120839 | 10/2007 |
| WO | WO/2009/042970 | 4/2009 |
| WO | WO/2009/137717 | 11/2009 |
| WO | WO/2011/063339 | 5/2011 |
| WO | WO/2011/063400 | 5/2011 |
| WO | WO/2011/071951 | 6/2011 |
| WO | WO 2004/000215 | 12/2013 |

OTHER PUBLICATIONS

Advisory Action dated Nov. 17, 2004 in U.S. Appl. No. 10/226,412.

Advisory Action dated May 25, 2007 in U.S. Appl. No. 10/463,084.

Alewood, P.F. et al., "An Improved Preparation of N-(t-Butyl)-N-(3,5-dinitrobenzoyl)-nitroxyl", In Synthesis, vol. 1981, No. 2, Feb. 1981, pp. 121-122.

Alexandrou, N.E. and Nicolaides, D.N., "1,3-Addition reactions of the benzonitrile oxide with acid anions evidence for 1,4-acyl migration from oxygen to oxygen", In Tetrahedron Letters, vol. 7, No. 22, 1966, pp. 2497-2499.

Anderson, D.J. and Taylor, A.J., "Novel synthesis of pyrido[1,2-a]benzimidazoles via reaction of N-acyl arylhydroxylamines with pyridine", In Journal of Heterocyclic Chemistry, vol. 23, No. 4, Jul.-Aug. 1986, pp. 1091-1094.

Archer, S.L., "Phosphodiesterase Type 5 Inhibitors for Pulmonary Arterial Hypertension", In The New England Journal of Medicine, vol. 361, No. 19, Nov. 2009, pp. 1864-1871.

Backx, P.H. et al., "The relationship between contractile force and intracellular [Ca2+] in intact rat cardiac trabeculae", In The Journal of General Physiology, vol. 105, No. 1, Jan. 1995, pp. 1-19.

Badesch, D.B. et al., "Diagnosis and Assessment of Pulmonary Arterial Hypertension", In Journal of the American College of Cardiology, vol. 54, No. 1s1, Jun. 2009, pp. S55-S66.

Baldwin, J.E. et al., "Synthesis of chiral isoxazolidin-5-ones and their applications to the synthesis of β-amino-alanines and β-(N-hydroxyamino)-alanines", In Tetrahedron, vol. 50, No. 17, Apr. 1994, pp. 5049-5066.

Barst, R.J. et al., "Updated Evidence-Based Treatment Algorithm in Pulmonary Arterial Hypertension", In Journal of the American College of Cardiology, vol. 54, No. 1s1, Jun. 2009, pp. S78-S84.

Barst, R.J., "A review of pulmonary arterial hypertension: role of ambrisentan", In Vascular Health and Risk Management, wol. 3, No. 1, Feb. 2007, pp. 11-22.

Baskakov et al., Biologicheski Aktivnyth Soedinenii, 71:98-100 (1968).

Bassani, R.A. and Bers D.M., "Na—Ca Exchange is Required for Rest-decay but not for Rest-potential of Twitches in Rabbit and Rat Ventricular Myocytes", In Journal of Molecular and Cellular Cardiology, vol. 26, No. 10, Oct. 1994, pp. 1335-1347.

Bassoli, A. et al., "The heterolytic and homolytic cleavage of the oxygen-nitrogen bond in O,N-diacylhydroxylamines", In Bulletin de la Societe Chimique de France, vol. 2, 1988, pp. 293-297.

Bauer, N.R. et al., "Rodent models of PAH: are we there yet?", In Lung Cellular and Molecular Physiology, vol. 293, No. 3, Sep. 2007, pp. L580-L582.

Bazylinski, D.A. and Hollocher, T.C., "Evidence from the reaction between trioxodinitrate(II) and nitrogen-15-labeled nitric oxide that trioxodinitrate(II) decomposes into nitrosyl hydride and nitrite in neutral aqueous solution", Ub in Organic Chemistry, vol. 24, No. 25, Dec. 1985, pp. 4285-4288.

(56) References Cited

OTHER PUBLICATIONS

Bazylinski D.A. and Hollocher, T.C., "Metmyoglobin and methemoglobin as efficient traps for nitrosyl hydride (nitroxyl) in neutral aqueous solution", In Journal of the American Chemical Society, vol. 107, No. 26, Dec. 1985, pp. 7982-7986.
Bell, S.C. et al., "A new synthesis of 7-chloro-1,3-dihydro-5-phenyl-2H-1,4-benzodiazepin-2-one 4-oxide", In Journal of Heterocyclic Chemistry, vol. 4, No. 4, Dec. 1967, pp. 647-649.
Boerrigter, G. et al., "Des-serine-proline brain natriuretic peptide 3-32 in cardiorenal regulation", In Regulatory, Integrative and Comparative Physiology, vol. 292, No. 2, Feb. 2007, pp. R897-R901.
Bonner, F.T. and Hughes, M.N., "The Aqueous Solution Chemistry of Nitrogen in Low Positive Oxidation States", In Comments on Inorganic Chemistry, vol. 7, No. 4, 1983, pp. 215-234.
Bonner, F.T. and Ko, Y., "Kinetic, isotopic, and nitrogen-15 NMR study of N-hydroxybenzenesulfonamide decomposition: an nitrosyl hydride (HNO) source reaction", In Inorganic Chemistry, vol. 31, No. 12, Jun. 1992, pp. 2514-2519.
Borsche, W. and Feske, E., "Über β-Polynitroaryl-hydroxylamine, III", In Berichte der deutschen chemischen Gesellschaft, vol. 59, No. 4, Apr. 1926, pp. 683-690.
Bouzamondo, A. et al., "Beta-blocker treatment in heart failure", In Fundamental & Clinical Pharmacology, vol. 15, No. 2, Apr. 2001, pp. 95-109.
Boyland, E. and Nery, R., "The metabolism of urethane and related compounds", In Biochemical Journal, vol. 94, No. 1, pp. 198-208.
Boyland, E. and Nery, R., "The Oxidation of Hydroxamic Acids", In the Journal of the Chemical Society (month unknown) 1966, vol. 3, pp. 354-358.
Boyland, E. and Nery, R., "The synthesis and some reactions of N-hydroxycarbamates", In Journal of the Chemical Society C: Organic, vol. 1966, 1966, pp. 346-350.
Bristow, Michael R., "β-Adrenergic Receptor Blockade in Chronic Heart Failure", In Circulation, vol. 101, No. 5, Feb. 2000, pp. 558-569.
Bryant, I.R. and Dyall, L.K., "Reactions of N-Acyloxy-2-nitrobenzenamines. I. Thermolysis in Benzene or Bromobenzene", In Australian Journal of Chemistry, vol. 42, No. 12, 1989, pp. 2275-2288.
Calder, I.C. and Williams, P.J., "The thermal ortho-rearrangement of some carcinogenic N, O-diacetyl-N-arylhydroxylamines", In Chemico-Biological Interactions, vol. 11, No. 1, Jul. 1975, pp. 27-32.
Campbell, M.M. and Johnson, G., "Conversion of secopenicillanic acid derivatives into beta-lactam sulphimides and oxazolines", In Journal of the Chemical Society, Perkin Transactions 1, No. 23, 1975, pp. 1077-1081.
Canadian Cardiovascular Society, "The 2001 Canadian Cardiovascular Society Consensus Guideline Update for the Management and Prevention of Heart Failure", 2001, pp. 1-28.
Carpino, L.A. et al., "O-Acylhydroxylamines. I. Synthesis of O-Benzoylhydroxylamine", In Journal of the American Chemical Society, vol. 81, No. 4, Mar. 1959, pp. 955-957.
Catherwood, E., "Pulmonary Arterial Hypertension: A Few Steps on the Long March to Effective Treatment", In Cardiology Update, 2004, pp. 1-40.
Champion, H.C., "Comprehensive Invasive and Noninvasive Approach to the Right Ventricle—Pulmonary Circulation Unit", In Circulation, vol. 120, No. 11, Sep. 2009, pp. 992-1007.
Chavey, William E., II et al, "Guideline for the Management of Heart Failure Caused by Systolic Dysfunction: Part II. Treatment", In American Family Physician, vol. 64, No. 6, pp. 1045-1055.
Cheng, H. et al., "Amplitude Distribution of Calcium Sparks in Confocal Images: Theory and Studies with an Automatic Detection Method", In Biophysical Journal, vol. 76, No. 2, Feb. 1999, pp. 606-617.
Cheong, E. et al., "Nitroxyl triggers Ca2+ release from skeletal and cardiac sarcoplasmic reticulum by oxidizing ryanodine receptors", In Cell Calcium, vol. 37, No. 1, Jan. 2005, pp. 87-96.

Clozel, M. et al., "Bosentan Sildenafil, and Their Combination in the Monocrotaline Model of Pulmonary Hypertension in Rats", In Experimental Biology and Medicine, vol. 231, No. 6, Jun. 2006, pp. 967-973.
Colton, C.A. et al., "Nitroxyl anion regulation of the NMDA receptor", In Journal of Neurochemistry, vol. 78, No. 5, Sep. 2001, pp. 1126-1134.
Colucci, W.S., "Treatment of acute decompensated heart failure", Jun. 14, 2009, available at: http://www.uptodate.com/contents/treatment-of-acute-decompensated-heart-failure-general-considerations.
Conway, T.T. et al., "Diethylcarbamoylating/Nitroxylating Agents as Dual Action Inhibitors of Aldehyde Dehydrogenase:? A Disulfiram-Cyanamide Merger", In Journal of Medicinal Chemistry, vol. 42, No. 20, Sep. 1999, pp. 4016-4020.
Cortassa, S. et al., "A mitochondrial oscillator dependent on reactive oxygen species", In Biophysical Journal, vol. 87, No. 3, Sep. 2004, pp. 2060-2073.
Crawford, J.H. et al., "Hypoxia, red blood cells, and nitrite regulate NO-dependent hypoxic vasodilation", In Blood, vol. 107, No. 2, Jan. 2006, pp. 566-575.
Csonka, C. et al., "Classic Preconditioning Decreases the Harmful Accumulation of Nitric Oxide During Ischemia and Reperfusion in Rat Hearts", In Circulation, vol. 100, No. 22, Nov. 1999, pp. 2260-2266.
De Witt, B.J. et al., "Comparison of responses to novel nitric oxide donors in the feline pulmonary vascular bed", In European Journal of Pharmacology, vol. 430, No. 2-3, Nov. 2001, pp. 311-315.
Devaraj, V.R. et al., "Yeast Aldehyde Dehydrogenase Sensitivity to Inhibition by Chlorpropamide Analogues as an Indicator of Human Aldehyde Dehydrogenase Sensitivity to These Agents", In Advances in Experimental Medicine and Biology, vol. 414, 1997, pp. 155-169.
Diaz, M.E. et al., "The control of sarcoplasmic reticulum Ca content in cardiac muscle", In Cell Calcium, vol. 38, No. 3-4, Sep.-Oct. 2005, p. 391-396.
DiDomenico, R.J., "Guidelines for Acute Decompensated Heart Failure Treatment", In Annals of Pharmacotherapy, vol. 38, No. 4, Apr. 2004, pp. 649-660.
Dostal, D.E. et al., "Detection of angiotensin I and II in cultured rat cardiac myocytes and fibroblasts", In American Journal of Physiology Cell Physiology, vol. 263, No. 4, Oct. 1992, pp. C851-C863.
Doyle, M.P. et al., "Oxidation and reduction of hemoproteins by trioxodinitrate(II). The role of nitrosyl hydride and nitrite", In Journal of the American Chemical Society, vol. 110, No. 2, Jan. 1988, pp. 593-599.
Examination Report dated Apr. 10, 2015 in Australian Patent Application No. 2010328234.
Fahmy, O.G. and Fahmy M.J., "Cytotoxic and mütagenic activation of urethane by N-hydroxylation and O-esterification", In Chemico-Biological Interactions, vol. 1, No. 3, Feb. 1970, pp. 257-270.
Faul, J.L. et al., "Triptolide Attenuates Pulmonary Arterial Hypertension and Neointimal Formation in Rats", In American Journal of Respiratory and Critical Care Medicine, vol. 162, No. 6, Dec. 2000, pp. 2252-2258.
Feelisch, M., "Nitroxyl gets to the heart of the matter", In Proceedings of the National Academy of Sciences, vol. 100, No. 9, Apr. 2003, pp. 4978-4980.
Feld, Y. et al., "Future strategies for the treatment of diastolic heart failure", In Acute Cardiac Care, vol. 8, No. 1, Jan. 2006, pp. 13-20.
Felker, G.M. et al., "Heart failure etiology and response tomilrinone in decompensated heart failure", In Journal of the American College of Cardiology, vol. 41, No. 6, Mar. 2003, pp. 997-1003.
Felker, G.M. et al., "Risk stratification after hospitalization for decompensated heart failure", In Journal of Cardiac Failure, vol. 10, No. 6, Dec. 2004, pp. 460-466.
Ferreira, L.M. et al., "Reaction of aromatic nitroso compounds with chemical models of 'thiamine active aldehyde'", In Tetrahedron, vol. 64, No. 33, Aug. 2008, pp. 7759-7770.
Fieser, L.F. and Hershberg, E.B., "20-Methyl-4-azacholanthrene", In Journal of the American Chemical Society, vol. 62, No. 7, Jul. 1940, pp. 1640-1645.

(56) References Cited

OTHER PUBLICATIONS

Fitzhugh, A.L. and Keefer, L.K., "Diazeniumdiolates:: Pro- and antioxidant applications of the "NONOates"", In Free Radical Biology and Medicine, vol. 28, No. 10, May 2000, pp. 1463-1469.

Forfia, P., "Challenges and Controversies in Heart Failure: Echo vs. Cath: seperating the right from the left", In Proceedings of Satellite Symposium, 13th Annual Heart Failure Society Meeting, Philadelphia, Pennsylvania, United States, Sep. 2009.

Form PCT/ISA/206 (Invitation to Pay Additional Fees and, Where Applicable, Protest Fee) dated Oct. 28, 2011 in International Patent Application No. PCT/US2010/059335.

Forrester, A.R. and Irikawa, H., "E.s.r. spectra of cyclic oxyamidyls", In Journal of the Chemical Society, Chemical Communications, No. 5, 1981, pp. 253-254.

Franklin, K.M. and Aurigemma, G.P., "Prognosis in Diastolic Heart Failure", In Progress in Cardiovascular Diseases, vol. 47, No. 5, Mar.-Apr. 2005, pp. 333-339.

Froehlich, J.P. et al., "Studies of sarcoplasmic reticulum function and contraction duration in young adult and aged rat myocardium", In Journal of Molecular and Cellular Cardiology, vol. 10, No. 5, May 1978, pp. 427-436.

Fukuto, J.M. et al., "N,O-Diacylated-N-hydroxyarylsulfonamides: Nitroxyl precursors with potent smooth muscle relaxant properties", In Biochemical and Biophysical Research Communications, vol. 187, No. 3, Sep. 1992, pp. 1367-1373.

Fukuto, J.M. et al., "Nitroxyl (HNO): Chemistry, Biochemistry, and Pharmacology", In Annual Review of Pharmacology and Toxicology, vol. 45, Feb. 2005, pp. 335-355.

Fukuto, J.M. et al., "The Chemistry and Biology of Nitroxyl (HNO): A Chemically Unique Species with Novel and Important Biological Activity", In ChemBioChem, vol. 6, No. 4, Apr. 2005, pp. 612-619.

Fukuto, J.M. et al., "The pharmacological activity of nitroxyl: a potent vasodilator with activity similar to nitric oxide and/or endothelium-derived relaxing factor", In The Journal of Pharmacology and Experimental Therapeutics, vol. 263, No. 2, Nov. 1992, pp. 546-551.

Fukuto, J.M. et al., "The Physiological Chemistry and Biological Activity of Nitroxyl (HNO):? The Neglected, Misunderstood, and Enigmatic Nitrogen Oxide", In Chemical Research in Toxicology, vol. 18, No. 5, Apr. 2005, pp. 790-801.

Gao, W.D. et al., "Calcium cycling and contractile activation in intact mouse cardiac muscle", In The Journal of Physiology, vol. 507, No. 1, Feb. 1998, pp. 175-184.

Gao, W.D. et al., "Myofilament Ca2+ sensitivity in intact versus skinned rat ventricular muscle", In Circulation Research, vol. 74, No. 3, Mar. 1994, pp. 408-415.

Gao, W.D. et al., "Relationship Between Intracellular Calcium and Contractile Force in Stunned Myocardium", In Circulation Research, vol. 76, No. 6, Jun. 1995, pp. 1036-1048.

Gelvan, D. et al., "Cardiac reperfusion damage prevented by a nitroxide free radical", In Proceedings of the National Academy of Sciences, vol. 88, No. 11, Jun. 1991, pp. 4680-4684.

Gheorghiade, M. and Pang, P.S., "Acute Heart Failure Syndromes", In Journal of the American College of Cardiology, vol. 53, No. 7, Feb. 2009, pp. 557-573.

Ghodsi, F. and Will, J.A., "Changes in pulmonary structure and function induced by monocrotaline intoxication", In American Journal of Physiology Heart and Circulatory Physiology, vol. 240, No. 2, Feb. 1981, pp. H149-H155.

Ghofrani, H.A. et al., "Future Perspectives for the Treatment of Pulmonary Arterial Hypertension", In Journal of the American College of Cardiology, vol. 54, No. 1s1, Jun. 2009, pp. S108-S117.

Ghofrani, H.A. et al., "Nitric oxide pathway and phosphodiesterase inhibitors in pulmonary arterial hypertension", In Journal of the American College of Cardiology, vol. 43, No. 12s1 Jun. 2004, pp. S68-S72.

Greenway, S. et al., "S100A4/Mts1 Produces Murine Pulmonary Artery Changes Resembling Plexogenic Arteriopathy and is Increased in Human Plexogenic Arteriopathy", In The American Journal of Pathology, vol. 164, No. 1, Jan. 2004, pp. 253-262.

Hain, J. et al., "Phosphorylation Modulates the Function of the Calcium Release Channel of Sarcoplasmic Reticulum from Cardiac Muscle", In The Journal of Biological Chemistry, vol. 270, No. 5, Feb. 1995, pp. 2074-2081.

Hare, J.M. et al., "Nitric Oxide Inhibits the Positive Inotropic Response to β-Adrenergic Stimulation in Humans With Left Ventricular Dysfunction", In Circulation, vol. 92, No. 8, Oct. 1995, pp. 2198-2203.

Hare, J.M. et al., "Pertussis toxin-sensitive G proteins influence nitric oxide synthase III activity and protein levels in rat heart", In The Journal of Clinical Investigation, vol. 101, No. 6, Mar. 1998, pp. 1424-1431.

Harris, R.B. and Wilson, I.B., "Synthesis of tert-butyl aminocarbonate, a new type of compound that can be used to acylate amines", In Tetrahedron Letters, vol. 24, No. 3, 1983, pp. 231-232.

Hart, C.Y.T. et al., "Differential effects of natriuretic peptides and NO on LV function in heart failure and normal dogs", In American Journal of Physiology Heart and Circulatory Physiology, vol. 261, No. 1, Jul. 2001, pp. H146-H154.

Hassoun, P.M. et al., "Inflammation, Growth Factors, and Pulmonary Vascular Remodeling", In Journal of the American College of Cardiology, vol. 54, No. 1s1, Jun. 2009, pp. S10-S19.

Heart Failure Society of America, "Section 1: Development and Implementation of a Comprehensive Heart Failure Practice Guideline", 2006, pp. 1-95.

Heine, H.W. et al., "Synthesis and reactions of N-(2,4-dichloro-6-oxo-2,4-cyclohexadien-1-ylidene)-4-nitrobenzamide with alkenes", In The Journal of Organic Chemistry, vol. 49, No. 14, Jul. 1984, pp. 2560-2565.

Herscheid, J.D.M. et al., "Synthesis of dehydroamino acids and didehydrodioxopiperazines and their conversion into a-mercapto-a-amino acid derivatives", In Recueil des Travaux Chimiques des Pays-Bas, vol. 100, No. 2, 1981, pp. 73-78.

Heywood, B.J. and Leeds, W.G., "Herbicidal Carbamates-Benzenesulphonylcarbamates", In the Journal of the Science of Food and Agriculture, (month unknown) 1968, vol. 19, No. S1, pp. 3-7.

Hoeper, M.M. et al., "Diagnosis, Assessment, and Treatment of Non-Pulmonary Arterial Hypertension Pulmonary Hypertension", In Journal of the American College of Cardiology, vol. 54, No. 1s1, Jun. 2009, pp. S85-S96.

Horner, L. and Steppan, H., "Course of substitutions XII. Rearrangement and pyrolytic degradation of acylated hydroxylamines", In Justus Liebigs Annalen der Chemie, vol. 606, No. 1, Jul. 1957, pp. 24-47.

Humbert, M. et al., "Treatment of Pulmonary Arterial Hypertension", In The New England Journal of Medicine, vol. 351, No. 14, Sep. 2004, pp. 1425-1436.

Hunt, S.A., "ACC/AHA Guidelines for the Evaluation and Management of Chronic Heart Failure in the Adult", Report of the American College of Cardiology/American Heart Association Task Force on Practice Guidelines, The American College of Cardiology and the American Heart Association, Inc., Nov. 2001, pp. 1-56.

Ingall, T.J., "Preventing Ischemic Stroke", In Postgraduate Medicine, vol. 107, No. 6, May 2000, pp. 34-50.

Internataional Search Report dated Feb. 14, 2012 in International Patent Application No. PCT/US2010/059335.

International Search Report dated Nov. 17, 2006 in International Patent Application No. PCT/US2006/024545.

International Search Report dated Feb. 14, 2011 in International Patent Application No. PCT/US2010/057640.

International Search Report dated Feb. 14, 2011 in International Patent Application No. PCT/US2010/057844.

International Search Report dated Feb. 2, 2012 in Internabonal Patent Application No. PCT/US2010/059331.

Isselbacher, E. et al., "Treatment of Heart Failure", in Harrison's Principles of Internal Medicine, 13th Edition, McGraw-Hill, Inc., New York, New York, 1994, pp. 1002-1006.

Ivy, D.D. et al., "Development of Occlusive Neointimal Lesions in Distal Pulmonary Arteries of Endothelin B Receptor—Deficient Rats", In Circulation, vol. 111, No. 22, Jun. 2005, pp. 2988-2996.

(56) References Cited

OTHER PUBLICATIONS

Jackman, G.B. et al., "Studies in the Field of Diuretic Agents", In Journal of Pharmacy and Pharmacology, vol. 15, No. 1, Sep. 1963, pp. 202-211.

Jiang, M.T. et al., "Abnormal Ca2+ Release, but Normal Ryanodine Receptors, in Canine and Human Heart Failure", In Circulation Research, vol. 91, No. 11, Nov. 2002, pp. 1015-1022.

Jones, L.W. and Hurd, C.D., "Rearrangements of Some New Hydroxamic Acids Related to Heterocyclic Acids and to Diphenyl- and Triphenyl-Acetic Acids", In Journal of the American Chemical Society, vol. 43, No. 11, Nov. 1921, pp. 2422-2448.

Kass, D.A. et al., "What Mechanisms Underlie Diastolic Dysfunction in Heart Failure?", In Circulation Research, vol. 94, No. 12, Jun. 2004, pp. 1533-1542.

Kass, D.A., "Assessment of Diastolic Dysfunction", In Cardiology Clinics, vol. 18, No. 3, Aug. 2000, pp. 571-586.

Kass, D.A., "Rescuing a failing heart: putting on the squeeze", In Nature Medicine, vol. 15, No. 1, Jan. 2009, pp. 24-25.

Kato, R. et al., "Milrinone decreases both pulmonary arterial and venous resistances in the hypoxic dog", In British Journal of Anaesthesia, vol. 81, No. 6, Dec. 1998, pp. 920-924.

Katori, T. et al., "Calcitonin Gene-Related Peptide In Vivo Positive Inotropy is Attributable to Regional Sympatho-Stimulation and is Blunted in Congestive Heart Failure", In Circulation Research, vol. 96, No. 2, Feb. 2005, pp. 234-243.

Katori, T., "The novel organic nitroxyl donor, isopropylamine/nitric oxide exerts beta-independent positive inotropy/lusitropy in failing hearts", In Journal of the American College of Cardiology, vol. 43, No. 5s1 , Mar. 2004, p. A218.

Kawase, M. et al., "Electrophilic aromatic substitution with N-methoxy-N-acylnitrenium ions generated from N-chloro-N-methoxy amides: syntheses of nitrogen heterocyclic compounds bearing a N-methoxy amide group", In The Journal of Organic Chemistry, vol. 54, No. 14, Jul. 1989, pp. 3394-3403.

Kerwin Jr., J.F. et al., "Nitric Oxide: A New Paradigm for Second Messengers", In Journal of Medicinal Chemistry, vol. 38, No. 22, Oct. 1995, pp. 4343-4362.

Khan, S.S. et al., Managed Care Interventions for Improving Outcomes in Acute Heart Failure Syndromes, vol. 17, No. 9 Suppl, Sep. 2008, pp. S273-S286.

Khush, K.K. et al., "Effect of pulmonary hypertension on clinical outcomes in advanced heart failure: Analysis of the Evaluation Study of Congestive Heart Failure and Pulmonary Artery Catheterization Effectiveness (ESCAPE) database", In American Heart Journal, vol. 157, No. 6, Jun. 2009, pp. 1026-1034.

Kim, B. et al., "Indium Mediated Reductive Acylations of Nitroarenes Towards N,O-Diacylated N-Arylhydhoxylamies", In Synthetic Communications, vol. 31, No. 23, 2001, pp. 3577-3586.

Kim, W. et al., "Attenuation of NMDA Receptor Activity and Neurotoxicity by Nitroxyl Anion, NO-", In Neuron, vol. 24, No. 2, Oct. 1999, pp. 461-469.

King, S.B. and Nagasawa, H.T., "Chemical approaches toward generation of nitroxyl", In Methods in Enzymology, vol. 301, 1999, pp. 211-220.

Klemm, L.H. and Porter, Q.N., "Selective electrochemical reductive acetylation of aromatic nitrosulfones", In The Journal of Organic Chemistry, vol. 46, No. 10, May 1981, pp. 2184-2186.

Koga, H. et al., "The mutagenic activity of ethyl N-hydroxycarbamate and its related compounds in *Salmonella typhimurium*", In Mutation Research/Genetic Toxicology, vol. 78, No. 2, Jun. 1980, pp. 145-150.

Kohout, F.C. and Lampe, F.W., "On the Role of the Nitroxyl Molecule in the Reaction of Hydrogen Atoms with Nitric Oxide", In Journal of the American Chemical Society, vol. 87, No. 24, Dec. 1965, pp. 5795-5796.

Kubalova, Z. et al., "Abnormal intrastore calcium signaling in chronic heart failure", In Proceedings of the National Academy of Sciences, vol. 102, No. 39, Sep. 2005, pp. 14104-14109.

Kurita, J. et al., "Syntheses of 1,4-Oxazepines, 1,4-Diazepines, and Their 5-Oxo Derivatives from 2-Pyridones", In Heterocycles, vol. 26, No. 12, 1987, pp. 3085-3088.

Lam, C.S.P. et al., "Pulmonary Hypertension in Heart Failure With Preserved Ejection Fraction", In Journal of the American College of Cardiology, vol. 53, No. 13, Mar. 2009, pp. 1119-1126.

Lee, J. et al., "Analysis of structure—activity relationships for the 'B-region' of N-(3-acyloxy-2-benzylpropyl) -N'-[4-(methylsulfonylamino)benzyl]thiourea analogues as vanilloid receptor antagonists", In Bioorganic & Medicinal Chemistry Letters, vol. 14, No. 9, May 2004, pp. 2291-2297.

Lee, M.J.C. et al., "N-Hydroxybenzenecarboximidic Acid Derivatives: A New Class of Nitroxyl-Generating Prodrugs", In Nitric Oxide, vol. 5, No. 3, Jun. 2001, pp. 278-287.

Lee, M.J.C., et al., "Prodrugs of Nitroxyl as Inhibitors of Aldehyde Dehydrogenase", In the Journal of Medicinal Chemistry, vol. 35, No. 20, Oct. 1992, pp. 3648-3652.

Lewis, G.D., "The Role of the Pulmonary Vasculature in Heart Failure With Preserved Ejection Fraction", In Journal of the American College of Cardiology, vol. 53, No. 13, Mar. 2009, pp. 1127-1129.

Li, H. et al., "Polynitroxyl-albumin (PNA) enhances myocardial infarction therapeutic effect of tempol in rat hearts subjected to regional ischemia-reperfusion", In Free Radical Biology and Medicine, vol. 32, No. 8, Apr. 2002, pp. 712-719.

Lin, J. et al., "An investigation of the intramolecular ene reaction of N-acyl imines", In The Journal of Organic Chemistry, vol. 51, No. 2, Jan. 1986, pp. 167-174.

Little, W.C. et al., "The left ventricular dP/dtmax-end-diastolic volume relation in closed-chest dogs", In Circulation Research, vol. 56, No. 6, Jun. 1985, pp. 808-815.

Loev, B. et al., "Bis-N,O-diacetylhydroxylamine analog of diaminodiphenyl sulfone possessing antimalarial activity", In Journal of Medicinal Chemistry, vol. 16, No. 2, Feb. 1973, pp. 161-163.

Lowes, B.D. et al., "Inotropes in the beta-blocker era", In Clinical Cardiology, vol. 23, No. S3, Mar. 2000, pp. III11-III16.

Ma, X.L. et al., "Opposite effects of nitric oxide and nitroxyl on postischemic myocardial injury", In Proceedings of the National Academy of Sciences, vol. 96, No. 25, Dec. 1999, pp. 14617-14622.

Macchia, A. et al., "A meta-analysis of trials of pulmonary hypertension: A clinical condition looking for drugs and research methodology", In American Heart Journal, vol. 153, No. 6, Jun. 2007, pp. 1037-1047.

MacLennan, D.H. and Kranias, E.G., "Phospholamban: a crucial regulator of cardiac contractility", In Nature Reviews Molecular Cell Biology, vol. 4, Jul. 2003, pp. 566-577.

Mahaney, J.E., "Intermolecular Conformational Coupling and Free Energy Exchange Enhance the Catalytic Efficiency of Cardiac Muscle SERCA2a following the Relief of Phospholamban Inhibition", In Biochemistry, vol. 44, No. 21, May 2005, pp. 7713-7724.

Maragos, C.M. et al., "Complexes of .NO with nucleophiles as agents for the controlled biological release of nitric oxide. Vasorelaxant effects", In Journal of Medicinal Chemistry, vol. 34, No. 11, Nov. 1991, pp. 3242-3247.

Martin, N.I., "NG-Hydroxyguanidines from Primary Amines", In Organic Letters, vol. 8, No. 18, Jul. 2006, pp. 4035-4038.

Mathier, Presentation entitled: "Management of PAH: Similarities and Differences with Heart Failure Care", Pulmonary Hypertension Program, University of Pittsburgh Medical Center (undated).

Matter, C.M. et al., "Effect of NO Donors on LV Diastolic Function in Patients With Severe Pressure-Overload Hypertrophy", In Circulation, vol. 99, No. 18, May 1999, pp. 2396-2401.

McLaughlin, V.V. et al., "ACCF/AHA 2009 Expert Consensus Document on Pulmonary Hypertension", In Journal of the American College of Cardiology, vol. 53, No. 17, Apr. 2009, pp. 1573-1619.

McLaughlin, V.V. et al., "End Points and Clinical Trial Design in Pulmonary Arterial Hypertension", In Journal of the American College of Cardiology, vol. 54, No. 1s1, Jun. 2009, pp. S97-S107.

Milewska, M.J. and Chimiak, M.J., "Oxidation of Amino Acids. IV. Reaction of Dibenzoyl Peroxide With ?-Amino Acid Esters", In Australian Journal of Chemistry, vol. 40, No. 11, 1987, pp. 1919-1922.

(56) References Cited

OTHER PUBLICATIONS

Mincione, F. et al., "Carbonic Anhydrase Inhibitors: Inhibition of Isozymes I, II and IV with N-Hydroxysulfonamides—A Novel Class of Intraocular Pressure Lowering Agents", In Journal of Enzyme Inhibition and Medicinal Chemistry, vol. 13, No. 4, Jan. 1998, pp. 267-284.
Miranda. K.M. et al., "Donors of HNO", In Current Topics in Medicinal Chemistry, vol. 5, No. 7, 2005, pp. 649-664.
Mongillo, M. et al., "Compartmentalized Phosphodiesterase-2 Activity Blunts β-Adrenergic Cardiac Inotropy via an NO/cGMP-Dependent Pathway", In Circulation Research, vol. 98, No. 2, Feb. 2006, pp. 226-234.
Morrell, N.W. et al., "Cellular and Molecular Basis of Pulmonary Arterial Hypertension", In Journal of the American College of Cardiology, vol. 54, No. 1s1, Jun. 2009, pp. S20-S31.
Morris, G.N. et al., "Exogenous inhaled nitric oxide as a selective pulmonary vasodilator", In Seminars in Anesthesia, Perioperative Medicine and Pain, vol. 15, No. 1, Mar. 1996, pp. 47-60.
Nagasawa, H.T. et al., "An N-hydroxylated derivative of cyanamide that inhibits yeast aldehyde dehydrogenase", In Alcohol, vol. 9, No. 5, Sep.-Oct. 1992, pp. 349-353.
Nagasawa, H.T. et al., "Carbethoxylating Agents as Inhibitors of Aldehyde Dehydrogenase", In Journal of Medicinal Chemistry, vol. 38, No. 11, May 1995, pp. 1872-1876.
Nagasawa, H.T. et al., "Prodrugs of Nitroxyl as Potential Aldehyde Dehydrogenase Inhibitors vis-a-vis Vascular Smooth Muscle Relaxants", In Journal of Medicinal Chemistry, vol. 38, No. 11, May 1995, pp. 1865-1871.
Naughton, P. et al., Induction of haem oxygenase-1 by nitroxyl anion (NP-) in cardiomycytes, In Journal of Physiology, vol. 531, 2001, p. 194P.
Neunhoeffer, O. and Gottschlich, R., "Acylierungsaktivität O-acetylierter Hydroxylamin-Derivate", In Justus Liebigs Annalen der Chemie, vol. 736, No. 1, Jul. 1970, pp. 100-109.
Nieminen, M.S. et al., "Executive summary of the guidelines on the diagnosis and treatment of acute heart failure", In European Hear Journal, vol. 24, No. 4, Feb. 2005, pp. 384-416.
Nishimura, T. et al., "Simvastatin Rescues Rats From Fatal Pulmonary Hypertension by Inducing Apoptosis of Neointimal Smooth Muscle Cells", In Circulation, vol. 108, No. 13, Sep. 2003, pp. 1640-1645.
Norris, A.J. et al., "Nitroxyl inhibits breast tumor growth and angiogenesis", In International Journal of Cancer, vol. 122, No. 8, Apr. 2008, pp. 1905-1910.
Notice of Allowance dated Sep. 15, 2014 in U.S. Appl. No. 12/962,544.
Office Action dated Apr. 23, 2014 in U.S. Appl. No. 12/962,544.
Office Action dated Oct. 14, 2011 in U.S. Appl. No. 12/949,533.
Office Action dated Oct. 6, 2014 in Japanese Patent Application No. 2012-54321 with English Translation.
Office Action dated Nov. 23, 2009 in U.S. Appl. No. 11/096,924.
Office Action dated Nov. 9, 2010 in U.S. Appl. No. 12/346,694.
Office Action dated Mar. 31, 2004 in U.S. Appl. No. 10/226,412.
Office Action dated Mar. 4, 2009 in U.S. Appl. No. 11/096,924.
Office Action dated Mar. 8, 2007 in U.S. Appl. No. 10/463,084.
Office Action dated Apr. 12, 2010 in U.S. Appl. No. 11/096,924.
Office Action dated Apr. 21, 2010 in U.S. Appl. No. 11/096,924.
Office Action dated Jul. 13, 2006 in U.S. Appl. No. 10/463,084.
Office Action dated Jul. 2, 2008 in U.S. Appl. No. 10/463,084.
Office Action dated Jul. 22, 2008 in U.S. Appl. No. 11/096,924.
Office Action dated Jul. 26, 2004 in U.S. Appl. No. 10/266,412.
Office Action dated Aug. 1, 2011 in U.S. Appl. No. 12/346,694.
Office Action dated Aug. 9, 2011 in U.S. Appl. No. 11/922,793.
Office Action dated Sep. 16, 2010 in U.S. Appl. No. 11/096,924.
Office Action dated Sep. 18, 2007 in U.S. Appl. No. 11/096,924.
Okada, K. et al., "Pulmonary hemodynamics modify the rat pulmonary artery response to injury. A neointimal model of pulmonary hypertension", In American Journal of Pathology, vol. 151, No. 4, Oct. 1997, pp. 1019-1025.

Owan, T.W. et al., "Epidemiology of Diastolic Heart Failure", In Progress in Cardiovascular Diseases, vol. 47, No. 5, Mar.-Apr. 2005, pp. 320-332.
Packer, Presentation entitled: "Pulmonary Hypertension vs Heart Faillure Left-Sided or Right-Sided?" (undated).
Pagliaro, P. et al. (2001). "Nitroxyl Anion is a Preconditioning Agent in Isolated Rat Heart," Circulation 104(17 Suppl.):II-263-II-264, Abstract 1265.
Pagliaro, P. et al., "Is nitroxyl anion involved in myocardial protection against ischaemia/reperfusion injury in isolated rat hearts?", In Proceedings of the Physiological Society, University of Bristol, United Kingdom, 2001, p. 143P.
Pagliaro, P. et al., "Nitroxyl affords thiol-sensitive myocardial protective effects akin to early preconditioning", In Free Radical Biology and Medicine, vol. 34, No. 1, Jan. 2003, pp. 33-43.
Pagliaro, P., "Differential biological effects of products of nitric oxide (NO) synthase: it is not enough to say NO", In Life Sciences, vol. 73, No. 17, Sep. 2003, pp. 2137-2149.
Paolocci, N. et al., "cGMP-independent inotropic effects of nitric oxide and peroxynitrite donors: potential role for nitrosylation", In American Journal of Physiology Heart and Circulatory Physiology, vol. 279, No. 4, Oct. 2000, pp. H1982-H1988.
Paolocci, N. et al., "Nitroxyl anion exerts redox-sensitive positive cardiac inotnopy in vivo by calcitonin gene-related peptide signaling", In Proceedings of the National Academy of Sciences, vol. 98, No. 18, Aug. 2001, pp. 10463-10468.
Paolocci, N. et al., "Nitroxyl anon improves in vivo contractile function and promotes active relaxation in experimental heart failure", In Italian Heart Journal, vol. 2, Suppl 3, 2001, Abst. No. 38.
Paolocci, N. et al., "Positive inotropic and lusitropic effects of HNO/NO—in failing hearts: Independence from β-adrenergic signaling", In Proceedings of the National Academy Sciences, vol. 100, No. 9, Apr. 2003, pp. 5537-5542.
Paolocci, N. et al., "The pharmacology of nitroxyl (HNO) and its therapeutic potential: Not just the janus face of NO", In Pharmacology & Therapeutics, vol. 113, No. 2, Feb. 2007, pp. 442-458.
Paolocci, N. et al., "The cardiovascular effects of HNO/nitroxyl", In Nitric Oxide, vol. 6, No. 4, Jun. 2002, p. 445 (Abst).
Park, Presentation entitled: "New Patient Population Research and Treatment Strategies for Pulmonary Hypertension", Pulmonary Vascular Disease Program, University of Maryland School of Medicine, Baltimore, Maryland (undated).
Paulus, W.J. and Bronzwaer, J.G.F., "Myocardial Contractile Effects of Nitric Oxide", In Heart Failure Reviews, vol. 7, No. 4, Oct. 2002, pp. 371-383.
Pelto, R.B. and Pratt, R.F., "Kinetics and mechanism of inhibition of a serine beta-lactamase by O-aryloxycarbonyl hydroxamates", In Biochemistry, vol. 47, No. 46, Nov. 18, 2008, pp. 12037-12046.
Peters, J.H. et al., "Mutagenic activity of antileprosy drugs and their derivatives", In International Journal of Leprosy and Other Mycobacterial Diseases, vol. 51, No. 1, Mar. 1983, pp. 45-53.
Petersen, J.W. and Felker, G.M., "Inotropes in the management of acute heart failure", In Critical Care Medicine, vol. 36, No. 1, Jan. 2008, pp. S106-S111.
Prakash et al., "Heterocycles from Sulphamylphenylhydrazines. Part I. 2-(p-Sulphamylphenyl)-1,2,3,-benzotriazoles and their 1-Oxides", In Journal of the Indian Chemical Society, vol. 41, No. 12, 1964, pp. 845-848.
Prestle, J. et al., "Ca2+-Handling Proteins and Heart Failure: Novel Molecular Targets?", In Current Medicinal Chemistry, vol. 10, No. 11, Jun. 2003, pp. 967-981.
Przybylski et al., "O-[N-Acylaminoacyl]-N[Arylsulfonyl]-Hydroxylamines and Their Applications in Synthesis of Peptide Bonds", In Roczniki Chemii, vol. 49, 1975, pp. 529-538.
Puri, A. et al., "Pulmonary arterial hypertension: current therapeutic strategies", In Nature Clinical Practice Cardiovascular Medicine, vol. 4, No. 6, Jun. 2007, pp. 319-329.
Quinones, M.A., "Assessment of Diastolic Function", In Progress in Cardiovascular Diseases, vol. 47, No. 5, Mar.-Apr. 2005, pp. 340-355.
Rabinovitch, M., "Pathobiology of Pulmonary Hypertension", In Annual Reviews of Pathology: Mechanisms of Disease, vol. 2, Feb. 2007, pp. 369-339.

(56) References Cited

OTHER PUBLICATIONS

Raju, B. et al., "Thiophenesulfonamides as endothelin receptor antagonists", In Bioorganic & Medicinal Chemistry Letters, vol. 6, No. 22, Nov. 1996, pp. 2651-2656.

Rastaldo, R. et al., "Cytochrome P-450 metabolite of arachidonic acid mediates bradykinin-induced negative inotropic effect", In American Journal of Physiology Heart and Circulatory Physiology, vol. 280, No. 6, Jun. 2001, pp. H2623-H2832.

Rehse, J. and Herpel, M., "New NO-donors with antithrombotic and vasodilating activities, Part 20. Azodioxides activated by electron acceptors in geminal or vicinal position", In Archiv der Pharmazie, vol. 331, No. 3, Mar. 1998, pp. 104-110.

Rehse, K. and Shahrouri, T., "Hydroxylamine Derivatives", In Archiv der Pharmazie, vol. 331, No. 11, Nov. 1998, pp. 365-367.

Remme, W.J. and Swedberg, K., "Guidelines for the diagnosis and treatment of chronic heart failure", In European Heart Journal, vol. 22, No. 17, Sep. 2001, pp. 1527-1560.

Santos, P. et al., "Selective O-acylation of aromatic hydroxylamines by 2-acylimidazolium and 2-acylbenzimidazolium salts", In Tetrahedron Letters, vol. 34, No. 23, Jun. 1993, pp. 3793-3796.

Schmidt, H.H.H.W. et al., "No?-NO from NO?synthase", In Proceddings of the National Academy of Sciences, vol. 93, No. 25, Dec. 1996, pp. 14492-14497.

Schraml, J. et al., "N,O-diacylhydroxylamines—structures in crystals and solutions", In Organic & Biomolecular Chemistry, vol. 2, No. 16, Aug. 2004, pp. 2311-2314.

Scozzafava, A. and Supuran, C.T., "Carbonic Anhydrase and Matrix Metalloproteinase Inhibitors", In Journal of Medical Chemistry, vol. 43, No. 20, Sep. 2000, pp. 3677-3687.

Senzaki, H. et al., "Improved Mechanoenergetics and Cardiac Rest and Reserve Function of In Vivo Failing Heart by Calcium Sensitizer EMD-57033", In Circulation, vol. 101, No. 9, Mar. 2000, pp. 1040-1048.

Sha, X. et al., "Hydrolysis of Acyloxy Nitroso Compounds Yields Nitroxyl (HNO)", In Journal of the American Chemical Society, vol. 128, No. 30, Jul. 2006, pp. 9687-9692.

Shafirovich, V. and Jymar, S.V., "Nitroxyl and its anion in aqueous solutions: Spin states, protic equilibria, and reactivities toward oxygen and nitric oxide", In Proceedings of the National Academy of Sciences, vol. 99, No. 11, May 2002, pp. 7340-7345.

Sham, J.S.K. et al., "Termination of Ca2+ release by a local inactivation of ryanodine receptors in cardiac myocytes", In Proceedings of the National Academy of Sciences, vol. 95, No. 25, Dec. 1998, pp. 15096-15101.

Sharpe, M.A. and Cooper, C.E., "Reactions of nitric oxide with mitochondrial cytochrome c: a novel mechanism for the formation of nitroxyl anion and peroxynitrite", In Biochemical Journal, vol. 332, 1998, No. 1, pp. 9-19.

Shin, D.D. et al., "Review of current and investigational pharmacologic agents for acute heart failure syndromes", In The American Journal of Cardiology, vol. 99, No. 2A, Jan. 2007, pp. 4A-23A.

Simonneau, G. et al., "Updated Clinical Classification of Pulmonary Hypertension", In Journal of the American College of Cardiology, vol. 54, No. 1s1, Jun. 2009, pp. S43-S54.

Singh, R.J. et al., "The Peroxynitrite Generator, SIN-1, Becomes a Nitric Oxide Donor in the Presence of Electron Acceptors", In Archives of Biochemistry and Biophysics, vol. 361, No. 2, Jan. 1999, pp. 331-339.

Sirovich, I. et al., "Activity of ruboxyl, a nitroxyl derivative of daunorubicin, on experimental models of colorectal cancer metastases", In Tumour Biology, vol. 20, No. 5, Sep.-Oct. 1999, pp. 276-276.

Sladek, N.E. et al., "Inhibition of ALDH3A1-catalyzed oxidation by chlorpropamide analogues", In Chemico-Biological Interactions, vol. 130-132, Jan. 2001, pp. 135-149.

Slotwiner-Nie, P.K. and Brandt, L.J., "Infectious Diarrhea in the Elderly", In Gastroenterology Ciinics, vol. 30, No. 3, Sep. 2001, pp. 625-635.

Smith, D.G. et al., "The inhibition of human cytomegalovirus (hCMV) protease by hydroxylamine derivatives", In Bioorganic & Medicinal Chemistry Letters, vol. 9, No. 21, Nov. 1999, pp. 3137-3142.

Smith, P.A.S. and Hein, G.E., "The Alleged Role of Nitroxyl in Certain Reactions of Aldehydes and Alkyl Halides", In Journal of the American Chemical Society, vol. 82, No. 21, Nov. 1960, pp. 5731-5740.

Stermitz, F.R. and Neiswander, D.W., "The reaction of phenylnitromethane with acetic anhydride/sodium acetate", In Tetrahedron, vol. 31, No. 7, 1975, pp. 665-656.

Stermitz, F.R. and Norris, F.A., "Oxidative acylation. New reaction of primary nitro compounds", In The Journal of Organic Chemistry, vol. 35, No. 2, Feb. 1970, pp. 527-528.

Stoyanovsky, D. et al., "Nitric oxide activates skeletal and cardiac ryanodine receptors", In Cell Calcium, vol. 21, No. 1, Jan. 1997, pp. 19-29.

Stoyanovsky, D.A. et al., "Effects of pH on the Cytotoxicity of Sodium Trioxodinitrate (Angeli's Salt)", In Journal of Medicinal Chemistry, vol. 47, No. 1, Dec. 2003, pp. 210-217.

Takahashi et al., "Reactive surfactants I. Hydroxamic acids and their derivatives", In Yukagaku, vol. 15, No. 12, 1967, pp. 633-637.

Takahira, R. et al., "Dexamethasone attenuates neutrophil infiltration in the rat kidney in ischemia/reperfusion injury: the possible role of nitroxyl", In Free Radical Biology and Medicine, vol. 31, No. 6, Sep. 2001, pp. 809-815.

Taraseviciene-Stewart, L. et al., "Absence of T Cells Confers Increased Pulmonary Arterial Hypertension and Vascular Remodeling", In American Journal of Respiratory and Critical Care Medicine, vol. 175, No. 12, Jun. 2007, pp. 1280-1289.

Taraseviciene-Stewart, L. et al., "Simvastatin causes endothelial cell apoptosis and attenuates severe pulmonary hypertension", In American Journal of Physiology Lung Cellular and Molecular Physiology, vol. 291, No. 4, Oct. 2006, pp. L668-L676.

Thevis, M. et al., "High speed determination of beta-receptor blocking agents in human urine by liquid chromatography/tandem mass spectrometry", In Biomedical Chromatography, vol. 15, No. 6, Oct. 2001, pp. 393-402.

Thomas, D.D. et al., "Guide for the use of nitric oxide (NO) donors as probes of the chemistry of NO and related redox species in biological systems", In Methods in Enzymology, vol. 359, 2002, pp. 84-105.

Tocchetti, C.G. et al., "Nitroxyl improves cellular heart function by directly enhancing cardiac sarcoplasmic reticulum Ca2+ cycling", In Circulation Research, vol. 100, No. 1, Jan. 2007, pp. 96-104.

Tomazic, A. et al., "Syntheses of some azinylhydroxylamines", In Journal of Heterocyclic Chemistry, vol. 16, No. 5, Jul. 1979, pp. 861-864.

Tosaki, A. et al., "Does the antiarrhythmic effect of DMPO originate from its oxygen radical trapping property or the structure of the molecule itself?", In Basic Research in Cardiology, vol. 87, No. 6, Nov.-Dec. 1992, pp. 536-547.

Tuder, R.M. et al., "Development and pathology of pulmonary hypertension", In Journal of the American College of Cardiology, vol. 54, No. 1s1, Jun. 2009, pp. S3-S9.

Urbanski, T., "Reactions of Nitroparaffins. Part III. The reaction of primary Nitroparaffins with acetic anhydride", In Journal of the Chemical Society, 1949, pp. 3374-3376.

Vanuffelen, B.E. et al., "Intracellular but not extracellular conversion of nitroxyl anion into nitric oxide leads to stimulation of human neutrophil migration", In The Biochemical Journal, vol. 330, No. 2, Mar. 1998, pp. 719-722.

Wei, P.H.L. et al., "Fused-ring systems containing 1,2,4-benzo thiadiazines. II. Reactions of o-amino-n-hydroxybenzenesulfonamides", In Journal of Heterocyclic Chemistry, vol. 3, No. 1, Mar. 1966, pp. 1-4.

White, R.J. et al., "Plexiform-like lesions and increased tissue factor expression in a rat model of severe pulmonary arterial hypertension", In American Journal of Physiology Lung Cellular and Molecular Physiology, vol. 293, No. 3, Sep. 2007, pp. L583-L590.

Wiley, R.H. et al., "Some a-Arylsulfonamido Acids and Amides", In Journal of the American Chemical Society, vol. 74, No. 24, Dec. 1952, pp. 6298-6299.

(56) References Cited

OTHER PUBLICATIONS

Wink, D.A. et al., "Orthogonal properties of the redox siblings nitroxyl and nitric oxide in the cardiovascular system: a novel redox paradigm", In American Journal of Physiology Heart and Circulatory Physiology, vol. 285, No. 6, Dec. 2003, pp. H2264-H2276.
Wood, P. et al., "Diastolic heart failure: progress, treatment challenges, and prevention", In Canadian Journal of Cardiology, vol. 27, No. 3, May-Jun. 2011, pp. 302-310.
Written Opinion of the International Search Authority dated Nov. 17, 2006 in International Patent Application No. PCT/US2006/024545.
Written Opinion of the International Searching Authority dated Feb. 14, 2011 in International Patent Application No. PCT/US2010/057640.
Written Opinion of the International Searching Authority dated Feb. 14, 2011 in International Patent Application No. PCT/US2010/057844.
Written Opinion of the International Searching Authority dated Feb. 14, 2012 in International Patent Application No. PCT/US2010/059335.
Written Opinion of the International Searching Authority dated Feb. 2, 2012 in International Patent Application No. PCT/US2010/059331.
Wrobel, J. et al., "Synthesis of (bis)Sulfonic acid, (bis)Benzamides as follicle-Stimulating hormone (FSH) antagonists", In Bioorganic & Medicinal Chemistry, vol. 10, No. 3, Mar. 2002, pp. 639-656.
Xu, L. et al. "Activation of the Cardiac Calcium Release Channel (Ryanodine Receptor) by Poly-S-Nitrosylation", In Science, vol. 279, No. 5348, Jan. 1998, pp. 234-237.
Yagodina, O.V. et al., "Acylation and oxidation of 4-chloro-6-hydroxyaminopyrimidines. Synthesis of 4-chloro-6-nitro(nitroso)pyrimidines", In Chemistry of Heterocyclic Compounds, vol. 25, No. 8, Aug. 1989, pp. 908-913.
Yturralde, R.F. and Gaasch, W.H., "Diagnostic criteria for diastolic heart failure", In Progress in Cardiovascular Diseases, vol. 47, No. 5, Mar.-Apr. 2005, pp. 314-319.
Yu, L. et al., "Nitric oxide: a mediator in rat tubular hypoxia/reoxygenation injury", In Proceedings of the National Academy of Sciences, vol. 91, No. 5, Mar. 1994, pp. 1691-1695.
Zaccolo, M. and Pozzan, T., "Discrete microdomains with high concentration of cAMP in stimulated rat neonatal cardiac myocytes", In Science, vol. 295, No. 5560, Mar. 2002, pp. 1711-1715.
Zahradnikova, A. et al., "Inactivation of the cardiac ryanodine receptor calcium release channel by nitric oxide", In Cell Calcium, vol. 22, No. 6, Dec. 1997, pp. 447-453.
Zaiman, A. et al., "One hundred years of research in the pathogenesis of pulmonary hypertension", In American Journal of Respiratoty Cell and Molecular Biology, vol. 33, No. 5, Nov. 2005, pp. 425-431.
Zamora, R. et al., "Oxidative release of nitric oxide accounts for guanylyl cyclase stimulating, vasodilator and anti-platelet activity of Piloty's acid: a comparison with Angeli's salt", In Biochemistrry Journal, vol. 312, No. 2, Dec. 1995, pp. 333-339.
Zheng, J. et al., "Three-dimensional quantitative stucture-activity relationship (CoMFA and CoMSIA) studies on galardin derivatives as gelatinase A (matrix metalloproteinase 2) inhibitors", In Journal of Enzyme Inhibition and Medicinal Chemistry, vol. 23, No. 4, Aug. 2008, pp. 445-453.
Zhou, Y.Y. et al., "Constitutive beta2-adrenergic signalling enhances sarcoplasmic reticulum Ca2+ cycling to augment contraction in mouse heart", In The Journal of Physiology, vol. 521 No. 2, Dec. 1999, pp. 351-361.
Zile, M.R. et al., "Diastolic heart failure: definitions and terminology", In Progress in Cardiovascular Diseases, vol. 47, No. 5, Mar.-Apr. 2005, pp. 307-313.
Zinner, "Darstellung und Aylierungen von 1.1-Dialyl-2-hydroxyhamstoffen", In Arch. Pharmaz, vol. 307, 1974, pp. 7-12.
Zinner, "Hydroxylamine derivatives. VII. Preparation and reactions of some substituted N-hydroxyurethans", In Archiv der Pharmazie und Berichte der Deutschen, vol. 292, 1959, pp. 329-336.
Ziolo, M.T. et al., "Positive and negative effects of nitric oxide on Ca(2+) sparks: influence of beta-adrenergic stimulation", In American Journal of Physiology Heart and Circulatory Physiology, vol. 281, No. 6, Dec. 2001, pp. H2295-H2303.
Zweier, J.L. et al., "Non-enzymatic nitric oxide synthesis in biological systems", In Biochimica et Biophysica Acta, vol. 1411, No. 203, May 1999, pp. 250-262.
Office Action dated Aug. 19, 2014 in Australian Patent Application No. 2010328230.
Office Action dated Aug. 14, 2014 in Chinese Patent Application No. 201080063220.9.
Office Action dated Apr. 10, 2015 in Australian Patent Application No. 2010328234.
Office Action dated Jul. 23, 2014 in Australian Patent Application No. 2010328234.
Office Action dated Apr. 1, 2014 in Chinese Patent Application No. 201080063223.2.
Office Action dated Dec. 1, 2014 in Chinese Patent Application No. 201080063223.2.
Office Action dated Aug. 17, 2015 in Chinese Patent Application No. 201080063223.2.
Office Action dated Apr. 6, 2016 in European Patent Application No. 10793381.4.
Office Action dated Oct. 10, 2014 in Japanese Patent Application No. 2012-543213.
Office Action dated Nov. 20, 2015 in U.S. Appl. No. 14/262,221.
Wang, F. et al., "Matrix Metalloproteinase and Heart Failure", In the Journal of Applied Clinical Pediatrics, vol. 20, No. 11, Nov. 2005, pp. 1149-1150.
Conway, T.T. et al., "Prodrugs of Nitroxyl and Nitrosobenzene as Cascade Lateniated Inhibitors of Aldehyde Dehydrogenase", In the Journal of Medicinal Cehmistry, vol. 41, No. 15, 1998, pp. 2903-2909.
Forrester, A.R., "Acyloxy-aminyls and -amidyls", In Tetrahedron Letters, vol. 19, No. 51, 1978, pp. 5139-5142.
Hand, E.S., "Catalytic Reduction of 4-nitropyridine 1-oxide", In the Journal of Heterocyclic Chemistry, vol. 12, No. 5, 1975, pp. 1063-1064.
Likhar, P.R., "Polyaniline Nanofiber Supported FeCl3: An Efficient and Reusable Heterogeneous Catalyst for the Acylation of Alcohols and Amines with Acetic Acid", In the Journal of Molecular Catalysis A: Chemical, vol. 302, No. 1-2, Apr. 2009, pp. 142-149.
Jeffrey, A.M., "Lack of DNA Binding in the Rat Nasal Mucosa and Other Tissues of the Nasal Toxicants Roflumilast, a Phosphodiesterase 4 Inhibitor, and a Metabolite, 4-amino-3,5-dichloropyridine, in Contrast to the Nasal Carcinogen 2,6-dimethylaniline", In Drug and Chemical Toxicology, vol. 25, No. 1, 2002, pp. 93-107.
Rautio, J. et al., "Prodrugs: Design and Clinical Applications", In Nature Reviews Drug Discover, vol. 7, Feb. 2008, pp. 255-270.
Office Action dated Oct. 14, 2014 in Japanese Patent Application No. 2012-543211.
Office Action dated May 19, 2016 in U.S. Appl. No. 14/262,223.

* cited by examiner

BIS-ACYLATED HYDROXYLAMINE DERIVATIVES

This application is a divisional of application Ser. No. 12/962,544, filed Dec. 7, 2010 now U.S. Pat. No. 9,018,411, which claims the benefit under 35 U.S.C. 119(e) of provisional application Ser. Nos. 61/267,399, filed on Dec. 7, 2009, and 61/291,224, filed on Dec. 30, 2009, the contents of all of which are incorporated by reference.

CONGESTIVE HEART FAILURE (CHF)

Congestive heart failure (CHF) is a generally progressive, life threatening condition in which myocardial contractility is depressed such that the heart is unable to adequately pump the blood returning to it, also referred to as decompensation. Symptoms include breathlessness, fatigue, weakness, leg swelling, and exercise intolerance. On physical examination, patients with heart failure often have elevated heart and respiratory rates (an indication of fluid in the lungs), edema, jugular venous distension, and/or enlarged hearts. The most common cause of CHF is atherosclerosis, which causes blockages in the coronary arteries that provide blood flow to the heart muscle. Ultimately, such blockages may cause myocardial infarction with subsequent decline in heart function and resultant heart failure. Other causes of CHF include valvular heart disease, hypertension, viral infections of the heart, alcohol consumption, and diabetes. Some cases of CHF occur without clear etiology and are called idiopathic. The effects of CHF on an individual experiencing the condition can be fatal.

There are several types of CHF. Two types of CHF are identified according to which phase of the cardiac pumping cycle is more affected. Systolic heart failure occurs when the heart's ability to contract decreases. The heart cannot pump with enough force to push a sufficient amount of blood into the circulation leading to a reduced left ventricular ejection fraction. Lung congestion is a typical symptom of systolic heart failure. Diastolic heart failure refers to the heart's inability to relax between contractions and allow enough blood to enter the ventricles. Higher filling pressures are required to maintain cardiac output, but contractility as measured by left ventricular ejection fraction is typically normal. Swelling (edema) in the abdomen and legs is a typical symptom of diastolic heart failure. Often, an individual experiencing heart failure will have some degree of both systolic heart failure and diastolic heart failure.

CHF is also classified according to its severity. The New York Heart Association classifies CHF into four classes: Class I involves no obvious symptoms, with no limitations on physical activity; Class II involves some symptoms during or after normal activity, with mild physical activity limitations; Class III involves symptoms with less than ordinary activity, with moderate to significant physical activity limitations; and Class IV involves significant symptoms at rest, with severe to total physical activity limitations. Typically, an individual progresses through the classes as they live with the condition.

Although CHF is generally thought of as a chronic, progressive condition, it can also develop suddenly. This type of CHF is called acute CHF, and it is a medical emergency. Acute CHF can be caused by acute myocardial injury that affects either myocardial performance, such as myocardial infarction, or valvular/chamber integrity, such as mitral regurgitation or ventricular septal rupture, which leads to an acute rise in left ventricular and diastolic pressure resulting in pulmonary edema and dyspnea.

Common treatment agents for CHF include vasodilators (drugs that dilate blood vessels), positive inotropes (drugs that increase the heart's ability to contract), and diuretics (drugs to reduce fluid). Additionally, beta-antagonists (drugs that antagonize beta-adrenergic receptors) have become standard agents for treating mild to moderate heart failure. Lowes et al., *Clin. Cardiol.* 2000, 23, III, 1-6.

Positive inotropic agents include beta-adrenergic agonists, such as dopamine, dobutamine, dopexamine, and isoproterenol. However, use of a beta-agonist has potential complications, such as arrhythmogenesis and increased oxygen demand by the heart. Additionally, the initial short-lived improvement of myocardial contractility afforded by these drugs is followed by an accelerated mortality rate resulting largely from a greater frequency of sudden death. Katz, *Heart Failure: Pathophysiology, Molecular Biology And Clinical Management* 1999, Lippincott, Williams & Wilkins.

Beta-antagonists antagonize beta-adrenergic receptor function. While initially contra-indicated in heart failure, they have been found to provide a marked reduction in mortality and morbidity in clinical trials. Bouzamondo et al., *Fundam. Clin. Pharmacol.* 2001, 15, 95-109. Accordingly, they have become an established therapy for heart failure. However, even individuals that improve under beta-antagonist therapy may subsequently decompensate and require acute treatment with a positive inotropic agent. Unfortunately, as their name suggests, beta-antagonists block the mechanism of action of the positive inotropic beta-agonists that are used in emergency care centers. Bristow et al., *J. Card. Fail.* 2001, 7, 8-12.

Vasodilators, such as nitroglycerin, have been used for a long period of time to treat heart failure. However, the cause of nitroglycerin's therapeutic effect was not known until late in the last century when it was discovered that the nitric oxide molecule (NO) was responsible for nitroglycerin's beneficial effects. In some individuals experiencing heart failure, a nitric oxide donor is administered in combination with a positive inotropic agent to both cause vasodilation and to increase myocardial contractility. However, this combined administration can impair the effectiveness of positive inotropic treatment agents. For example, Hart et al, *Am. J. Physiol. Heart Circ. Physiol.* 2001, 281, 146-54, reported that administration of the nitricoxide donor sodium nitroprusside, in combination with the positive inotropic, beta-adrenergic agonist dobutamine, impaired the positive inotropic effect of dobutamine. Hare et al., *Circulation* 1995, 92, 2198-2203, also disclosed the inhibitory effect of nitric oxide on the effectiveness of dobutamine.

As described in U.S. Pat. No. 6,936,639, compounds that donate nitroxyl (HNO) under physiological conditions have both positive inotropic and lusotropic effects and offer significant advantages over existing treatments for failing hearts. Due to their concomitant positive inotropic/lusotropic action and unloading effects, nitroxyl donors were reported as helpful in treating cardiovascular diseases characterized by high resistive load and poor contractile performance. In particular, nitroxyl-donating compounds were reported as useful in the treatment of heart failure, including heart failure in individuals receiving beta-antagonist therapy.

Ischemia

Ischemia is a condition characterized by an interruption or inadequate supply of blood to tissue, which causes oxygen deprivation in the affected tissue. Myocardial ischemia is a condition caused by a blockage or constriction of one or more of the coronary arteries, such as can occur with atherosclerotic plaque occlusion or rupture. The blockade or constriction causes oxygen deprivation of the non-perfused tissue, which can cause tissue damage. Further, upon reperfusion with subsequent reoxygenation of the tissue, when the blood is able to flow again or the oxygen demand of the tissue subsides, additional injury can be caused by oxidative stress.

Ischemia/reperfusion injury refers to tissue damage caused by oxygen deprivation followed by reoxygenation. The effects of ischemia/reperfusion injury in an individual experiencing the condition can be fatal, particularly when the injury occurs in a critical organ such as the heart or brain.

Accordingly, compounds and compositions effective in preventing or protecting against ischemia/reperfusion injury would be useful pharmaceuticals. Compounds such as nitroglycerin have been used for a long period of time to help control vascular tone and protect against myocardial ischemia/reperfusion injury. It was discovered that the nitric oxide molecule was responsible for nitroglycerin's beneficial effects. This discovery prompted interest in medical uses for nitric oxide and investigations into related species such as nitroxyl. As reported in U.S. patent application Ser. No. 10/463,084 (U.S. Publication No. 2004/0038947), administration of a compound that donates nitroxyl under physiological conditions, prior to ischemia, can attenuate ischemia/reperfusion injury to tissues, for example, myocardial tissues. This beneficial effect was reported as a surprising result given that nitroxyl was previously reported to increase ischemia/reperfusion injury (see, Ma et al., *Proc. Nat'l Acad. Sci.* 1999, 96(25), 14617-14622, reporting that administration of Angeli's salt (a nitroxyl donor under physiological conditions) to anesthetized rabbits during ischemia and 5 minutes prior to reperfusion increased myocardial ischemia/reperfusion injury, and Takahira et al., *Free Radical Biology & Medicine* 2001, 31(6), 809-815, reporting that administration of Angeli's salt during ischemia and 5 minutes before reperfusion of rat renal tissue contributed to neutrophil infiltration into the tissue, which is believed to mediate ischemia/reperfusion injury). In particular, pre-ischemic administration of Angeli's salt and isopropylamine/NO has been reported to prevent or reduce ischemia/reperfusion injury.

Cancer

One of the challenges in developing anti-cancer drugs is to discover compounds that are selectively toxic to tumor cells over normal cells. It has been found that tumor tissues have an acidic microenvironment with a pH from 6.0 to 7.0, while the extra- and intracellular milieu of normal cells has a pH of 7.4. Angeli's salt has been reported to exhibit strong cytotoxicity to cancer cells in weakly acidic solutions, whereas no toxicity was observed at pH 7.4 (Stoyanovsky, D. A. et al. *J. Med. Chem.* 2004, 47, 210-217; and PCT Publication No. WO/2003/020221). In a subcutaneous xenograft model of pheochromocytoma, Angeli's salt was found to inhibit tumor growth at a dose that was nontoxic to nude mice. Nitroxyl derivatives that are not known to release HNO, such as ruboxyl, a nitroxyl analogue of daunorubicin, have been shown to be active against hepatic metastases from colorectal carcinoma (Sirovich, I. et al *Tumor Biol.* 1999, 20, 270-276).

Norris A. J. et al., *Intl. J. Cancer* 2008, 122, 1905-1910, reported that Angeli's salt inhibits the proliferation of cultured breast cancer cells and decreases tumor mass in a mouse xenograft model. Norris A. J. et al proposed that HNO released from Angeli's salt blocks glycolysis in cancer cells by inhibiting the enzyme glyceraldehyde 3-phosphate dehydrogenase (GAPDH), resulting in decreased levels of HIF-1α (hypoxia-inducible factor) protein and activity, lower VEGF (vascular endothelial growth factor) production, decreased tumor angiogenesis and an increase in apoptotic cells.

Pulmonary Hypertension

Pulmonary hypertension (PH) is a generic term for a group of conditions characterized by elevated blood pressure in the arteries of the lungs (pulmonary arteries). In patients with PH, characteristic changes occur within the pulmonary circulation. These changes include thickening of the linings and obstruction of the small pulmonary blood vessels. As a result of these changes, pressure in the pulmonary circulation rises, and resistance in the blood flowing through the vessels increases. This increased resistance puts a strain on the right side of the heart as it must work harder to pump blood to the lungs. This strain can cause the heart to enlarge. Eventually, heart failure can develop.

The World Health Organization (WHO) classification of PH[1], as updated in the 2008 $4^{th}$ World Conference in Dana Point, Calif., includes five groups: pulmonary arterial hypertension (PAH)(Group 1), PH owing to left heart disease (Group 2), PH owing to lung diseases and/or hypoxia (Group 3), chronic thromboembolic PH (Group 4), and PH with unclear multifactorial mechanisms (Group 5).

[1] The initial attempt to develop a classification for PH was undertaken during the WHO Conference on PH in 1973. Since then, the PH classification has been revised three times, first at the 1998 $2^{nd}$ World Symposium in Evian, France, then at the 2003 $3^{rd}$ World Symposium in Venice, Italy, and most recently at the 2008 4th World Symposium in Dana Point, Calif.

Notwithstanding the current WHO classification, some literature still refer to the older classification system of "primary" and "secondary" PH. Primary PH refers to idiopathic PH, while secondary PH refers to PH that develops from another medical condition. For example, under the older classification system, PH owing to left heart disease was classified as PH secondary to left heart disease.

Current therapies for PH include supplemental oxygen, diuretics, oral vasodilators such as calcium channel blockers, anticoagulants, inotropic agents, prostanoids, endothelin receptor antagonists, and phosphodiesterase type-5 inhibitors. While such therapies have met with some success, many PH patients fail to respond to these therapies.

Nitroxyl Donors

Due to its inherent reactivity, HNO must be generated in situ from donor compounds. To date, the vast majority of studies of the biological effect of HNO have used the donor sodium α-oxyhyponitrite ("Angeli's salt" or "AS"). However, the chemical stability of AS has made it unsuitable to develop as a therapeutic agent. Angeli's salt also releases nitrite, which possesses its own biological profile. N-hydroxybenzenesulfonamide ("Piloty's acid" or "PA") has previously been shown to be a nitroxyl donor only at high pH (>9) (Bonner, F. T. et al., *Inorg. Chem.* 1992, 31, 2514-2519). Under physiological conditions, PA has been shown to be a nitric oxide donor via an oxidative pathway (Zamora, R. et al., *Biochem. J.* 1995, 312, 333-339). PCT Patent Application Publication No. WO/2007/109175 describes N-hydroxylsulfonamide derivatives that donate nitroxyl under physiological conditions.

Acyloxy nitroso compounds have been reported to yield nitroxyl in situ when reacted with nucleophiles (Sha, X. et al., *J. Am. Chem. Soc.* 2006, 128, 9687-9692). Although Rehse et al., *Arch. Pharm. Med. Chem.* 1998, 331, 104-110, showed acyloxy nitroso compounds inhibit platelet aggregation and thrombus formation (indicative of NO release), they generate only small amounts (<1%) of NO and HNO under neutral conditions. International Patent Application Publication WO 2007/120839 describes conjugates of acyloxy nitroso compounds with non-steroidal anti-inflammatory drugs (NSAID) as nitroxyl donors for treating congestive heart failure.

Significant Medical Need

Despite efforts towards the development of new therapies for the treatment of the diseases and conditions described above, there remains a significant medical need for additional or alternative compounds that treat, prevent or delay the onset and/or development of these and related diseases or conditions. In particular, there remains a significant medical need for alternative or additional therapies for the treatment of diseases or conditions that are responsive to nitroxyl therapy. New compounds that donate nitroxyl under physiological conditions and methods of using compounds that donate nitroxyl under physiological conditions may thus find use as therapies for treating, preventing and/or delaying the onset and/or development of diseases or conditions responsive to nitroxyl therapy, including heart disease, ischemia/reperfusion injury and cancer. Preferably, the therapeutic agents can improve the quality of life and/or prolong the survival time for patients with the disease or condition.

DEFINITIONS

Figure 1:
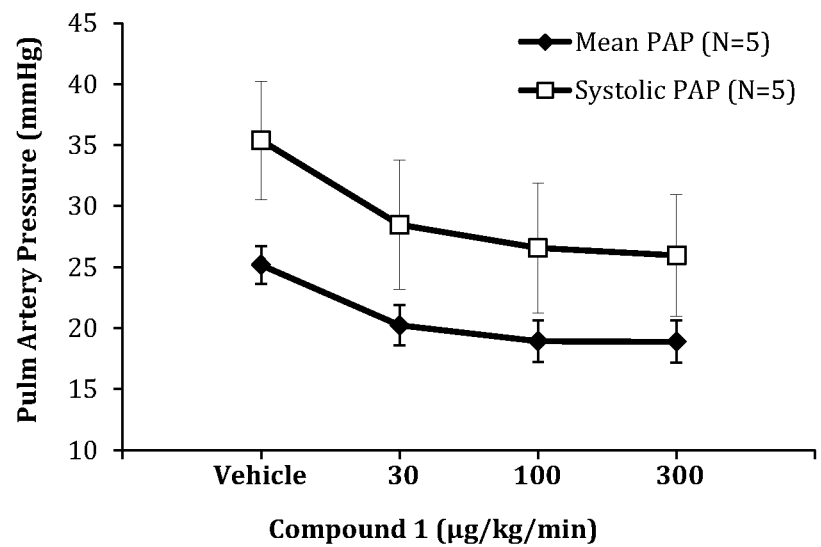
FIG. 1 shows the intravenous effects of a nitroxyl (HNO) donor on mean and systolic (peak) pulmonary artery pressure (PAP) in rats.

Unless clearly indicated otherwise, the following terms as used herein have the meanings indicated below.

"A", "an" and the like refers to one or more.

"Eq" or "equiv" or "equivalent" refers to molar equivalent.

"Hr" or "h" refers to hour.

"Min" or "m" refers to minute.

"Alkyl" intends linear hydrocarbon structures having 1 to 20 carbon atoms, 1 to 12 carbon atoms or 1 to 8 carbon atoms. Alkyl groups of fewer carbon atoms are embraced, such as so-called "lower alkyl" groups having 1 to 4 carbon atoms. "Alkyl" also intends branched or cyclic hydrocarbon structures having 3 to 20 carbon atoms, 3 to 12 carbon atoms and 3 to 8 carbon atoms. For any use of the term "alkyl," unless clearly indicated otherwise, it is intended to embrace all variations of alkyl groups disclosed herein, as measured by the number of carbon atoms, the same as if each and every alkyl group was explicitly and individually listed for each usage of the term. For instance, when a group such as $R^3$ may be an "alkyl," intended is a $C_1$-$C_{20}$ alkyl or a $C_1$-$C_{12}$ alkyl or a $C_1$-$C_8$ alkyl or a lower alkyl or a $C_2$-$C_{20}$ alkyl or a $C_3$-$C_{12}$ alkyl or a $C_3$-$C_8$ alkyl. The same is true for other groups listed herein, which may include groups under other definitions, where a certain number of atoms is listed in the definition. When the alkyl group is cyclic, it may also be referred to as a cycloalkyl group and have, for example, 1 to 20 annular carbon atoms, 1 to 12 annular carbon atoms and 1 to 8 annular carbon atoms. When an alkyl residue having a specific number of carbons is named, all geometric isomers having that number of carbons are intended to be encompassed; thus, for example, "butyl" is meant to include n-butyl, sec-butyl, iso-butyl and t-butyl; "propyl" includes n-propyl and iso-propyl. Examples of alkyl groups include methyl, ethyl, n-propyl, i-propyl, t-butyl, n-heptyl, octyl, cyclopentyl, cyclopropyl, cyclobutyl, norbornyl, and the like.

"Substituted alkyl" refers to an alkyl group having from 1 to 5 substituents. For instance, an alkyl group substituted with a group such as halo, nitro, cyano, oxo, aryl, alkoxy, acyl, acylamino, amino, hydroxyl, carboxyl, carboxylalkyl, thiol, thioalkyl, heterocyclyl, —OS(O)$_2$-alkyl, and the like is a substituted alkyl. Likewise, "substituted alkenyl" and "substituted alkynyl" refer to alkenyl or alkynyl groups having 1 to 5 substituents.

"Substituted" means that a hydrogen radical on a compound or group (such as, for example, alkyl, substituted alkyl, alkenyl, substituted alkenyl, alkynyl, substituted alkynyl, aryl, substituted aryl, aralkyl, substituted aralkyl, heteroaryl, substituted heteroaryl, heteroaralkyl, substituted heteroaralkyl, cycloalkyl, substituted cycloalkyl, heterocycloalkyl, substituted heterocycloalkyl, heterocyclyl and substituted heterocyclyl) is replaced with a group (the "substituent") that does not substantially adversely affect the stability of the compound. In some embodiments, the substituents are those which do not adversely affect the activity of a compound. The term "substituted" refers to one or more substituents (which may be the same or different), each replacing a hydrogen atom. Examples of substituents include, but are not limited to, halo (F, Cl, Br, or I), hydroxyl, amino, alkylamino, arylamino, dialkylamino, diarylamino, cyano, nitro, mercapto, oxo, carbonyl, thio, imino, formyl, carbamido, carbamyl, carboxyl, thioureido, thiocyanato, sulfoamido, sulfonylalkyl, sulfonylaryl, alkyl, alkenyl, alkoxy, mercaptoalkoxy, aryl, heteroaryl, cyclyl, heterocyclyl, wherein alkyl, alkenyl, alkyloxy, aryl, heteroaryl, cyclyl, and heterocyclyl are optionally substituted with alkyl, aryl, heteroaryl, halogen, hydroxyl, amino, mercapto, cyano, nitro, oxo (=O), thioxo (=S), or imino (=Nalkyl). In some embodiments, substituents on any group (such as, for example, alkyl, substituted alkyl, alkenyl, substituted alkenyl, alkynyl, substituted alkynyl, aryl, substituted aryl, aralkyl, substituted aralkyl, heteroaryl, substituted heteroaryl, heteroaralkyl, substituted heteroaralkyl, cycloalkyl, substituted cycloalkyl, heterocycloalkyl, substituted heterocycloalkyl, heterocyclyl and substituted heterocyclyl) are at any atom of that group (such as on a carbon atom of the primary carbon chain of a substituted alkyl group or on a substituent already present on a substituted alkyl group), wherein any group that can be substituted (such as, for example, alkyl, alkenyl, alkynyl, aryl, aralkyl, heteroaryl, heteroaralkyl, cycloalkyl, cyclyl, heterocycloalkyl, and heterocyclyl) can be optionally substituted with one or more substituents (which may be the same or different), each replacing a hydrogen atom. Examples of substituents include, but not limited to alkyl, alkenyl, alkynyl, cyclyl, cycloalkyl, heterocyclyl, heterocycloalkyl, aralkyl, heteroaralkyl, aryl, heteroaryl, halo, haloalkyl, cyano, nitro, alkoxy, aryloxy, hydroxyl, hydroxylalkyl, oxo, carbonyl, carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, or alkoxycarbonylamino; alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, or mercaptoalkoxy. Additional examples of substituents include, without limitation, halo, CN, NO$_2$, OR$^{11}$, SR$^{11}$, S(O)$_2$OR$^{11}$, NR$^{11}$R$^{12}$, C$_1$-C$_2$ perfluoroalkyl, C$_1$-C$_2$ perfluoroalkoxy, 1,2-methylenedioxy, (=O), (=S), (=NR$^{11}$), O(CH$_2$)$_n$OR$^{11}$, C(O)R$^{11}$, C(O)OR$^{11}$, C(OR$^{11}$)R$^{12}$, C(O)NR$^{11}$R$^{12}$, OC(O)R$^{13}$, OC(O)NR$^{11}$R$^{12}$, NR$^{11}$C(O)NR$^{11}$R$^{12}$, C(NR$^{12}$)NR$^{11}$R$^{12}$, NR$^{11}$C(NR$^{12}$)NR$^{11}$)NR$^{12}$, S(O)$_2$NR$^{11}$R$^{12}$R$^{13}$, C(O)H, C(O)R$^{13}$, NR$^{11}$C(O)R$^{13}$, NR$^{11}$C(O)OR$^{13}$, Si(R$^{11}$)$_3$, OSi(R$^{11}$)$_3$, Si(OH)$_2$R$^{11}$, B(OH)$_2$, P(O)(OR$^{11}$)$_2$, S(O)R$^{13}$, and S(O)$_2$R$^{13}$. Each R$^{11}$ is independently hydrogen, C$_1$-C$_6$ alkyl optionally substituted with alkoxy, cycloalkyl, aryl, heterocyclyl, or heteroaryl. Each R$^{12}$ is independently hydrogen, C$_3$-C$_6$ cycloalkyl, aryl, heterocyclyl, heteroaryl, C$_1$-C$_4$ alkyl or C$_1$-C$_4$ alkyl substituted with C$_3$-C$_6$ cycloalkyl, aryl, heterocyclyl or heteroaryl. Each R$^{13}$ is independently C$_3$-C$_6$ cycloalkyl, aryl, heterocyclyl, heteroaryl, C$_1$-C$_4$ alkyl or C$_1$-C$_4$ alkyl substituted with C$_3$-C$_6$ cycloalkyl, aryl, heterocyclyl or heteroaryl. Each C$_3$-C$_6$ cycloalkyl, aryl, heterocyclyl, heteroaryl and C$_1$-C$_4$ alkyl in each R$^{11}$, R$^{12}$ and R$^{13}$ can optionally be substituted with halo, CN, C$_1$-C$_4$ alkyl, OH, C$_1$-C$_4$ alkoxy, COOH, C(O)OC$_1$-C$_4$ alkyl, NH$_2$, C$_1$-C$_4$ alkylamino, or C$_1$-C$_4$ dialkylamino. Each n is an integer from 1 to 6. Substituents can also be "electron-withdrawing groups."

"Alkenyl" refers to a group of 2 or more carbon atoms, such as 2 to 10 carbon atoms and 2 to 6 carbon atoms, and having at least one double bond. Examples of an alkenyl group include —C=CH2, —CH2CH=CHCH3 and —CH2CH=CH—CH=CH2.

"Alkynyl" refers to group having 2 or more carbon atoms, such as 2 to 10 carbon atoms and 3 to 6 carbon atoms, and having at least one triple bond, such as the moiety —C≡CH.

"Heterocyclyl" or "heterocycloalkyl" refers to a cycloalkyl residue in which one to four of the carbons is replaced by a heteroatom such as oxygen, nitrogen or sulfur. Examples of heterocycles whose radicals are heterocyclyl groups include tetrahydropyran, morpholine, pyrrolidine, piperidine, thiazolidine, oxazole, oxazoline, isoxazole, dioxane, tetrahydrofuran and the like. A specific example of a heterocyclyl residue is tetrahydropyran-2-yl.

"Substituted heterocyclyl" or "substituted heterocylcoalkyl" refers to an heterocyclyl group having from 1 to 5 substituents. For instance, a heterocyclyl group substituted with 1 to 5 groups such as halo, nitro, cyano, oxo, aryl, alkoxy, alkyl, acyl, acylamino, amino, hydroxyl, carboxyl, carboxyalkyl, thiol, thioalkyl, heterocyclyl, —OS(O)$_2$-alkyl, and the like is a substituted alkyl. A particular example of a substituted heterocylcoalkyl is N-methylpiperazino.

"Aryl" refers to a monocyclic, bicyclic or tricyclic aromatic ring radical. In some embodiments, an aryl group is a 5- or 6-membered aromatic ring containing; a bicyclic 9- or 10-membered aromatic ring system (meaning the ring system has 9 or 10 annular atoms); or a tricyclic 13- or 14-membered aromatic ring system (meaning the ring system has 13 or 14 annular atoms). Examples of aryl radicals include, for example, phenyl, naphthalenyl, indanyl and tetralinyl.

"Substituted aryl" refers to a group having from 1 to 3 substituents. For instance, an aryl group substituted with 1 to 3 groups, such as halo, nitro, cyano, oxo, aryl, alkoxy, alkyl, acyl, acylamino, amino, hydroxyl, carboxyl, carboxylalkyl, thiol, thioalkyl, heterocyclyl, —OS(O)$_2$-alkyl and the like, is a substituted aryl.

"Aralkyl" refers to a residue in which an aryl moiety is attached to the parent structure via an alkyl residue. Examples include benzyl (—CH$_2$-Ph), phenethyl (—CH$_2$CH$_2$Ph), phenylvinyl (—CH=CH-Ph), phenylallyl and the like.

"Heteroaryl" refers to an aromatic ring system having at least one annular heteroatom selected from O, N, or S. An heteroaryl group is preferably a 5- or 6-membered aromatic ring containing 1-3 annular heteroatoms selected from O, N, or S; a bicyclic 9- or 10-membered aromatic ring system (meaning the ring system has 9 or 10 annular atoms) containing 1-3 annular heteroatoms selected from O, N, or S; or a tricyclic 13- or 14-membered aromatic ring system (meaning the ring system has 13 or 14 annular atoms) containing 1-3 annular heteroatoms selected from O, N, or S. Examples of groups whose radicals are heteroaryl groups include e.g., imidazole, pyridine, indole, thiophene, benzopyranone, thiazole, furan, benzimidazole, benzoxazole, benzthiazole, quinoline, isoquinoline, quinoxaline, pyrimidine, pyrazine, tetrazole and pyrazole.

"Alkoxy" refers to an alkyl group that is connected to the parent structure through an oxygen atom (—O-alkyl). When a cycloalkyl group is connected to the parent structure through an oxygen atom, the group may also be referred to as a cycloalkoxy group. Examples include methoxy, ethoxy, propoxy, isopropoxy, cyclopropyloxy, cyclohexyloxy and the like. When the cycloalkyl group contains one or more heteroatoms, the group may also be referred to as "heterocycloalkoxy" group. Examples of heteroatoms include O, S, N, P, Se, Si and the like. A "perhaloalkoxy" intends a perhaloalkyl group attached to the parent structure through an oxygen, such as the residue —O—CF$_3$.

"Aryloxy" refers to an aryl group that is connected to the parent structure through an oxygen atom (—O-aryl), which by way of example includes the residues phenoxy, naphthoxy, and the like. "Substituted aryloxy" refers to a substituted aryl group connected to the parent structure through an oxygen atom (—O-substituted aryl).

"Electron withdrawing group" refers to a group that reduces electron density of the moiety to which it is attached (relative to the density of the moiety without the substituent). Examples include, without limitation, F, Cl, Br, I, —CN, —CF$_3$, —NO$_2$, —SH, —C(O)H, —C(O)alkyl, —C(O)Oalkyl, —C(O)OH, —C(O)Cl, —S(O)$_2$OH, —S(O)$_2$NHOH, —NH$_3$ and the like.

"Halo" refers to fluoro, chloro, bromo or iodo.

"Alkylsulfonyl" refers to groups —SO$_2$alkyl and —SO$_2$substituted alkyl, which includes the residues —SO$_2$cycloalkyl, —SO$_2$substituted cycloalkyl, —SO$_2$alkenyl, —SO$_2$substituted alkenyl, —SO$_2$alkynyl, —SO$_2$substituted alkynyl, where alkyl, substituted alkyl, alkenyl, substituted alkenyl, alkynyl, substituted alkynyl, cycloalkyl and substituted cycloalkyl are as defined herein.

"N-hydroxylsulfonamidyl" refers to —S(O)$_2$NROH, where R is H or alkyl.

"Perhaloalkyl" refers to an alkyl group where each H of the hydrocarbon is replaced with F. Examples of perhalo groups include —CF$_3$ and —CF$_2$CF$_3$.

"Alkylsulfanyl" refers to an alkyl group that is connected to the parent structure through a sulfur atom (—S-alkyl) and refers to groups —S-alkyl and —S-substituted alkyl, which include the residues —S-cycloalkyl, —S-substituted cycloalkyl, —S-alkenyl, —S-substituted alkenyl, —S—alkynyl, and —S-substituted alkynyl, where alkyl, substituted alkyl, alkenyl, substituted alkenyl, alkynyl, substituted alkynyl, cycloalkyl and substituted cycloalkyl are as defined herein. When a cycloalkyl group is connected to the parent structure through an sulfur atom, the group may also be referred to as a cycloalkylsulfanyl group. By way of example, alkylsulfanyl includes —S—CH(CH$_3$), —S—CH$_2$CH$_3$ and the like.

"Alkylsulfinyl" refers to an alkyl group that is connected to the parent structure through a S(O) moiety and refers to groups —S(O)alkyl and —S(O)substituted alkyl, which includes the residues —S(O)cycloalkyl, —S(O)substituted cycloalkyl, —S(O)alkenyl, —S(O)substituted alkenyl, —S(O)alkynyl, —S(O)substituted alkynyl, where alkyl, substituted alkyl, alkenyl, substituted alkenyl, alkynyl, substituted alkynyl, cycloalkyl and substituted cycloalkyl are as defined herein. By way of example, alkylsulfinyl includes the residues —S(O)CH(CH$_3$), —S(O)CH$_3$, —S(O)cyclopentane and the like.

"Arylsulfinyl" refers to an aryl group that is connected to the parent structure through a S(O) moiety, which by way of example includes the residue —S(O)Ph.

"Acyl" refers to and includes the groups —C(O)H, —C(O)alkyl, —C(O)substituted alkyl, —C(O)alkenyl, —C(O)substituted alkenyl, —C(O)alkynyl, —C(O)substituted alkynyl, —C(O)cycloalkyl, —C(O)substituted cycloalkyl, —C(O)aryl, —C(O)substituted aryl, —C(O)heteroaryl, —C(O)substituted heteroaryl, —C(O)heterocyclic, and —C(O)substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein or otherwise known in the art.

"Dialkylamino" refers to the group —NR$_2$ where each R is an alkyl group. Examples of dialkylamino groups include —N(CH$_3$)$_2$, —N(CH$_2$CH$_2$CH$_2$CH$_3$)$_2$, and N(CH$_3$)(CH$_2$CH$_2$CH$_2$CH$_3$).

"Optional" or "optionally" means that the subsequently described event or circumstance may or may not occur, and that the description includes instances where the event or circumstance occurs and instances in which it does not. For example, an alkyl that is "optionally substituted" encompasses both an alkyl that is unsubstituted and an alkyl that is substituted.

"Pharmaceutically acceptable" refers to those properties and/or substances that are acceptable to the patient from a pharmacological and/or toxicological point of view, and/or to the manufacturing pharmaceutical chemist from a physical and/or chemical point of view regarding composition, formulation, stability, patient acceptance, bioavailability and compatibility with other ingredients.

"Pharmaceutically acceptable salt" refers to pharmaceutically acceptable salts of a compound described herein, such as a compound of formula (I), (Ia) or (II) or other nitroxyl donors, which salts may be derived from a variety of organic and inorganic counter ions well known in the art and include, by way of example, sodium, potassium, calcium, magnesium, ammonium, tetraalkylammonium, and the like; when the molecule contains a basic functionality, salts of organic or inorganic acids, such as hydrochloride, hydrobromide, tartrate, mesylate, acetate, maleate, oxalate and the like. Illustrative salts include, but are not limited, to sulfate, citrate, acetate, chloride, bromide, iodide, nitrate, bisulfate, phosphate, acid phosphate, lactate, salicylate, acid citrate, tartrate, oleate, tannate, pantothenate, bitartrate, ascorbate, succinate, maleate, besylate, fumarate, gluconate, glucaronate, saccharate, formate, benzoate, glutamate, methanesulfonate, ethanesulfonate, benzenesulfonate, and p-toluenesulfonate salts. Accordingly, a salt may be prepared from a compound of any one of the formulae disclosed herein having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethyl) amine; N-methyl-D-glucamine; and amino acids such as arginine, lysine, and the like. A salt may also be prepared from a compound of any one of the formulae disclosed herein having a basic functional group, such as an amino functional group, and a pharmaceutically acceptable inorganic or organic acid. Suitable acids include hydrogen sulfate, citric acid, acetic acid, hydrochloric acid (HCl), hydrogen bromide (HBr), hydrogen iodide (HI), nitric acid, phosphoric acid, lactic acid, salicylic acid, tartaric acid, ascorbic acid, succinic acid, maleic acid, besylic acid, fumaric acid, gluconic acid, glucaronic acid, formic acid, benzoic acid, glutamic acid, methanesulfonic acid, ethanesulfonic acid, benzenesulfonic acid, and p-toluenesulfonic acid.

"Pharmaceutically acceptable excipient" refers to any substance, not itself a therapeutic agent, used as a carrier, diluent, adjuvant, binder, and/or vehicle for delivery of a therapeutic agent to a patient, or added to a pharmaceutical composition to improve its handling or storage properties or to permit or facilitate formation of a compound or composition into a unit dosage form for administration. Pharmaceutically acceptable excipients are well known in the pharmaceutical arts and are described, for example, in Remington's Pharmaceutical Sciences, Mack Publishing Co., Easton, Pa. (e.g., 20$^{th}$ Ed., 2000), and Handbook of Pharmaceutical Excipients, American Pharmaceutical Association, Washington, D.C., (e.g., 1$^{st}$, 2$^{nd}$ and 3$^{rd}$ Eds., 1986, 1994 and 2000, respectively). As will be known to those skilled in the art, pharmaceutically acceptable excipients may provide a variety of functions and may be described as wetting agents, buffering agents, suspending agents, lubricating agents, emulsifiers, disintegrants, absorbents, preservatives, surfactants, colorants, flavorants, and sweeteners. Examples of pharmaceutically acceptable excipients include without limitation: (1) sugars, such as lactose, glucose and sucrose; (2) starches, such as corn starch and potato starch; (3) cellulose and its derivatives, such as sodium carboxymethyl cellulose, ethyl cellulose, cellulose acetate, hydroxypropylmethylcellulose, and hydroxypropylcellulose; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

"Unit dosage form" refers to a physically discrete unit suitable as a unitary dosage for human or other animal patients. Each unit dosage form may contain a predetermined amount of an active substance (e.g., a compound of formula (I), (Ia) or (II)) calculated to produce a desired effect.

Unless clearly indicated otherwise, an "individual" or "patient" refers to an animal, such as a mammal, including but not limited, to a human. Hence, the methods described herein can be useful in human therapy and veterinary applications. In some embodiments, the individual or patient is a mammal. In some embodiments, the individual or patient is a human.

"Effective amount" refers to such amount of a compound or a pharmaceutically acceptable salt thereof, which in combination with its parameters of efficacy and toxicity, as well as based on the knowledge of the practicing specialist should be effective in a given therapeutic form. As is understood in the art, an effective amount may be in one or more doses.

"Treatment" or "treating" is an approach for obtaining a beneficial or desired result, including clinical results. For purposes of this invention, beneficial or desired results include but are not limited to inhibiting and/or suppressing the onset and/or development of a disease or condition or reducing the severity of such disease or condition, such as reducing the number and/or severity of symptoms associated with the disease or condition, increasing the quality of life of those suffering from the disease or condition, decreasing the dose of other medications required to treat the disease or condition, enhancing the effect of another medication an individual is taking for the disease or condition, and prolonging survival of individuals having the disease or condition.

"Preventing" refers to reducing the probability of developing a disorder or condition in an individual who does not have, but is at risk of developing a disorder or condition. An individual "at risk" may or may not have a detectable disease or condition, and may or may not have displayed a detectable disease or condition prior to the treatment methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s).

"Nitroxyl" refers to the species HNO.

"Nitroxyl donor" or "HNO donor" refers to a compound that donates nitroxyl under physiological conditions. As used herein, nitroxyl donors may alternatively be referred to as "a compound" or "the compound." In some embodiments, the nitroxyl donor is capable of donating an effective amount of nitroxyl in vivo and has a safety profile indicating the compound would be tolerated by an individual in the amount necessary to achieve a therapeutic effect. One of ordinary skill in the art would be able to determine the safety of administering particular compounds and dosages to live subjects. One of skill in the art may also determine whether a compound is a nitroxyl donor by evaluating whether it releases HNO under physiological conditions. Compounds are easily tested for nitroxyl donation with routine experiments. Although it is impractical to directly measure whether nitroxyl is donated, several tests are accepted for determining whether a compound donates nitroxyl. For example, the compound of interest can be placed in solution, for example in phosphate buffered saline (PBS) or phosphate buffered solution at a pH of about 7.4, in a sealed container. After sufficient time for disassociation has elapsed, such as from several minutes to several hours, the headspace gas is withdrawn and analyzed to determine its composition, such as by gas chromatography and/or mass spectroscopy. If the gas $N_2O$ is formed (which occurs by HNO dimerization), the test is positive for nitroxyl donation and the compound is a nitroxyl donor. The level of nitroxyl donating ability may be expressed as a percentage of a compound's theoretical maximum. A compound that donates a "significant level of nitroxyl" intends a compound that donates 40% or more or 50% or more of its theoretical maximum amount of nitroxyl. In some embodiments, the compounds for use herein donate 60% or more of the theoretical maximum amount of nitroxyl. In some embodiments, the compounds for use herein donate 70% or more of the theoretical maximum amount of nitroxyl. In some embodiments, the compounds for use herein donate 80% or more of the theoretical maximum amount of nitroxyl. In some embodiments, the compounds for use herein donate 90% or more of the theoretical maximum amount of nitroxyl. In some embodiments, the compounds for use herein donate between about 70% and about 90% of the theoretical maximum amount of nitroxyl. In some embodiments, the compounds for use herein donate between about 85% and about 95% of the theoretical maximum amount of nitroxyl. In some embodiments, the compounds for use herein donate between about 90% and about 95% of the theoretical maximum amount of nitroxyl. Compounds that donate less than 40% or less than 50% of their theoretical amount of nitroxyl are still nitroxyl donors and may be used in the invention disclosed herein. A compound that donates less than 50% of the theoretical amount of nitroxyl may be used in the methods described, and may require higher dosing levels as compared to compounds that donate a significant level of nitroxyl. Nitroxyl donation also can be detected by exposing the test compound to metmyoglobin ($Mb^{3+}$). Nitroxyl reacts with $Mb^{3+}$ to form an $Mb^{2+}$—NO complex, which can be detected by changes in the ultraviolet/visible spectrum or by Electron Paramagnetic Resonance (EPR). The $Mb^{2+}$—NO complex has an EPR signal centered around a g-value of about 2. Nitric oxide, on the other hand, reacts with $Mb^{3+}$ to form an $Mb^{3+}$—NO complex that is EPR silent. Accordingly, if the candidate compound reacts with $Mb^{3+}$ to form a complex detectable by common methods, such as ultraviolet/visible or EPR, then the test is positive for nitroxyl donation. Testing for nitroxyl donation may be performed at physiologically relevant pH. Examples of nitroxyl donors include, without limitation, sodium dioxotrinitrate ("Angeli's salt" or "AS"), N-hydroxybenzenesulfonamide ("Piloty's acid" or "PA"), and the compounds disclosed in U.S. Pat. No. 6,936,639, US Patent Publication Nos. 2004/0038947, 2007/0299107 and 2009/0163487, and PCT Publication Nos. WO/2007/002444, WO/2005/074598 and WO/2009/137717, the entire disclosures of which patents and publications are herein incorporated by reference.

"Positive inotrope" refers to an agent that causes an increase in myocardial contractile function. Such an agent includes a beta-adrenergic receptor agonist, an inhibitor of phosphodiesterase activity, and calcium-sensitizers. Beta-adrenergic receptor agonists include, among others, dopamine, dobutamine, terbutaline, and isoproterenol. Analogs and derivatives of such compounds are also intended. For example, U.S. Pat. No. 4,663,351 describes a dobutamine prodrug that can be administered orally. One of ordinary skill in the art would be able to determine if a compound is capable of causing positive inotropic effects and also additional beta-agonist compounds. In particular embodiments, the beta-receptor agonist is selective for the beta-1 receptor. In other embodiments the beta-agonist is selective for the beta-2 receptor, or is not selective for any particular receptor.

Diseases or conditions that are "responsive to nitroxyl therapy" includes any disease or condition in which administration of a compound that donates an effective amount of nitroxyl under physiological conditions treats and/or prevents the disease or condition, as those terms are defined herein. A disease or condition whose symptoms are suppressed or diminished upon administration of nitroxyl donor is a disease or condition responsive to nitroxyl therapy. Nonlimiting examples of diseases or conditions that are responsive to nitroxyl therapy include coronary obstructions, coronary artery disease (CAD), angina, heart attack, myocardial infarction, high blood pressure, ischemic cardiomyopathy and infarction, diastolic heart failure, pulmonary congestion, pulmonary edema, cardiac fibrosis, valvular heart disease, pericardial disease, circulatory congestive states, peripheral edema, ascites, Chagas' disease, ventricular hypertrophy, heart valve disease, heart failure, including but not limited to congestive heart failure such as acute congestive heart failure and acute decompensated heart failure. Other cardiovascular diseases or conditions are also intended, as are diseases or conditions that implicate ischemia/reperfusion injury. Cancer is another example of disease or condition that is responsive to nitroxyl therapy.

"Pulmonary hypertension" or "PH" refers to a condition in which the pulmonary arterial pressure is elevated. The current haemodynamic definition of PH is a mean pulmonary arterial pressure (MPAP) at rest of greater than or equal to 25 mmHg.[2] Examples of PH include, but are not limited to, the conditions listed in the updated classification of PH (Table 1).[3]

[2] Badesch D. et al. Diagnosis and assessment of pulmonary arterial hypertension. J Am Coll Cardiol 2009; 54(Suppl.): S55-S66.
[3] Simonneau G. et al. Updated clinical classification of pulmonary hypertension. J Am Coll Cardiol 2009; 54(1 Suppl): S43-54.

TABLE 1

Classification of Pulmonary Hypertension (PH):

1. Pulmonary artery hypertension (PAH)
    1.1. Idiopathic PAH
    1.2. Heritable
        1.2.1. BMPR2
        1.2.2. ALK1, endoglin (with or without hereditary hemorrhagic telangiectasia
        1.2.3. Unknown
    1.3. Drug-and toxin-induced
    1.4. Associated with:
        1.4.1. Connective tissue diseases
        1.4.2. Human immunodeficiency virus (HIV) infection
        1.4.3. Portal hypertension
        1.4.4. Congenital heart diseases
        1.4.5. Schistosomiasis
    1.5 Persistent pulmonary hypertension of the newborn
    1'. Pulmonary veno-occlusive disease (PVOD) and/or pulmonary capillary hemangiomatosis (PCH)
2. Pulmonary hypertension owing to left heart disease
    2.1. Systolic dysfunction
    2.2. Diastolic dysfunction
    2.3. Valvular disease
3. Pulmonary hypertension owing to lung disease and/or hypoxemia
    3.1. Chronic obstructive pulmonary disease
    3.2. Interstitial lung disease
    3.3. Other pulmonary diseases with mixed restrictive and obstructive pattern
    3.4. Sleep-disordered breathing
    3.5. Alveolar hypoventilation disorders
    3.6. Chronic exposure to high altitude
    3.7. Developmental abnormalities TABLE 1-continued Classification of Pulmonary Hypertension (PH):

4. Chronic thromboembolic pulmonary hypertension (CTEPH)
5. Pulmonary hypertension with unclear multifactorial mechanisms
    5.1. Hematologic disorders: myeoloproliferative disorders, splenectomy
    5.2. Systemic disorders: sarcoidosis, pulmonary Langerhans cell histiocytosis: lymphangioleiomyomatosis, neurofibromatosis, vasculitis
    5.3. Metabolic disorders: glycogen storage disease, Gaucher disease, thyroid disorders
    5.4. Others: tumoral obstruction, fibrosing mediastinitis, chronic renal failure on dialysis The invention provides certain bis-acylated hydroxylamine derivative compounds, methods of using such compounds, and pharmaceutical compositions and kits comprising such compounds.

In some embodiments, the invention provides a compound of formula (I)

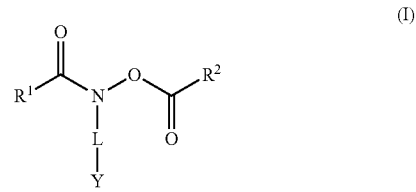

or a pharmaceutically acceptable salt, hydrate, or solvate thereof wherein:

L is a bond, —$SO_2$— or —O—;

Y is alkyl, aryl, heteroaryl or benzyl, wherein said alkyl, aryl, heteroaryl and benzyl are substituted with one or more substituents independently selected from W;

W is halo, —CN, —$NO_2$, —$COR^3$, —$COOR^3$, —$CONR^3R^4$, —$CH(C(O)R^3)_2$, —$SO_2R^3$ or —COX, wherein X is halo, and $R^3$ and $R^4$ are independently alkyl or aryl, or $R^3$ and $R^4$ are taken together to form a cycloalkyl or heterocycloalkyl, wherein said cycloalkyl and heterocycloalkyl are unsubstituted or substituted with one or more substituents;

$R^1$ and $R^2$ are independently hydrogen, alkyl, heterocycloalkyl, aryl, benzyl, alkoxy, aryloxy, benzyloxy, —$NR_5R^6$, —$N(OR^5)R^6$, —$NR^5C(O)R^6$ or —O-heterocycloalkyl, wherein said alkyl, heterocycloalkyl, aryl, benzyl, alkoxy, aryloxy, benzyloxy, —$N(OR^5)R^6$, —$NR^5C(O)R^6$ and —O-heterocycloalkyl are unsubstituted or substituted with one or more substituents; and $R^5$ and $R^6$ are independently alkyl or aryl, where said alkyl and aryl are unsubstituted or substituted with one or more substituents.

In some embodiments, L is a bond, —$SO_2$— or —O—; Y is alkyl, or aryl, wherein said alkyl and aryl are substituted with one or more substituents independently selected from W; W is halo, —CN, —$NO_2$, —$COR^3$, —$COOR^3$, —$CONR^3R^4$, —$CH(C(O)R^3)_2$, —$SO_2R^3$ or —COX, wherein X is halo, and $R^3$ and $R^4$ are independently alkyl or aryl, or $R^3$ and $R^4$ are taken together to form a cycloalkyl or heterocycloalkyl, wherein said cycloalkyl and heterocycloalkyl are unsubstituted or substituted with one or more substituents; $R^1$ and $R^2$ are independently hydrogen, alkyl, heterocycloalkyl, aryl, benzyl, alkoxy, aryloxy, benzyloxy or —$NR^5R^6$, wherein said alkyl, heterocycloalkyl, aryl, benzyl, alkoxy, aryloxy and benzyloxy are unsubstituted or substituted with one or more substituents; and $R^5$ and $R^6$ are independently alkyl or aryl.

In some embodiments, when L is —$SO_2$—, $R^2$ is phenyl or alkyl, and Y is phenyl substituted with one substituent selected from W, then W is not 4-chloro or 4-nitro; and when L is —$SO_2$—, $R^2$ is alkyl, and Y is phenyl substituted with two or three substituents independently selected from W, then two of the substituents are not 3-nitro and 5-nitro.

Included in any of the embodiments disclosed above are the following additional embodiments which may be combined in any variation.

In some embodiments, L is —$SO_2$—.

In some embodiments, Y is aryl substituted with one or more substituents independently selected from W.

In some embodiments, Y is aryl substituted with one, two or three substituents independently selected from W.

In some embodiments, Y is phenyl substituted with one or more substituents independently selected from W.

In some embodiments, Y is heteroaryl, wherein said heteroaryl is unsubstituted or substituted with one or more substituents independently selected from W.

In some embodiments, Y is benzyl wherein said benzyl is substituted with one or more substituents independently selected from W.

In some embodiments, W is halo, —$SO_2R^3$ or —$NO_2$.

In some embodiments, W is chloro, bromo, fluoro or —$NO_2$.

In some embodiments, $R^1$ and $R^2$ are independently alkyl, heterocycloalkyl, alkoxy, phenyl, benzyl or benzyloxy, wherein said alkyl, heterocycloalkyl, alkoxy, phenyl, benzyl and benzyloxy are unsubstituted or substituted with one or more substituents independently selected from halo, alkyl, nitro, alkylsulfonyl, trihalomethyl, phenyl, —$C(O)OR^{11}$, —$C(O)R^{13}$, —$OC(O)R^{13}$, —$NRR^{12}$, —$NR^{11}C(O)R^{13}$ and —$OR^{11}$.

In some embodiments, $R^1$ and $R^2$ are independently alkyl, heterocycloalkyl, alkoxy, phenyl or benzyloxy, wherein said alkyl, heterocycloalkyl, alkoxy, phenyl, and benzyloxy are unsubstituted or substituted with one or more substituents independently selected from halo, alkyl, nitro, alkylsulfonyl and trihalomethyl.

In some embodiments, $R^{11}$ is $C_1$-$C_6$ alkyl optionally substituted with alkoxy.

In some embodiments, $R^{12}$ is $C_1$-$C_4$ alkyl.

In some embodiments, $R^{13}$ is $C_1$-$C_4$ alkyl.

In some embodiments, $R^5$ and $R^6$ are independently $C_1$-$C_6$ alkyl, wherein said alkyl is unsubstituted or substituted with one or more substituents.

In some embodiments, $R^5$ and $R^6$ are independently $C_1$-$C_6$ alkyl, wherein said alkyl is unsubstituted or substituted with one or more substituents independently selected from alkoxy, heteroaryl and —$C(O)OR^{11}$.

In some embodiments, $R^1$ and $R^2$ are independently alkyl, heterocycloalkyl, alkoxy, phenyl or benzyloxy, wherein said alkyl, heterocycloalkyl, alkoxy, phenyl and benzyloxy are unsubstituted or substituted with one or more substituents independently selected from halo, alkyl, nitro, alkylsulfonyl and trihalomethyl.

In some embodiments, $R^1$ is alkyl, heterocycloalkyl, alkoxy, phenyl or benzyloxy, wherein said alkyl is unsubstituted or substituted with one or more halos, and said heterocycloalkyl is unsubstituted or substituted with alkyl; and $R^2$ is alkyl or aryl.

In some embodiments, Y is alkyl, wherein said alkyl is substituted with one or more substituents independently selected from W.

In some embodiments, Y is alkyl, wherein said alkyl is substituted with one or more halos.

In some embodiments, Y is alkyl, wherein said alkyl is substituted with one or more substituents independently selected from W; and $R^1$ and $R^2$ are independently alkyl, alkoxy, phenyl or benzyloxy, wherein said alkyl and phenyl are unsubstituted or substituted with one or more substituents.

In some embodiments, Y is alkyl, wherein said alkyl is substituted with one or more substituents independently selected from W; and $R^1$ and $R^2$ are independently alkyl, alkoxy, phenyl or benzyloxy, wherein said alkyl and phenyl are unsubstituted or substituted with one or more substituents independently selected from halo, nitro, alkylsulfonyl and trihalomethyl.

In some embodiments, $R^1$ is alkyl or alkoxy; and $R^2$ is alkyl or phenyl, wherein said phenyl is unsubstituted or substituted with one or more substituents independently selected from halo, nitro, alkylsulfonyl and trihalomethyl.

In some embodiments, Y is phenyl substituted with halo and —$CONR^3R^4$.

In some embodiments, $R^3$ and $R^4$ are taken together to form a cycloalkyl.

In some embodiments, $R^3$ and $R^4$ are taken together to form a cycloalkyl wherein said cycloalkyl is substituted with one or more substituents.

In some embodiments, $R^3$ and $R^4$ are taken together to form a heterocycloalkyl.

In some embodiments, $R^3$ and $R^4$ are taken together to form a heterocycloalkyl wherein said heterocycloalkyl is substituted with one or more substituents.

In some embodiments, the invention provides a compound of formula (Ia)

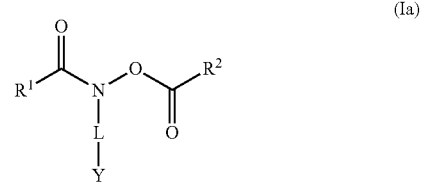

(Ia)

or a pharmaceutically acceptable salt, hydrate, or solvate thereof wherein:

L is a bond, —$SO_2$— or —O—;

Y is a heteroaryl, wherein said heteroaryl is unsubstituted or substituted with one or more substituents independently selected from W;

W is halo, —CN, —$NO_2$, —$COR^3$, —$COOR^3$, —$CONR^3R^4$, —$CH(C(O)R^3)_2$, —$SO_2R^3$ or —COX, wherein X is halo, and $R^3$ and $R^4$ are independently alkyl or aryl, or $R^3$ and $R^4$ are taken together to form a cycloalkyl or heterocycloalkyl, wherein said cycloalkyl or heterocycloalkyl are unsubstituted or substituted with one or more substituents;

$R^1$ and $R^2$ are independently hydrogen, alkyl, heterocycloalkyl, aryl, benzyl, alkoxy, aryloxy, benzyloxy or —$NR^5R^6$, wherein said alkyl, heterocycloalkyl, aryl, benzyl, alkoxy, aryloxy, and benzyloxy are unsubstituted or substituted with one or more substituents independently selected from halo, alkyl, nitro, alkylsulfonyl and trihalomethyl; and $R^5$ and $R^6$ are independently alkyl or aryl.

In some embodiments, L is —$SO_2$—.

In some embodiments, Y is unsubstituted heteroaryl.

In some embodiments, Y is heteroaryl substituted with one or more substituents independently selected from W.

In some embodiments, Y is thienyl, furyl, pyrrolyl, pyridyl or benzofuranyl.

In some embodiments, Y is thienyl, furyl, pyrrolyl, pyridyl or benzofuranyl substituted with one or more substituents independently selected from W.

In some embodiments, Y is thienyl substituted with one or more substituents independently selected from W.

In some embodiments, Y is benzofuranyl.

In some embodiments, Y is pyridyl.

In some embodiments, W is halo.

In some embodiments, W is chloro or bromo.

In some embodiments, $R^1$ is alkoxy.

In some embodiments, $R^2$ is alkyl.

In some embodiments, the invention provides a compound of formula (II)

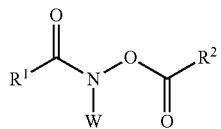

or a pharmaceutically acceptable salt, hydrate, or solvate thereof wherein:

W is halo, —OH, —CN, —NO$_2$, —COR$^3$, —COOR$^3$, —CONR$^3$R$^4$, —CH(C(O)R$^3$)$_2$, or —COX, wherein X is halo, and R$^3$, R$^4$ and R$^5$ are independently alkyl or aryl, or R$^3$ and R$^4$ are taken together to form a cycloalkyl or heterocycloalkyl, wherein said cycloalkyl and heterocycloalkyl are unsubstituted or substituted with one or more substituents;

R$^1$ and R$^2$ are independently hydrogen, alkyl, heterocycloalkyl, aryl, benzyl, alkoxy, aryloxy, benzyloxy or —NR$^6$R$^7$, wherein said alkyl, heterocycloalkyl, aryl, benzyl, alkoxy, aryloxy and benzyloxy are unsubstituted or substituted with one or more substituents; and R$^6$ and R$^7$ are independently alkyl or aryl.

In some embodiments, when R$^1$ and R$^2$ are each phenyl, then W is not —CN; and when R$^1$ is phenylethyl and R$^2$ is methyl, then W is not chloro.

Included in any of the embodiments disclosed above are the following additional embodiments which may be combined in any variation.

In some embodiments, W is chloro.

In some embodiments, W is bromo.

In some embodiments, W is fluoro.

In some embodiments, R$^1$ and R$^2$ are independently alkyl, alkoxy or phenyl, wherein said alkyl and phenyl are unsubstituted or substituted with one or more substituents independently selected from halo, nitro, alkylsulfonyl and trihalomethyl.

In some embodiments, W is —CONR$^3$R$^4$.

In some embodiments, R$^3$ and R$^4$ are taken together to form a cycloalkyl.

In some embodiments, R$^3$ and R$^4$ are taken together to form a cycloalkyl wherein said cycloalkyl is substituted with one or more substituents.

In some embodiments, R$^3$ and R$^4$ are taken together to form a heterocycloalkyl.

In some embodiments, R$^3$ and R$^4$ are taken together to form a heterocycloalkyl wherein said heterocycloalkyl is substituted with one or more substituents.

Representative compounds of formulae (I), (Ia) and (II) include, but are not limited to, the following compounds (Table 2).

TABLE 2

Representative compounds of formulae (I), (Ia) and (II):

| Compound No. | Name | Structure |
|---|---|---|
| 1 | N-chloro-N-benzoyloxy-benzamide | 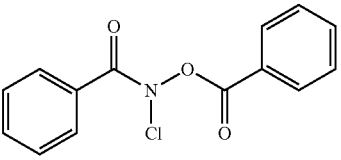 [SMILES: O=C(ON(Cl)C(=O)c1ccccc1)c1ccccc1] |
| 2 | N-chloro-N-(4-chlorobenzoyloxy)-4-chlorobenzamide | 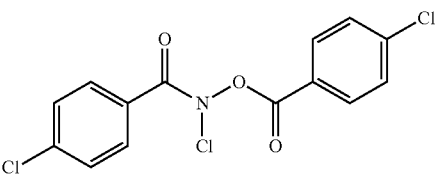 [SMILES: O=C(ON(Cl)C(=O)c1ccc(Cl)cc1)c1ccc(Cl)cc1] |
| 3 | N-chloro-N-(4-nitrobenzoyl)-4-nitrobenzamide | 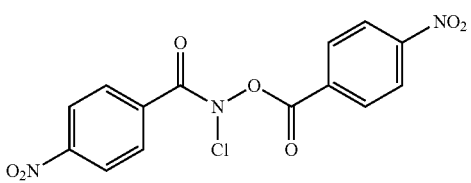 [SMILES: O=C(ON(Cl)C(=O)c1ccc([N+](=O)[O-])cc1)c1ccc([N+](=O)[O-])cc1] |

TABLE 2-continued

Representative compounds of formulae (I), (Ia) and (II):

| Compound No. | Name | Structure |
|---|---|---|
| 4 | N-chloro-N-(4-nitrobenzoyl)-benzamide | 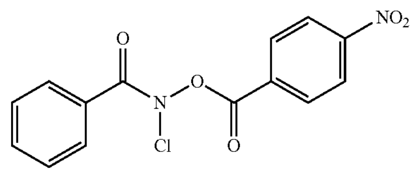 [SMILES: O=C(ON(Cl)C(=O)c1ccccc1)c1ccc([N+](=O)[O-])cc1] |
| 5 | N-chloro-N-(2,6-difluorobenzoyl)-benzamide | 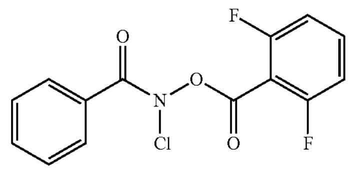 [SMILES: O=C(ON(Cl)C(=O)c1ccccc1)c1c(F)cccc1F] |
| 6 | N-chloro-N-acetoxy-benzamide | 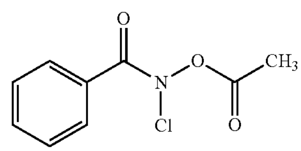 |
| 7 | N-chloro-N-dichloroacetyloxy-benzamide | 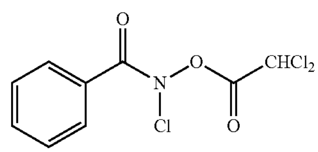 |
| 8 | N-chloro-N-(2,2,2-trifluoroacetoxy)benzamide | 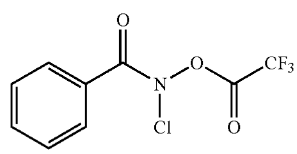 [SMILES: O=C(c1ccccc1)N(Cl)OC(=O)C(F)(F)F] |
| 9 | N-chloro-N-acetyloxy-acetamide | 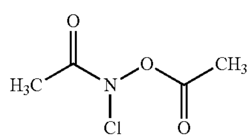 |
| 10 | N-chloro-N-acetyloxy-tert-butyl-carbamate | 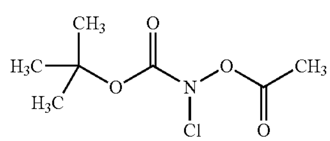 |
| 11 | N-chloro-N-ethyl-carbonoxy-ethyl-carbamate | 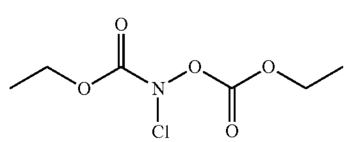 |
| 12 | N-chloro-N-(trimethylacetyloxy)-trimethylacetamide | 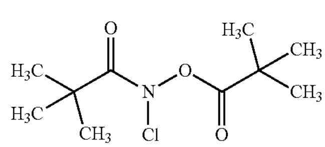 |

TABLE 2-continued

Representative compounds of formulae (I), (Ia) and (II):

| Compound No. | Name | Structure |
|---|---|---|
| 13 | N-chloro-N-(4-nitrobenzoyloxy)-tert-butyl-carbamate | 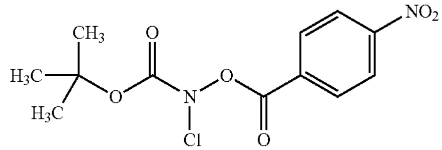 [SMILES: CC(C)(C)OC(=O)N(Cl)OC(=O)c1ccc([N+](=O)[O-])cc1] |
| 14 | N-chloro-N-(acetyloxy)-trimethylacetamide | 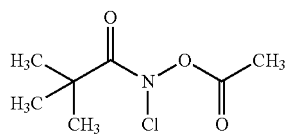 |
| 15 | N-bromo-N-acetyloxy-acetamide | 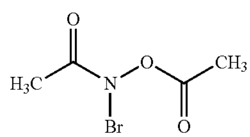 |
| 18 | N-(4-chlorobenzenesulfonyl)-4-acetyloxy-acetamide[4] | 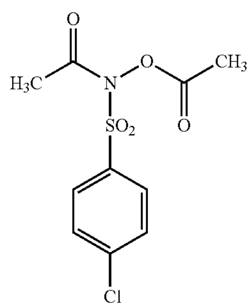 [SMILES: CC(=O)ON(C(C)=O)S(=O)(=O)c1ccc(Cl)cc1] |
| 19 | N-(2-bromobenzenesulfonyl)-N-acetyloxy-acetamide | 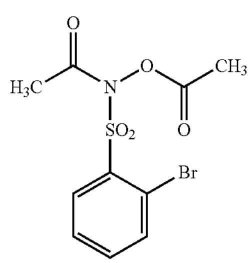 |
| 20 | N-(2-chlorobenzenesulfonyl)-N-acetyloxy-acetamide | 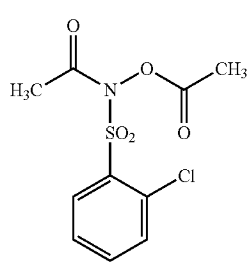 [SMILES: CC(=O)ON(C(C)=O)S(=O)(=O)c1ccccc1Cl] |

TABLE 2-continued

Representative compounds of formulae (I), (Ia) and (II):

| Compound No. | Name | Structure |
|---|---|---|
| 21 | N-(2-bromo-4,6-difluoro-benzenesulfonyl)-N-acetyloxy-acetamide | 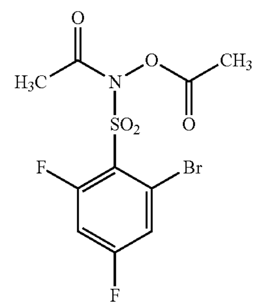 [SMILES: CC(=O)ON(C(C)=O)S(=O)(=O)c1c(F)cc(F)cc1Br] |
| 22 | N-(2,6-dibromobenzenesulfonyl)-N-acetyloxy-acetamide | 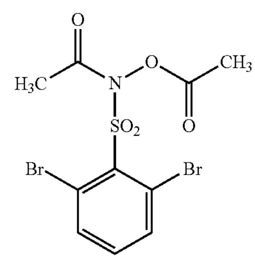 [SMILES: CC(=O)ON(C(C)=O)S(=O)(=O)c1c(Br)cccc1Br] |
| 23 | N-(2,6-dichlorobenzenesulfnyl)-N-acetyloxy-acetamide | 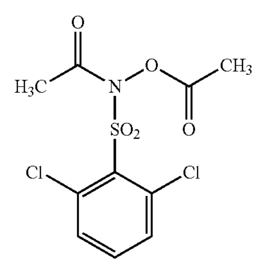 [SMILES: CC(=O)ON(C(C)=O)S(=O)(=O)c1c(Cl)cccc1Cl] |
| 24 | N-(2,6-difluorobenzenesulfonyl)-N-acetyloxy-acetamide | 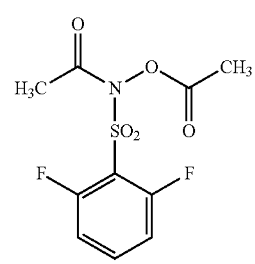 [SMILES: CC(=O)ON(C(C)=O)S(=O)(=O)c1c(F)cccc1F] |
| 25 | N-(2-nitrobenzenesulfonyl)-N-acetyloxy-acetamide | 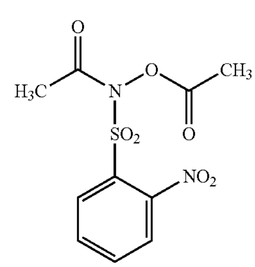 [SMILES: CC(=O)ON(C(C)=O)S(=O)(=O)c1ccccc1[N+](=O)[O-]] |

TABLE 2-continued
Representative compounds of formulae (I), (Ia) and (II):
| Compound No. | Name | Structure |
|---|---|---|
| 26 | N-(chloromethylsulfonyl)-N-acetyloxy-acetamide | 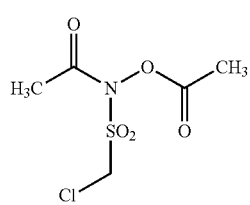 |
| 27 | no spectral data | 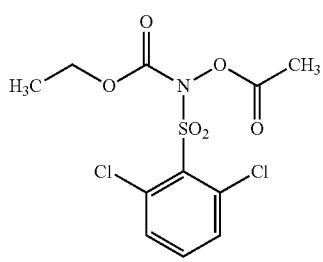 [SMILES: CCOC(=O)N(OC(C)=O)S(=O)(=O)c1c(Cl)cccc1Cl] |
| 28 | N-(2,6-dichlorobenzenesulfonyl)-N-acetyloxy-benzamide | 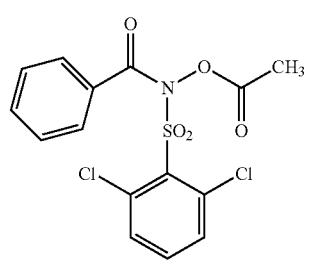 [SMILES: CC(=O)ON(C(=O)c1ccccc1)S(=O)(=O)c1c(Cl)cccc1Cl] |
| 29 | N-(2,6-dichlorobenzenesulfonyl)-N-acetyloxy-benzyl-carbamate | 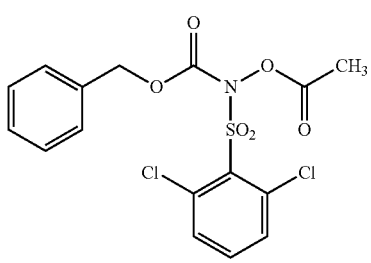 [SMILES: CC(=O)ON(C(=O)OCc1ccccc1)S(=O)(=O)c1c(Cl)cccc1Cl] |
| 30 | N-(2,6-dichlorobenzenesulfonyl)-N-acetyloxy-dichloroacetamide | 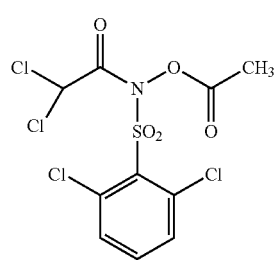 [SMILES: CC(=O)ON(C(=O)C(Cl)Cl)S(=O)(=O)c1c(Cl)cccc1Cl] |

TABLE 2-continued

Representative compounds of formulae (I), (Ia) and (II):

| Compound No. | Name | Structure |
|---|---|---|
| 31 | N-(2,5-dichlorobenzenesulfonyl)-N-acetyloxy-trimethylacetamide | 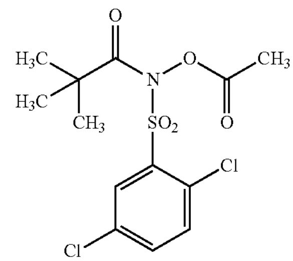 [SMILES: CC(=O)ON(C(=O)C(C)(C)C)S(=O)(=O)c1cc(Cl)ccc1Cl] |
| 32 | N-(2-nitrobenzenesulfonyl)-N-acetyloxy-trimethylacetamide | 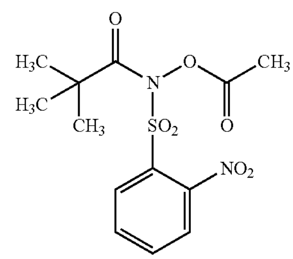 [SMILES: CC(=O)ON(C(=O)C(C)(C)C)S(=O)(=O)c1ccccc1[N+](=O)[O-]] |
| 33 | N-(2,6-dichlorobenzenesulfonyl)-N-acetyloxy-trimethylacetamide | 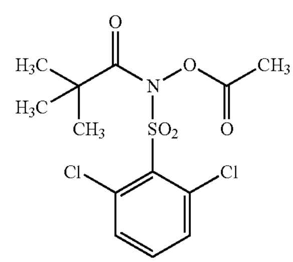 [SMILES: CC(=O)ON(C(=O)C(C)(C)C)S(=O)(=O)c1c(Cl)cccc1Cl] |
| 36 | N-(2-bromobenzenesulfonyl)-N-acetyloxy-tert-butyl-carbamate | 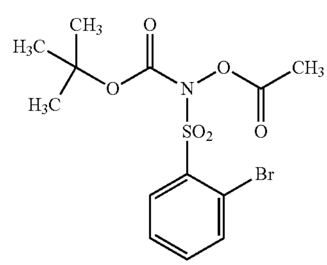 [SMILES: CC(=O)ON(C(=O)OC(C)(C)C)S(=O)(=O)c1ccccc1Br] |
| 37 | N-(2,6-dichlorobenzenesulfonyl)-N-acetyloxy-tert-butyl-carbamate | 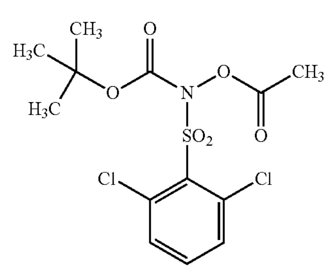 [SMILES: CC(=O)ON(C(=O)OC(C)(C)C)S(=O)(=O)c1c(Cl)cccc1Cl] |

TABLE 2-continued

Representative compounds of formulae (I), (Ia) and (II):

| Compound No. | Name | Structure |
|---|---|---|
| 38 | N-(2,6-dibromobenzenesulfonyl)-N-acetyloxy-tert-butyl-carbamate | 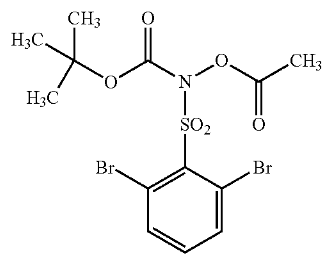 [SMILES: CC(=O)ON(C(=O)OC(C)(C)C)S(=O)(=O)c1c(Br)cccc1Br] |
| 40 | N-(2,6-dichlorobenzenesulfonyl)-N-4-nitrobenzoyloxy)-tert-butyl-carbamate | 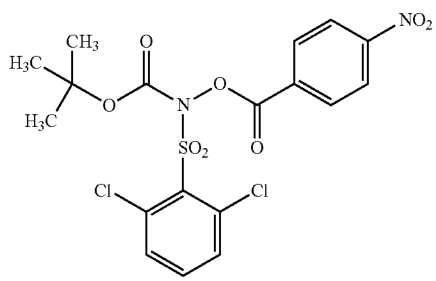 [SMILES: CC(C)(C)OC(=O)N(OC(=O)c1ccc([N+](=O)[O-])cc1)S(=O)(=O)c1c(Cl)cccc1Cl] |
| 41 | tert-butyl (acetyloxy)[(2-bromophenyl)sulfonyl]carbamate | 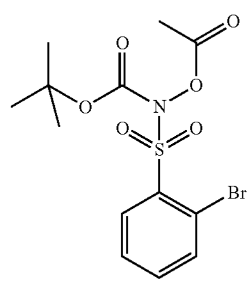 [SMILES: CC(=O)ON(C(=O)OC(C)(C)C)S(=O)(=O)c1ccccc1Br] |
| 42 | tert-butyl (acetyloxy){[2-(methylsulfonyl)phenyl]sulfonyl}-carbamate | 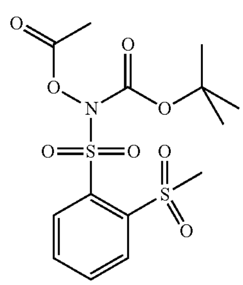 [SMILES: CC(=O)ON(C(=O)OC(C)(C)C)S(=O)(=O)c1ccccc1S(C)(=O)=O] |
| 43 | tert-butyl (acetyloxy)[(3-bromothiophen-2-yl)sulfonyl]carbamate | 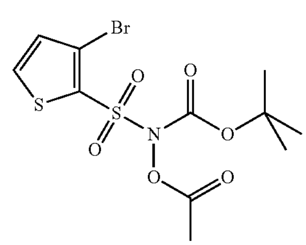 [SMILES: CC(=O)ON(C(=O)OC(C)(C)C)S(=O)(=O)c1sccc1Br] |

TABLE 2-continued

Representative compounds of formulae (I), (Ia) and (II):

| Compound No. | Name | Structure |
|---|---|---|
| 44 | tert-butyl {[2-(methylsulfonyl)phenyl]-sulfonyl}(propanoyloxy)carbamate | 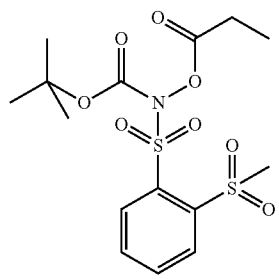 [SMILES: CCC(=O)ON(C(=O)OC(C)(C)C)S(=O)(=O)c1ccccc1S(C)(=O)=O] |
| 45 | tert-butyl [(2-methylpropanoyl)oxy]{[2-(methylsulfonyl)phenyl]sulfonyl}-carbamate | 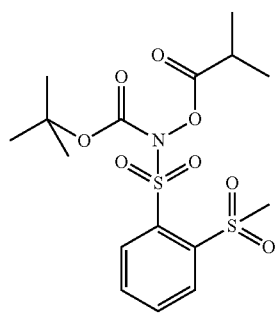 [SMILES: CC(C)C(=O)ON(C(=O)OC(C)(C)C)S(=O)(=O)c1ccccc1S(C)(=O)=O] |
| 46 | tert-butyl [(2,2-dimethylpropanoyl)oxy]-{[2(methylsulfonyl)phenyl]sulfonyl}-carbamate | 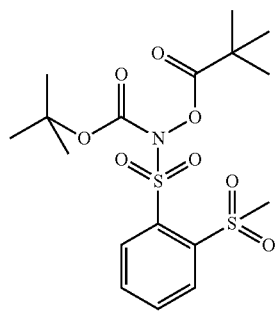 [SMILES: CC(C)(C)OC(=O)N(OC(=O)C(C)(C)C)S(=O)(=O)c1ccccc1S(C)(=O)=O] |
| 47 | tert-butyl {[2-(methylsulfonyl)phenyl]-sulfonyl}[(phenylcarbonyl)oxy]-carbamate | 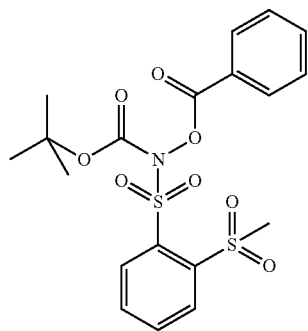 [SMILES: CC(C)(C)OC(=O)N(OC(=O)c1ccccc1)S(=O)(=O)c1ccccc1S(C)(=O)=O] |

TABLE 2-continued

Representative compounds of formulae (I), (Ia) and (II):

| Compound No. | Name | Structure |
|---|---|---|
| 48 | ethyl (acetyloxy){[2-(methylsulfonyl)phenyl]sulfonyl}carbamate | 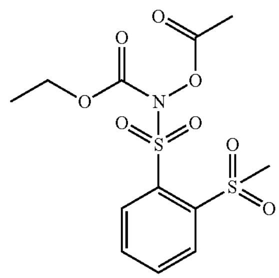 [SMILES: CCOC(=O)N(OC(C)=O)S(=O)(=O)c1ccccc1S(C)(=O)=O] |
| 49 | ethyl (acetyloxy)[(2-bromophenyl)sulfonyl]carbamate | 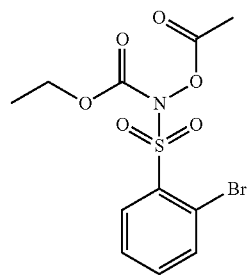 [SMILES: CCOC(=O)N(OC(C)=O)S(=O)(=O)c1ccccc1Br] |
| 50 | benzyl (acetylxoy){[2-(methylsulfonyl)phenyl]sulfonyl}carbamate | 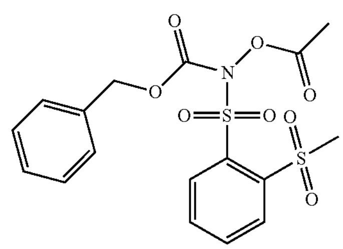 [SMILES: CC(=O)ON(C(=O)OCc1ccccc1)S(=O)(=O)c1ccccc1S(C)(=O)=O] |
| 51 | benzyl {[2-(methylsulfonyl)phenyl]sulfonyl}(propanoyloxy)carbamate | 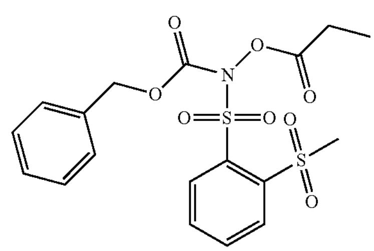 [SMILES: CCC(=O)ON(C(=O)OCc1ccccc1)S(=O)(=O)c1ccccc1S(C)(=O)=O] |
| 52 | N-[(2,2-dimethylpropanoyl)oxy]-4-methyl-N-{[2-(methylsulfonyl)phenyl]sulfonyl}piperazine-1-carboxamide | 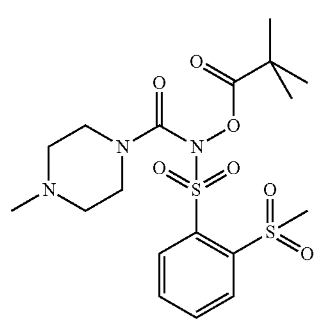 |

TABLE 2-continued

Representative compounds of formulae (I), (Ia) and (II):

| Compound No. | Name | Structure |
|---|---|---|
| 53 | N-[(tert-butoxy)carbonyl][2-chloro-5-(dimethylcarbamoyl)benzene]sulfonamido 2,2-dimethylpropanoate | 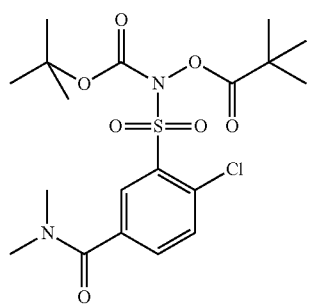 [SMILES: CN(C)C(=O)c1ccc(Cl)c(S(=O)(=O)N(OC(=O)C(C)(C)C)C(=O)OC(C)(C)C)c1] |
| 54 | N-[(tert-butoxy)carbonyl](2-methanesulfonylbenzene)sulfonamido 2-(acetyloxy)benzoate | 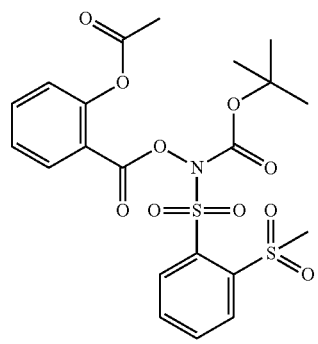 [SMILES: CC(=O)Oc1ccccc1C(=O)ON(C(=O)OC(C)(C)C)S(=O)(=O)c1ccccc1S(C)(=O)=O] |
| 55 | N-[(tert-butoxy)carbonyl]1-benzofuran-2-sulfonamido 2,2-dimethylpropanoate | 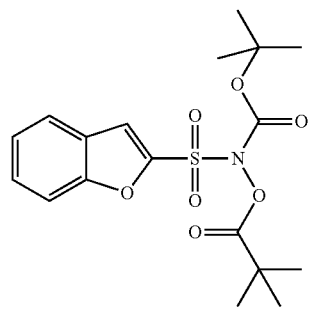 [SMILES: CC(C)(C)OC(=O)N(OC(=O)C(C)(C)C)S(=O)(=O)c1cc2ccccc2o1] |
| 56 | N-[(tert-butoxy)carbonyl]1-benzofuran-2-sulfonamido acetate | 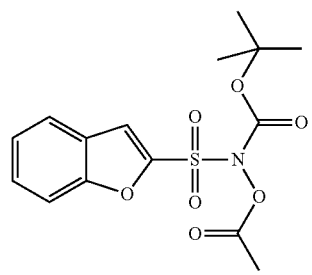 [SMILES: CC(=O)ON(C(=O)OC(C)(C)C)S(=O)(=O)c1cc2ccccc2o1] |

TABLE 2-continued

Representative compounds of formulae (I), (Ia) and (II):

| Compound No. | Name | Structure |
|---|---|---|
| 57 | N-[(tert-butoxy)carbonyl](2-bromobenzene)sulfonamido benzoate | 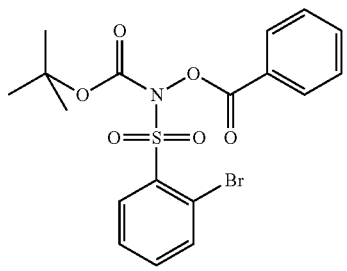 [SMILES: CC(C)(C)OC(=O)N(OC(=O)c1ccccc1)S(=O)(=O)c1ccccc1Br] |
| 58 | N-[(tert-butoxy)carbonyl]3-bromothiophene-2-sulfonamido 2,2-dimethylpropanoate | 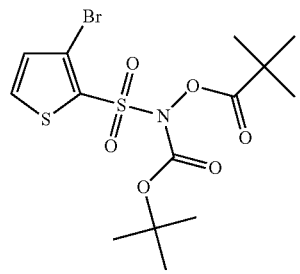 [SMILES: CC(C)(C)OC(=O)N(OC(=O)C(C)(C)C)S(=O)(=O)c1sccc1Br] |
| 59 | N-[(tert-butoxy)carbonyl]3-chlorothiophene-2-sulfonamido 2,2-dimethylpropanoate | 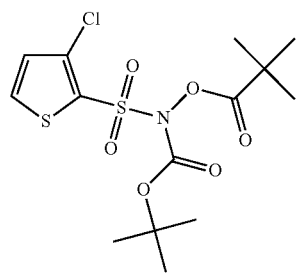 [SMILES: CC(C)(C)OC(=O)N(OC(=O)C(C)(C)C)S(=O)(=O)c1sccc1Cl] |
| 60 | N-[(tert-butoxy)carbonyl](2-bromobenzene)sulfonamido 2-methylpropanoate | 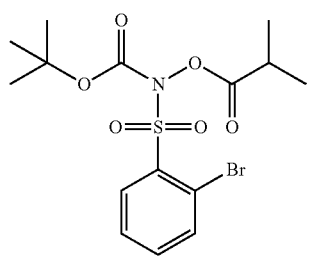 [SMILES: CC(C)C(=O)ON(C(=O)OC(C)(C)C)S(=O)(=O)c1ccccc1Br] |
| 61 | N-[(tert-butoxy)carbonyl](2-bromobenzene)sulfonamido 2,2-dimethylpropanoate | 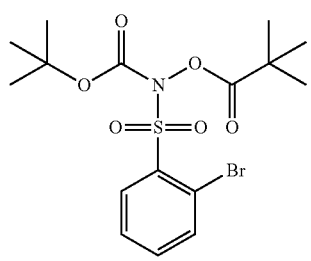 [SMILES: CC(C)(C)OC(=O)N(OC(=O)C(C)(C)C)S(=O)(=O)c1ccccc1Br] |

TABLE 2-continued

Representative compounds of formulae (I), (Ia) and (II):

| Compound No. | Name | Structure |
|---|---|---|
| 62 | N-[(tert-butoxy)carbonyl](2-chlorobenzene)sulfonamido 2,2-dimethylpropanoate | 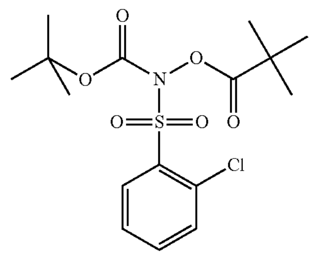 [SMILES: CC(C)(C)OC(=O)N(OC(=O)C(C)(C)C)S(=O)(=O)c1ccccc1Cl] |
| 63 | N-[(tert-butoxy)carbonyl][2-chloro-5-(dimethylcarbamoyl)benzene]sulfonamido-acetate | 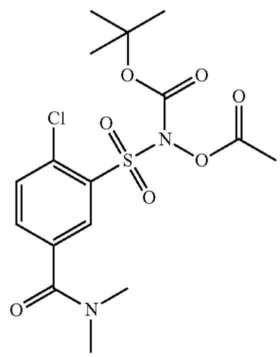 [SMILES: CC(=O)ON(C(=O)OC(C)(C)C)S(=O)(=O)c1cc(C(=O)N(C)C)ccc1Cl] |
| 64 | N-[(tert-butoxy)carbonyl](2-chlorobenzene)sulfonamido 2-methylpropanoate | 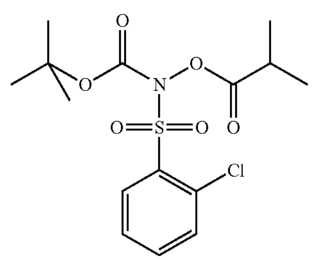 [SMILES: CC(C)C(=O)ON(C(=O)OC(C)(C)C)S(=O)(=O)c1ccccc1Cl] |
| 65 | N-[(tert-butoxy)carbonyl](2-bromobenzene)sulfonamido 2-phenylacetate | 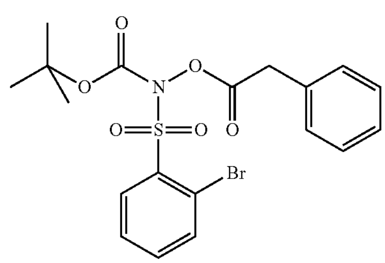 [SMILES: CC(C)(C)OC(=O)N(OC(=O)Cc1ccccc1)S(=O)(=O)c1ccccc1Br] |
| 66 | N-[(tert-butoxy)carbonyl](2-bromobenzene)sulfonamido 2-methyl-2-phenylpropanoate | 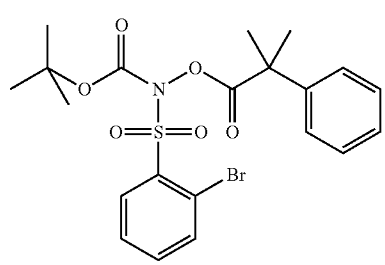 [SMILES: CC(C)(C)OC(=O)N(OC(=O)C(C)(C)c1ccccc1)S(=O)(=O)c1ccccc1Br] |

TABLE 2-continued

Representative compounds of formulae (I), (Ia) and (II):

| Compound No. | Name | Structure |
|---|---|---|
| 67 | N-[(tert-butoxy)carbonyl](2-bromobenzene)sulfonamido 1-phenylcyclopentane-1-carboxylate | 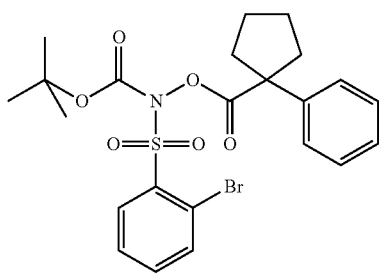 [SMILES: CC(C)(C)OC(=O)N(OC(=O)C1(c2ccccc2)CCCC1)S(=O)(=O)c1ccccc1Br] |
| 68 | 2-N-[(tert-butoxy)carbonyl](2-bromobenzene)sulfonamido 1-tert-butyl pyrrolidine-1,2-dicarboxylate | 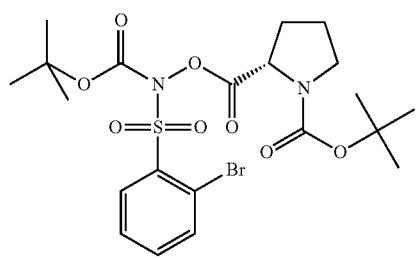 [SMILES: CC(C)(C)OC(=O)N1CCC[C@H]1C(=O)ON(C(=O)OC(C)(C)C)S(=O)(=O)c1ccccc1Br] |
| 69 | N-[(tert-butoxy)carbonyl](2-bromobenzene)sulfonamido 2-[4-(dimethylamino)phenyl]acetate | 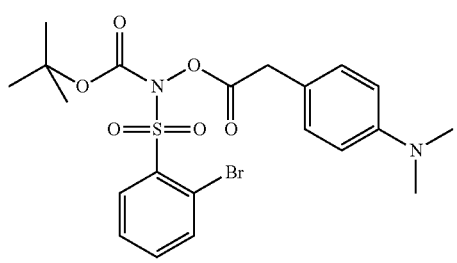 [SMILES: CN(C)c1ccc(CC(=O)ON(C(=O)OC(C)(C)C)S(=O)(=O)c2ccccc2Br)cc1] |
| 70 | N-[(tert-butoxy)carbonyl](2-bromobenzene)sulfonamido 1-acetylpyrrolidine-2-carboxylate | 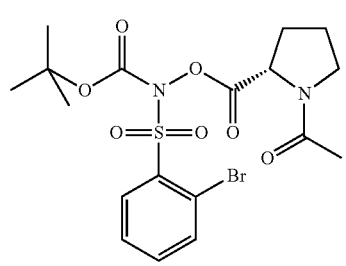 [SMILES: CC(=O)N1CCC[C@H]1C(=O)ON(C(=O)OC(C)(C)C)S(=O)(=O)c1ccccc1Br] |
| 71 | N-[(tert-butoxy)carbonyl](2-bromobenzene)sulfonamido (2S)-2-phenylpropanoate | 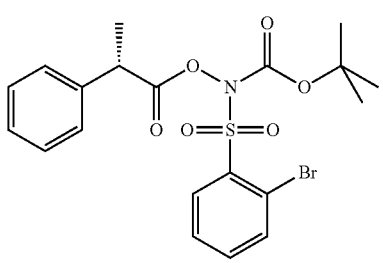 [SMILES: C[C@H](C(=O)ON(C(=O)OC(C)(C)C)S(=O)(=O)c1ccccc1Br)c1ccccc1] |

TABLE 2-continued

Representative compounds of formulae (I), (Ia) and (II):

| Compound No. | Name | Structure |
|---|---|---|
| 72 | N-[(tert-butoxy)carbonyl](2-bromobenzene)sulfonamido (2R)-2-phenylpropanoate | 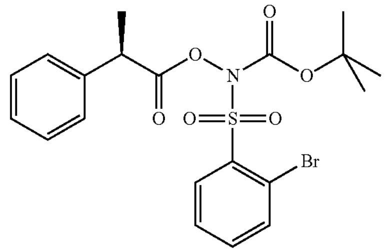 [SMILES: C[C@@H](C(=O)ON(C(=O)OC(C)(C)C)S(=O)(=O)c1ccccc1Br)c1ccccc1] |
| 73 | N-[(tert-butoxy)carbonyl]-5-chlorothiophene-2-sulfonamido 2-methylpropanoate | 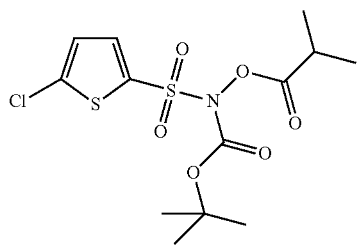 [SMILES: CC(C)C(=O)ON(C(=O)OC(C)(C)C)S(=O)(=O)c1ccc(Cl)s1] |
| 74 | N-[(tert-butoxy)carbonyl]-5-chlorothiophene-2-sulfonamido 2,2-dimethylpropanoate | 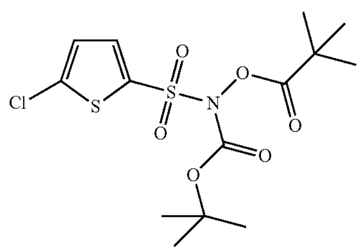 [SMILES: CC(C)(C)OC(=O)N(OC(=O)C(C)(C)C)S(=O)(=O)c1ccc(Cl)s1] |
| 75 | N-[(tert-butoxy)carbonyl](3-methanesulfonylbenzene)sulfonamido 2,2-dimethylpropanate | 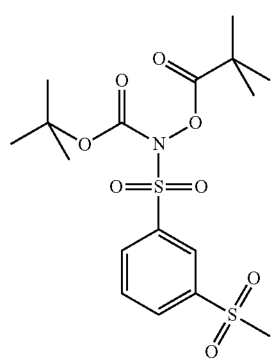 [SMILES: CC(C)(C)OC(=O)N(OC(=O)C(C)(C)C)S(=O)(=O)c1cccc(S(C)(=O)=O)c1] |
| 76 | N-[(tert-butoxy)carbonyl](3-methanesulfonylbenzene)sulfonamido 2-methylpropanoate | 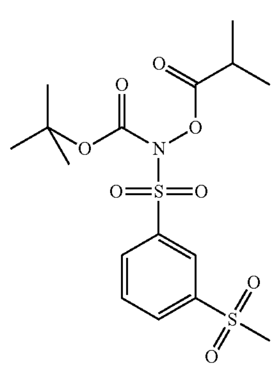 [SMILES: CC(C)C(=O)ON(C(=O)OC(C)(C)C)S(=O)(=O)c1cccc(S(C)(=O)=O)c1] |

TABLE 2-continued

Representative compounds of formulae (I), (Ia) and (II):

| Compound No. | Name | Structure |
|---|---|---|
| 77 | N-[(tert-butoxy)carbonyl]pyridine-3-sulfonamido 2,2-dimethylpropanoate | 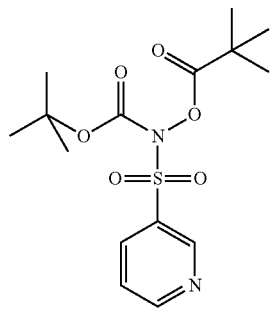 [SMILES: CC(C)(C)OC(=O)N(OC(=O)C(C)(C)C)S(=O)(=O)c1cccnc1] |
| 78 | N-[(tert-butoxy)carbonyl]pyridine-3-sulfonamido 2-methylpropanoate | 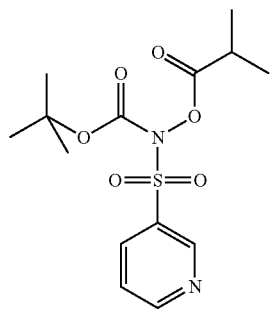 [SMILES: CC(C)C(=O)ON(C(=O)OC(C)(C)C)S(=O)(=O)c1cccnc1] |
| 79 | N-[(tert-butoxy)carbonyl](2-methanesulfonylbenzene)sulfonamido (2S)-2-{[(tert butoxy)carbonyl](methyl)amino}-4-methylpentanoate | 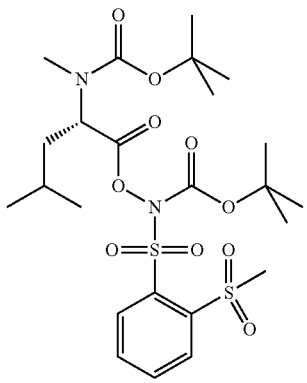 [SMILES: CC(C)C[C@@H](C(=O)ON(C(=O)OC(C)(C)C)S(=O)(=O)c1ccccc1S(C)(=O)=O)N(C)C(=O)OC(C)(C)C] |
| 80 | N-[(tert-butoxy)carbonyl](2-methanesulfonylbenzene)sulfonamido (2R)-2-{[(tert-butoxy)carbonyl](methyl)amino}propanoate | 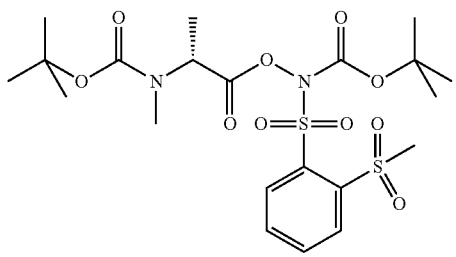 [SMILES: C[C@H](C(=O)ON(C(=O)OC(C)(C)C)S(=O)(=O)c1ccccc1S(C)(=O)=O)N(C)C(=O)OC(C)(C)C] |

TABLE 2-continued

Representative compounds of formulae (I), (Ia) and (II):

| Compound No. | Name | Structure |
|---|---|---|
| 81 | N-[(tert-butoxy)carbonyl](2-methanesulfonylbenzene)sulfonamido (2S)-2-{[(tert-butoxy)carbonyl](methyl)amino}propanoate | 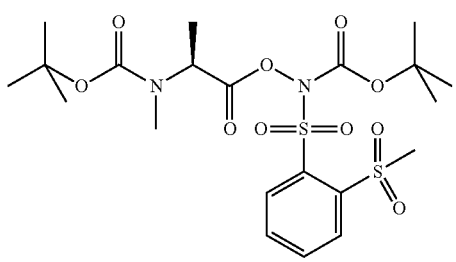 [SMILES: C[C@@H](C(=O)ON(C(=O)OC(C)(C)C)S(=O)(=O)c1ccccc1S(C)(=O)=O)N(C)C(=O)OC(C)(C)C] |
| 82 | N-[(tert-butoxy)carbonyl](2-methanesulfonylbenzene)sulfonamido 2-{[(tertbutoxy)carbonyl](methyl)amino}acetate | 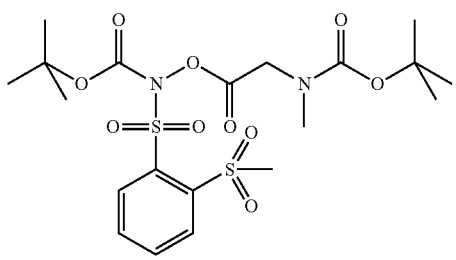 [SMILES: CN(CC(=O)ON(C(=O)OC(C)(C)C)S(=O)(=O)c1ccccc1S(C)(=O)=O)C(=O)OC(C)(C)C] |
| 83 | N-[(tert-butoxy)carbonyl](2-methanesulfonylbenzene)sulfonamido (2S)-2-{[(tert-butoxy)carbonyl](methyl)amino}-3-methylbutanoate | 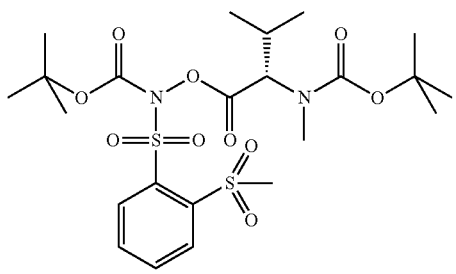 [SMILES: CC(C)[C@@H](C(=O)ON(C(=O)OC(C)(C)C)S(=O)(=O)c1ccccc1S(C)(=O)=O)N(C)C(=O)OC(C)(C)C] |
| 84 | N-[(tert-butoxy)carbonyl][(4-chlorophenyl)methane]sulfonamido 2,2-dimethylpropanoate | 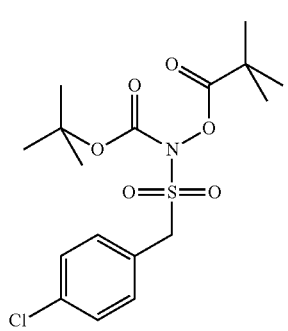 [SMILES: CC(C)(C)OC(=O)N(OC(=O)C(C)(C)C)S(=O)(=O)Cc1ccc(Cl)cc1] |
| 85 | N-[(benzyloxy)carbonyl](2-methanesulfonylbenzene)sulfonamido 2,2-dimethylpropanoate | 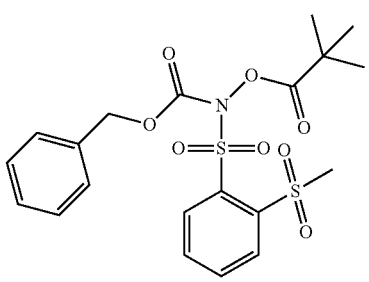 [SMILES: CC(C)(C)C(=O)ON(C(=O)OCc1ccccc1)S(=O)(=O)c1ccccc1S(C)(=O)=O] |

TABLE 2-continued

Representative compounds of formulae (I), (Ia) and (II):

| Compound No. | Name | Structure |
|---|---|---|
| 86 | N-[(tert-butoxy)carbonyl](2-methanesulfonylbenzene)sulfonamido N,N-dimethylcarbamate | 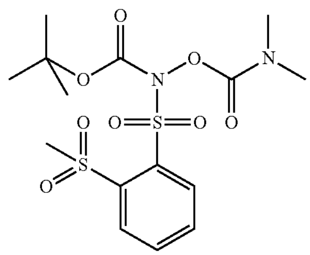 [SMILES: CN(C)C(=O)ON(C(=O)OC(C)(C)C)S(=O)(=O)c1ccccc1S(C)(=O)=O] |
| 87 | N-[(tert-butoxy)carbonyl](2-bromobenzene)sulfonamido N,N-dimethylcarbamate | 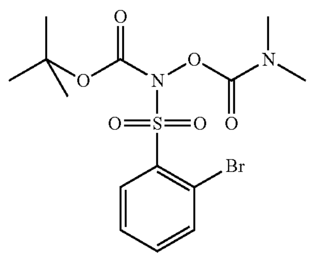 [SMILES: CN(C)C(=O)ON(C(=O)OC(C)(C)C)S(=O)(=O)c1ccccc1Br] |
| 88 | N-[(tert-butoxy)carbonyl](2-methanesulfonylbenzene)sulfonamido morpholine-4-carboxylate | 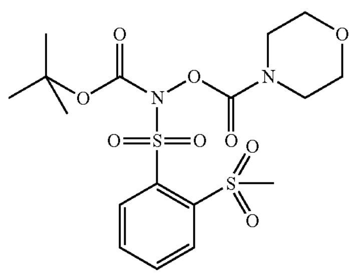 [SMILES: CC(C)(C)OC(=O)N(OC(=O)N1CCOCC1)S(=O)(=O)c1ccccc1S(C)(=O)=O] |
| 89 | N-[(tert-butoxy)carbonyl](2-methanesulfonylbenzene)sulfonamido 4-acetylpiperazine-1-carboxylate | 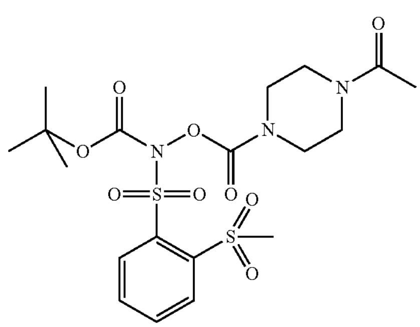 [SMILES: CC(=O)N1CCN(C(=O)ON(C(=O)OC(C)(C)C)S(=O)(=O)c2ccccc2S(C)(=O)=O)CC1] |
| 90 | tert-butyl N-{[cyclohexyl(methyl)carbamoyl]oxy}-N-[(2-methanesulfonylbenzene)sulfonyl]carbamate | 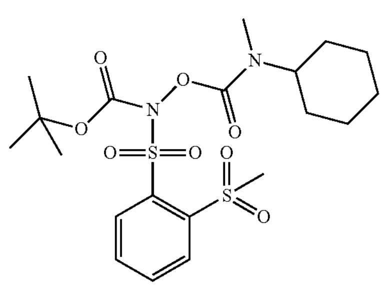 [SMILES: CN(C(=O)ON(C(=O)OC(C)(C)C)S(=O)(=O)c1ccccc1S(C)(=O)=O)C1CCCCC1] |

TABLE 2-continued

Representative compounds of formulae (I), (Ia) and (II):

| Compound No. | Name | Structure |
|---|---|---|
| 91 | 1-N-[(tert-butoxy)carbonyl](2-methanesulfonylbenzene)sulfonamido 4-tert-butyl piperazine-1,4-dicarboxylate | 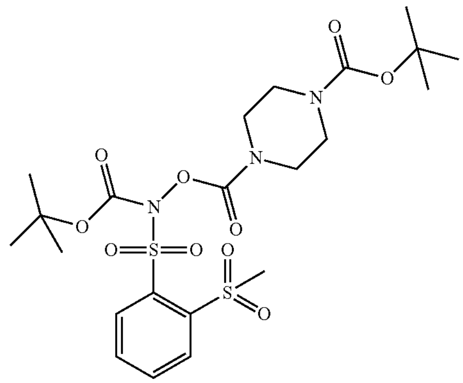 [SMILES: CC(C)(C)OC(=O)N1CCN(C(=O)ON(C(=O)OC(C)(C)C)S(=O)(=O)c2ccccc2S(C)(=O)=O)CC1] |
| 92 | N-[(tert-butoxy)carbonyl](2-methanesulfonylbenzene)sulfonamido N-(2-methoxyethyl)carbamate | 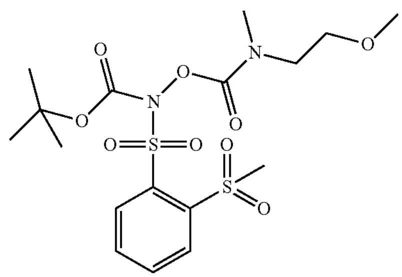 [SMILES: COCCN(C)C(=O)ON(C(=O)OC(C)(C)C)S(=O)(=O)c1ccccc1S(C)(=O)=O] |
| 93 | N-[(tert-butoxy)carbonyl](2-methanesulfonylbenzene)sulfonamido N,N diethylcarbamate | 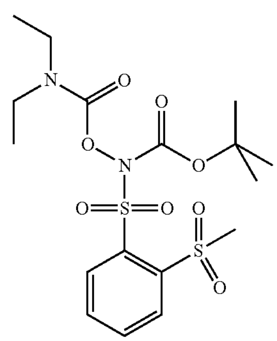 [SMILES: CCN(CC)C(=O)ON(C(=O)OC(C)(C)C)S(=O)(=O)c1ccccc1S(C)(=O)=O] |
| 94 | N-[(tert-butoxy)carbonyl](2-methanesulfonylbenzene)sulfonamido N-methoxy-N-methylcarbamate | 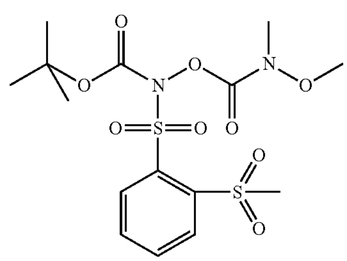 [SMILES: CON(C)C(=O)ON(C(=O)OC(C)(C)C)S(=O)(=O)c1ccccc1S(C)(=O)=O] |

TABLE 2-continued

Representative compounds of formulae (I), (Ia) and (II):

| Compound No. | Name | Structure |
|---|---|---|
| 95 | tert-butyl N-[(2-methanesulfonylbenzene)sulfonyl]-N-{[methyl(pyridin-3-ylmethyl)carbamoyl]oxy}carbamate | 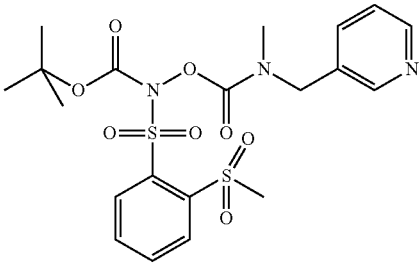 [SMILES: CN(Cc1cccnc1)C(=O)ON(C(=O)OC(C)(C)C)S(=O)(=O)c1ccccc1S(C)(=O)=O] |
| 96 | tert-butyl 2-{[2-(tert-butoxy)-2-oxoethyl][({N-[(tert-butoxy)carbonyl](2-methanesulfonylbenzene)sulfonamido}oxy)carbonyl]amino}acetate | 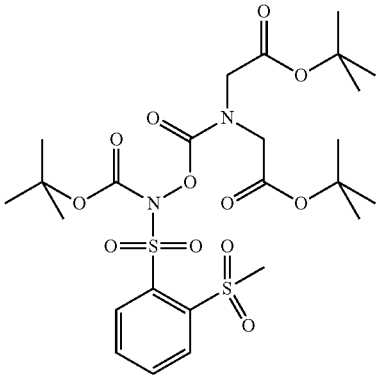 [SMILES: CC(C)(C)OC(=O)CN(CC(=O)OC(C)(C)C)C(=O)ON(C(=O)OC(C)(C)C)S(=O)(=O)c1ccccc1S(C)(=O)=O] |
| 97 | 4-{[({N-[(tert-butoxy)carbonyl](2-methanesulfonylbenzene)sulfonamido}oxy)carbonyl]oxy}oxane | 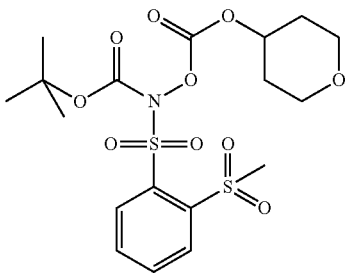 [SMILES: CC(C)(C)OC(=O)N(OC(=O)OC1CCOCC1)S(=O)(=O)c1ccccc1S(C)(=O)=O] |
| 98 | 4-{[({N-[(tert-butoxy)carobnyl](2-bromobenzene)sulfonamido}oxy)carbonyl]oxy}oxane | 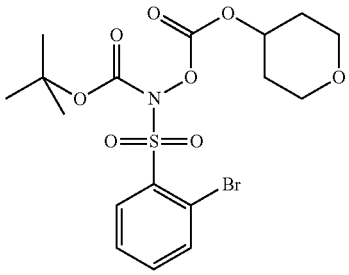 [SMILES: CC(C)(C)OC(=O)N(OC(=O)OC1CCOCC1)S(=O)(=O)c1ccccc1Br] |
| 99 | 1-({[[(tert-butoxy)carbonyl][(methoxycarbonyl)oxy]amino}sulfonyl)-2-methanesulfonyl benzene | 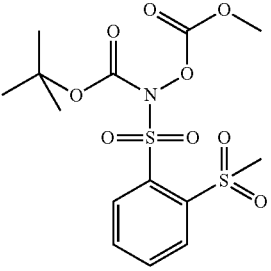 [SMILES: COC(=O)ON(C(=O)OC(C)(C)C)S(=O)(=O)c1ccccc1S(C)(=O)=O] |

TABLE 2-continued

Representative compounds of formulae (I), (Ia) and (II):

| Compound No. | Name | Structure |
|---|---|---|
| 100 | 1-({[(tert-butoxy)carbonyl]({[(2-methoxyethoxy)carbonyl]oxy})amino}sulfonyl)-2-methanesulfonylbenzene | 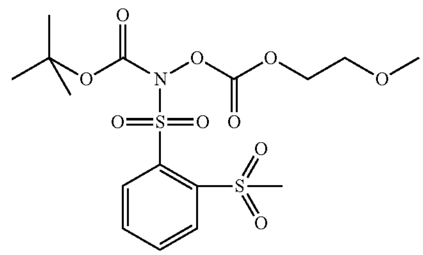 [SMILES: COCCOC(=O)ON(C(=O)OC(C)(C)C)S(=O)(=O)c1ccccc1S(C)(=O)=O] |
| 101 | 1-({[(tert-butoxy)carbonyl]({[2-(2-methoxyethoxy)ethoxy]carbonyl}oxy)amino}sulfonyl)-2-methanesulfonylbenzene | 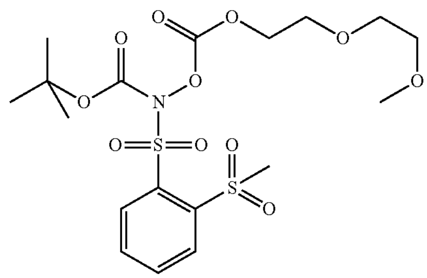 [SMILES: COCCOCCOC(=O)ON(C(=O)OC(C)(C)C)S(=O)(=O)c1ccccc1S(C)(=O)=O] |
| 102 | 1-({[(tert-butoxy)carbonyl]({[(1,3-diethoxypropan-2-yl)oxy]carbonyl}oxy)amino}sulfonyl)-2-methanesulfonylbenzene | 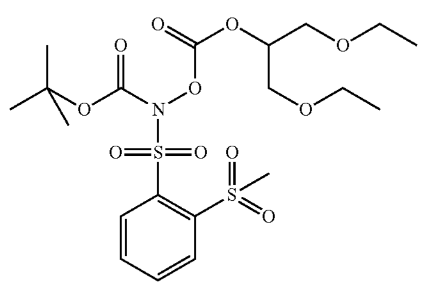 [SMILES: CCOCC(COCC)OC(=O)ON(C(=O)OC(C)(C)C)S(=O)(=O)c1ccccc1S(C)(=O)=O] |
| 103 | tert-butyl (acetyloxy)[(3-bromothiophen-2-yl)sulfonyl]carbamate | 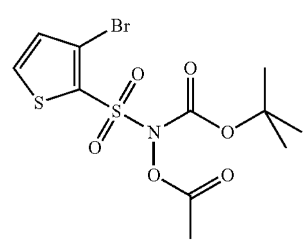 [SMILES: CC(=O)ON(C(=O)OC(C)(C)C)S(=O)(=O)c1sccc1Br] |
| 104 | N-[(tert-butoxy)carbonyl]1-benzofuran-2-sulfonamido 2,2-dimethylpropanoate | 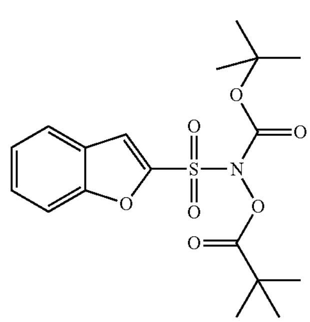 [SMILES: CC(C)(C)OC(=O)N(OC(=O)C(C)(C)C)S(=O)(=O)c1cc2ccccc2o1] |

TABLE 2-continued

Representative compounds of formulae (I), (Ia) and (II):

| Compound No. | Name | Structure |
|---|---|---|
| 105 | N-[(tert-butoxy)carbonyl]1-benzofuran-2-sulfonamido acetate | 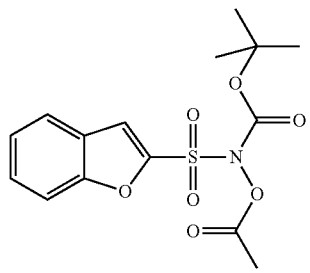 [SMILES: CC(=O)ON(C(=O)OC(C)(C)C)S(=O)(=O)c1cc2ccccc2o1] |
| 106 | N-[(tert-butoxy)carbonyl]3-bromothiophene-2-sulfonamido 2,2-dimethylpropanoate | 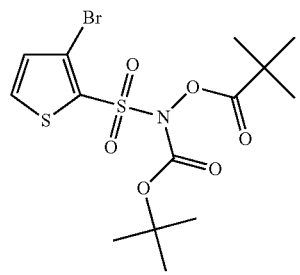 [SMILES: CC(C)(C)OC(=O)N(OC(=O)C(C)(C)C)S(=O)(=O)c1sccc1Br] |
| 107 | N-[(tert-butoxy)carbonyl]3-chlorothiophene-2-sulfonamido 2,2-dimethylpropanoate | 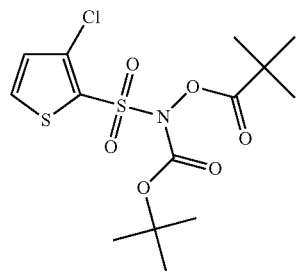 [SMILES: CC(C)(C)OC(=O)N(OC(=O)C(C)(C)C)S(=O)(=O)c1sccc1Cl] |
| 108 | N-[(tert-butoxy)carbonyl]5 chlorothiophene-2-sulfonamido 2-methylpropanoate | 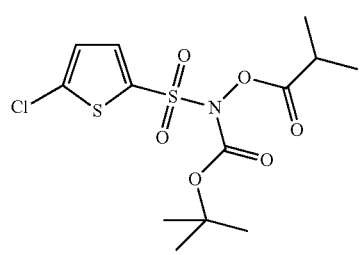 [SMILES: CC(C)C(=O)ON(C(=O)OC(C)(C)C)S(=O)(=O)c1ccc(Cl)s1] |
| 109 | N-[(tert-butoxy)carbonyl]5-chlorothiophene-2-sulfonamido 2,2-dimethylpropanoate | 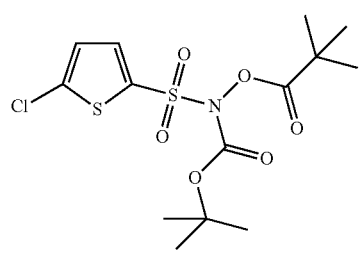 [SMILES: CC(C)(C)OC(=O)N(OC(=O)C(C)(C)C)S(=O)(=O)c1ccc(Cl)s1] |

TABLE 2-continued

Representative compounds of formulae (I), (Ia) and (II):

| Compound No. | Name | Structure |
|---|---|---|
| 110 | N-[(tert-butoxy)carbonyl]pyridine-3-sulfonamido 2,2-dimethylpropanoate | 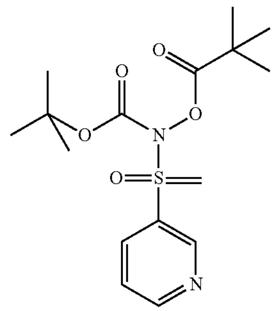 [SMILES: C=S(=O)(c1cccnc1)N(OC(=O)C(C)(C)C)C(=O)OC(C)(C)C] |
| 111 | N-[(tert-butoxy)carbonyl]pyridine-3-sulfonamido 2-methylpropanoate | 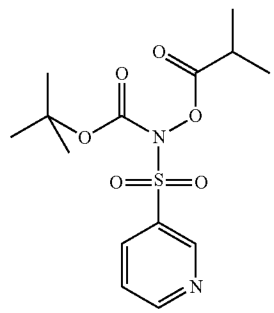 [SMILES: CC(C)C(=O)ON(C(=O)OC(C)(C)C)S(=O)(=O)c1cccnc1] |

[4]Compound 18 was previously reported by H. T. Nagasawa et al., *J. Med. Chem.* 1992, 35, 3648-3652.

In some embodiments, the compound is one that donates nitroxyl under physiological conditions.

For all compounds disclosed herein, where applicable due to the presence of a stereocenter, the compound is intended to embrace all possible stereoisomers of the compound depicted or described. Compositions comprising a compound with at least one stereocenter are also embraced by the invention, and include racemic mixtures or mixtures containing an enantiomeric excess of one enantiomer or single diastereomers or diastereomeric mixtures. All such isomeric forms of these compounds are expressly included herein the same as if each and every isomeric form were specifically and individually listed. The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are also expressly included in the present invention. The compounds herein may also be represented in multiple tautomeric forms, in such instances, the invention expressly includes all tautomeric forms of the compounds described herein, even though only a single tautomeric form may be represented.

In some embodiments, the invention provides a substantially pure compound. "Substantially pure" intends a preparation of the compound that contains no more than 25% of impurity (e.g. by weight %), which impurity maybe another compound altogether or a different form of the compound (e.g. a different salt or isomer). Percent purity may be assessed by methods known in the art. In some embodiments, a preparation of substantially pure compound is provided where the preparation contains no more than 15% of impurity. In some embodiments, a preparation of substantially pure compound is provided where the preparation contains no more than 10% impurity. In some embodiments, a preparation of substantially pure compound is provided where the preparation contains no more than 5% impurity. In some embodiments, a preparation of substantially pure compound is provided where the preparation contains no more than 3% impurity. In some embodiments, a preparation of substantially pure compound is provided where the preparation contains no more than 1% impurity.

In some embodiments, the invention provides a compound in purified and/or isolated form, for example following column chromatography, high-pressure liquid chromatography, recrystallization, or other purification techniques. Where particular stereoisomers of compounds of this invention are denoted, such stereoisomers may be substantially free of other stereoisomers.

Pharmaceutical Compositions

In some embodiments, the invention provides a pharmaceutical composition comprising an effective amount of a compound described herein or a pharmaceutically acceptable salt thereof, together with a pharmaceutically acceptable excipient.

Examples of pharmaceutically acceptable excipients include those described above, such as carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of pharmaceutically acceptable excipients are taught in "Remington: The Science and Practice of Pharmacy", 21st Ed. (Lippincott Williams & Wilkins 2005), the disclosure of which is incorporated herein by reference.

The pharmaceutical compositions may be formulated for administration in solid or liquid form, including those adapted for the following: (1) oral administration, for example, drenches (for example, aqueous or non-aqueous solutions or suspensions), tablets (for example, those targeted for buccal, sublingual and systemic absorption), caplets, boluses, powders, granules, pastes for application to the tongue, hard gelatin capsules, soft gelatin capsules, mouth sprays, troches, lozenges, pellets, syrups, suspensions, elixirs, liquids, emulsions and microemulsions; (2) parenteral administration, for example, by subcutaneous, intramuscular, intravenous or epidural injection as, for example, a sterile solution or suspension; (3) topical application, for example, as a cream, ointment, patch, pad or spray applied to the skin; (4) intravaginally or intrarectally, for example, as a pessary, cream or foam; (5) sublingually; (6) ocularly; (7) transdermally; or (8) nasally. The pharmaceutical compositions may be for immediate, sustained or controlled release.

In some embodiments, the pharmaceutical compositions are formulated for oral administration. In some embodiments, the pharmaceutical compositions are formulated for intravenous administration. In some embodiments, the pharmaceutical compositions are formulated for administration by inhalation.

The compounds and pharmaceutical compositions described herein may be prepared as any appropriate unit dosage form, such as capsules, sachets, tablets; powder, granules, solution, suspension in an aqueous liquid or a non-aqueous liquid, oil-in-water liquid emulsion, water-in-oil liquid emulsion, liposomes and bolus.

Tablets may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets may be optionally coated or scored and may be formulated so as to provide slow or controlled release of the active ingredient therein. Methods of formulating such slow or controlled release compositions of pharmaceutically active ingredients, such as those herein and other compounds known in the art, are known in the art and described in several issued US patents, some of which include, but are not limited to, U.S. Pat. Nos. 4,369,174 and 4,842,866, and references cited therein. Coatings can be used for delivery of compounds to the intestine (see, e.g. U.S. Pat. Nos. 6,638,534, 5,217,720 and 6,569,457, and references cited therein). A skilled artisan will recognize that in addition to tablets, other dosage forms can be formulated to provide slow or controlled release of the active ingredient. Such dosage forms include, but are not limited to, capsules, granulations and gel-caps.

Pharmaceutical compositions suitable for topical administration include, without limitation, lozenges comprising the ingredients in a flavored basis, such as sucrose, *acacia* and tragacanth; and pastilles comprising the active ingredient in a flavored basis or in an inert basis, such as gelatin and glycerin.

Pharmaceutical compositions suitable for parenteral administration include, without limitation, aqueous and non-aqueous sterile injection solutions containing, for example, anti-oxidants, buffers, bacterio stats and solutes that render the formulation isotonic with the blood of the intended recipient; and aqueous and non-aqueous sterile suspensions containing, for example, suspending agents and thickening agents. The formulations may be presented in unit-dose or multi-dose containers, for example, sealed ampules and vials, and may be stored in a freeze dried (lyophilized) condition requiring only the addition of a sterile liquid carrier, such as water, immediately prior to use. In some embodiments, the aqueous composition is acidic, having a pH of about 5.5 to about 7.

Extemporaneous injection solutions and suspensions may be prepared from sterile powders, granules and tablets.

Methods of Using the Compounds and Pharmaceutical Compositions

In some embodiments, the invention provides a method of modulating (such as increasing or reducing) in vivo nitroxyl levels, comprising administering to an individual in need thereof a compound or pharmaceutical composition as described herein. In some embodiments, the individual has, is suspected of having, or is at risk of having or developing a disease or condition that is responsive to nitroxyl therapy.

In some embodiments, the invention provides a method of treating, preventing or delaying the onset and/or development of a disease or condition, comprising administering to an individual (including an individual identified as in need of such treatment, prevention or delay) an effective amount of a compound or pharmaceutical composition as described herein. Identifying an individual in need thereof can be in the judgment of a physician, clinical staff, emergency response personnel or other health care professional and can be subjective (e.g. opinion) or objective (e.g. measurable by a test or diagnostic method).

Particular diseases or conditions embraced by the methods described herein include, without limitation, cardiovascular diseases, ischemia, reperfusion injury, cancerous diseases, pulmonary hypertension and conditions responsive to nitroxyl therapy.

Cardiovascular Diseases

In some embodiments, the invention provides a method of treating a cardiovascular disease, comprising administering an effective amount of a compound or pharmaceutical composition as described herein to an individual in need thereof.

Examples of cardiovascular diseases include, without limitation, cardiovascular diseases that are responsive to nitroxyl therapy, coronary obstructions, coronary artery disease (CAD), angina, heart attack, myocardial infarction, high blood pressure, ischemic cardiomyopathy and infarction, pulmonary congestion, pulmonary edema, cardiac fibrosis, valvular heart disease, pericardial disease, circulatory congestive states, peripheral edema, ascites, Chagas' disease, ventricular hypertrophy, heart valve disease, heart failure, diastolic heart failure, congestive heart failure, acute congestive heart failure, acute decompensated heart failure, and cardiac hypertrophy.

In some embodiments, the individual is experiencing heart failure. In some embodiments, the individual is experiencing heart failure and/or undergoing treatment with a positive inotrope. In some embodiments, the individual is experiencing heart failure and/or undergoing treatment with a beta-andrenergic receptor antagonist (also referred to herein as beta-antagonist or beta-blocker). A beta-antagonist includes any compound that effectively acts as an antagonist at an individual's beta-adrenergic receptors, and provides desired therapeutic or pharmaceutical results, such as diminished vascular tone and/or heart rate. An individual that is undergoing treatment with a beta-antagonist is any individual to whom a beta-antagonist has been administered, and in whom the beta-antagonist continues to act as an antagonist at the individual's beta-adrenergic receptors. Examples of beta-antagonists include, without limitation, propranolol, metoprolol, bisoprolol, bucindolol, and carvedilol.

In some embodiments, the individual is experiencing heart failure and/or undergoing treatment with a beta-adrenergic receptor agonist (also referred to herein as beta-agonist). Examples of beta-agonists include, without limitation, dopamine, dobutamine, isoproterenol, and analogs and derivatives of such compounds.

The determination of whether an individual is undergoing treatment with a positive inotrope, beta-antagonist or beta-agonist may be made by examination of the individual's medical history, or screening of the individual for the presence of such agents by chemical tests, such as high-speed liquid chromatography, as described in Thevis et al., *Biomed. Chromatogr.* 2001, 15, 393-402.

In some embodiments, the method further comprises administering an effective amount of at least one other positive inotrope to the individual. In some embodiments, the method further comprises administering an effective amount of a beta-antagonist to the individual. In some embodiments, the method further comprises administering an effective amount of a beta-agonist to the individual.

In some embodiments, the cardiovascular disease is heart failure. The heart failure may be of any type or form, including any of the heart failures described herein. Non-limiting examples of heart failure include early stage heart failure, Class I, II, III or IV heart failure, acute heart failure, congestive heart failure (CHF) and acute congestive heart failure.

In some embodiments, the cardiovascular disease is CHF, and the method further comprises administering an effective amount of at least one other positive inotropic agent to the individual. In some embodiments, the individual is experiencing heart failure. In some embodiments, the at least one other positive inotrope is a beta-adrenergic agonist. In some embodiments, the beta-adrenergic agonist is dobutamine.

Ischemia or Reperfusion Injury

In some embodiments, the invention provides a method of treating, preventing or delaying the onset and/or development of ischemia or reperfusion injury, comprising administering an effective amount of a compound or pharmaceutical composition as described herein to a subject in need thereof.

In some embodiments, the method is for preventing ischemia or reperfusion injury. In some embodiments, the compound or pharmaceutical composition is administered prior to the onset of ischemia. In some embodiments, the pharmaceutical composition is administered prior to procedures in which myocardial ischemia may occur, for example an angioplasty or surgery, such as a coronary artery bypass graft surgery. In some embodiments, the compound or pharmaceutical composition is administered after ischemia but before reperfusion. In some embodiments, the compound or pharmaceutical composition is administered after ischemia and reperfusion.

In some embodiments, the subject is an individual. In some embodiments, the subject is an individual at risk for an ischemic event. In some embodiments, the individual is at risk for a future ischemic event, but has no present evidence of ischemia. The determination of whether an individual is at risk for an ischemic event can be performed by any method known in the art, such as examining the individual or the individual's medical history. In some embodiments, the individual has had a prior ischemic event. Thus, the individual may be at risk of a first or subsequent ischemic event. Examples of individuals at risk for an ischemic event include individuals with known hypercholesterolemia, EKG changes associated with ischemia (e.g., peaked or inverted T-waves or ST segment elevations or depression in an appropriate clinical context), abnormal EKG not associated with active ischemia, elevated CKMB, clinical evidence of ischemia (e.g., crushing sub-sternal chest pain or arm pain, shortness of breath and/or diaphoresis), prior history of myocardial infarction, elevated serum cholesterol, sedentary lifestyle, angiographic evidence of partial coronary artery obstruction, echocardiographic evidence of myocardial damage, or any other evidence of a risk for a future ischemic event. Examples of ischemic events include, without limitation, myocardial infarction (MI) and neurovascular ischemia, such as a cerebrovascular accident CVA).

In some embodiments, the subject is an organ that is to be transplanted. In some embodiments, the compound or pharmaceutical composition is administered prior to reperfusion of the organ in a transplant recipient. In some embodiments, the compound or pharmaceutical composition is administered prior to removal of the organ from the donor, for example through the perfusion cannulas used in the organ removal process. If the organ donor is a live donor, for example a kidney donor, the compound or pharmaceutical composition can be administered to the organ donor. In some embodiments, the compound or pharmaceutical composition is administered by storing the organ in a solution comprising the compound or pharmaceutical composition. For example, the compound or pharmaceutical composition can be included in the organ preservation solution, such as the University of Wisconsin "UW" solution, which is a solution comprising hydroxyethyl starch substantially free of ethylene glycol, ethylene chlorohydrin and acetone (see, U.S. Pat. No. 4,798,824). In some embodiments, the amount of the compound or pharmaceutical composition is such that ischemia or reperfusion injury to the tissues of the organ is reduced upon reperfusion in the recipient of transplanted organ. In some embodiments, the method reduces tissue necrosis (the size of infarct) in at-risk tissues.

Ischemia or reperfusion injury may damage tissues other than those of the myocardium and the invention embraces methods of treating or preventing such damage. In some embodiments, the ischemia or reperfusion injury is non-myocardial. In some embodiments, the method reduces injury from ischemia or reperfusion in the tissue of the brain, liver, gut, kidney, bowel, or any part of the body other than the myocardium. In some embodiments, the individual is at risk for such injury. Selecting a person at risk for non-myocardial ischemia could include a determination of the indicators used to assess risk for myocardial ischemia. However, other factors may indicate a risk for ischemia/reperfusion in other tissues. For example, surgery patients often experience surgery related ischemia. Thus, individuals scheduled for surgery could be considered at risk for an ischemic event. The following risk factors for stroke (or a subset of these risk factors) could demonstrate an individual's risk for ischemia of brain tissue: hypertension, cigarette smoking, carotid artery stenosis, physical inactivity, diabetes mellitus, hyperlipidemia, transient ischemic attack, atrial fibrillation, coronary artery disease, congestive heart failure, past myocardial infarction, left ventricular dysfunction with mural thrombus, and mitral stenosis. Ingall, *Postgrad. Med.* 2000, 107(6), 34-50. Further, complications of untreated infectious diarrhea in the elderly can include myocardial, renal, cerebrovascular and intestinal ischemia. Slotwiner-Nie et al., *Gastroenterol. Clin. N. Am.* 2001, 30(3), 625-635. Alternatively, individuals could be selected based on risk factors for ischemic bowel, kidney or liver disease. For example, treatment would be initiated in elderly individuals at risk of hypotensive episodes (such as surgical blood loss). Thus, individuals presenting with such an indication would be considered at risk for an ischemic event. In some embodiments, the individual has any one or more of the conditions listed herein, such as diabetes mellitus or hypertension. Other conditions that may result in ischemia, such as cerebral arteriovenous malformation, could demonstrate an individual's risk for an ischemic event.

In some embodiments, the method further comprises administering an additional therapeutic agent. The therapeutic agent may be, for example, a nitroxyl-donating compound, such as Angeli's salt or another compound described herein, a beta-blocker, a calcium channel blocker, an antiplatelet agent or any other therapeutic agent for reducing ischemic injury or for protecting myocardium in the individual.

Cancerous Diseases

In some embodiments, the invention provides a method of treating, preventing or delaying the onset and/or development of a cancerous disease, comprising administering an effective amount of a compound or pharmaceutical composition as described herein to an individual in need thereof.

In some embodiments, the individual has or is suspected of having a cancerous disease, e.g. cancer.

Cancers that may be treated by the methods described herein include, without limitation, cancers of the head and neck, which include tumors of the head, neck, nasal cavity, paranasal sinuses, nasopharynx, oral cavity, oropharynx, larynx, hypopharynx, salivary glands, and paragangliomas; cancers of the liver and biliary tree, such as hepatocellular carcinoma; intestinal cancers, such as colorectal cancer; ovarian cancer; small cell and non-small cell lung cancer; breast cancer sarcomas, such as fibrosarcoma, malignant fibrous histiocytoma, embryonal rhabdomysocarcoma, leiomysosarcoma, neurofibrosarcoma, osteosarcoma, synovial sarcoma, liposarcoma, and alveolar soft part sarcoma; neoplasms of the central nervous systems, such as brain cancer; lymphomas such as Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma.

In some embodiments, the method further comprises administering an effective amount of an additional therapeutic agent to the individual. In some embodiments, the additional therapeutic agent is an anti-cancer agent or a cytotoxic agent. Examples of such agents include, without limitation, alkylating agents, angiogenesis inhibitors, antimetabolites, DNA cleavers, DNA crosslinkers, DNA intercalators, DNA minor groove binders, enediynes, heat shock protein 90 inhibitors, histone deacetylase inhibitors, microtubule stabilizers, nucleoside (purine or pyrimidine) analogs, nuclear export inhibitors, proteasome inhibitors, topoisomerase (I or II) inhibitors, tyrosine kinase inhibitors. Specific anti-cancer or cytotoxic agents include, for example, beta.-lapachone, ansamitocin P3, auristatin, bicalutamide, bleomycin, bleomycin, bortezomib, busulfan, calicheamycin, callistatin A, camptothecin, capecitabine, cisplatin, cryptophycins, daunorubicin, docetaxel, doxorubicin, duocarmycin, dynemycin A, etoposide, floxuridine, floxuridine, fludarabine, fluoruracil, gefitinib, gemcitabine, hydroxyurea, imatinib, interferons, interleukins, irinotecan, methotrexate, mitomycin C, oxaliplatin, paclitaxel, spongistatins, suberoylanilide hydroxamic acid (SAHA), thiotepa, topotecan, trichostatin A, vinblastine, vincristine and vindesine.

Pulmonary Hypertension

In some embodiments, the invention provides a method of treating, preventing or delaying the onset and/or development of pulmonary hypertension, comprising administering an effective amount of a compound or pharmaceutical composition as described herein to an individual in need thereof. In some embodiments, the pulmonary hypertension is selected from the diseases and conditions listed above in Table 1. In some embodiments, the pulmonary hypertension is pulmonary arterial hypertension (PAH). In some embodiments, the pulmonary hypertension is pulmonary hypertension owing to left heart disease. In some embodiments, the left heart disease is left heart failure. In some embodiments, the left heart failure is systolic heart failure. In some embodiments, the left heart failure is diastolic heart failure. In some embodiments, the left heart failure is chronic or acutely decompensated. In some embodiments, the pulmonary hypertension is chronic thromboembolic pulmonary hypertension.

In some embodiments, the invention provides a method of reducing mean pulmonary arterial pressure (MPAP), comprising administering an effective amount of a compound or a pharmaceutical composition described herein to an individual in need thereof. In some embodiments, the MPAP is reduced by up to about 50%. In some embodiments, the MPAP is reduced by up to about 25%. In some embodiments, the MPAP is reduced by up to 20%. In some embodiments, the MPAP is reduced by up to 15%. In some embodiments, the MPAP is reduced by up to 10%. In some embodiments, the MPAP is reduced by up to 5%. In some embodiments, the MPAP is reduced to about 12 to 16 mmHg. In some embodiments, the MPAP is reduced to about 15 mmHg.

Administration Modes, Regimens and Dose Levels

Any administration regimen well known to those skilled in the art for regulating the timing and sequence of drug delivery can be used and repeated as necessary to effect treatment in the methods described herein. For example, the compound or pharmaceutical composition may be administered 1, 2, 3 or 4 times daily, by a single dose, multiple discrete doses or continuous infusion.

The compound or pharmaceutical composition may be administered prior to, at substantially the same time with, or after administration of an additional therapeutic agent. The administration regimen may include pretreatment and/or co-administration with the additional therapeutic agent. In such case, the compound or pharmaceutical composition and the additional therapeutic agent may be administered simultaneously, separately, or sequentially.

Examples of administration regimens include without limitation:

administration of each compound, pharmaceutical composition and therapeutic agent in a sequential manner; and co-administration of each compound, pharmaceutical composition and therapeutic agent in a substantially simultaneous manner (e.g., as in a single unit dosage form) or in multiple, separate unit dosage forms for each compound, pharmaceutical composition and therapeutic agent.

Administration of the compound or pharmaceutical composition may be via any accepted mode known to one skilled in the art, for example, orally, parenterally, by inhalation spray, topically, rectally, nasally, buccally, vaginally, intraocularly, intrapulmonarily, or via an implanted reservoir. The term "parenterally" includes without limitation subcutaneously, intravenously, intramuscularly, intraperitoneally, intrathecally, intraventricularly, intrasternally, intracranially, by intraosseous injection and by infusion techniques. Administration may involve systemic exposure or may be local, such as when a compound or pharmaceutical composition is administered at the site of interest. Various tools can be used for administering at the site of interest, such as catheters, trocars, projectiles, pluronic gels, stems, sustained drug release polymers or other devices which provide for internal access. Where the compound or pharmaceutical composition is administered to an organ to be donated, such organ may be bathed in a medium containing the compound or pharmaceutical composition. Alternatively, the compound or pharmaceutical composition may be painted onto the organ, or may be applied in any suitable manner.

It will be appreciated by those skilled in the art that the "effective amount" or "dose level" will depend on various factors such as the particular administration mode, administration regimen, compound, and composition selected, and the particular disease and patient being treated. For example, the appropriate dose level may vary depending upon the activity, rate of excretion and possible toxicity of the specific compound or composition employed; the age, body weight, general health, gender and diet of the patient being treated; the frequency of administration; the other therapeutic agent(s) being co-administered; and the type and severity of the disease.

The compounds and pharmaceutical compositions described herein may be administered at suitable dose level. In some embodiments, the compound or pharmaceutical composition is administered at a dose level of about 0.0001 to 4.0 grams once per day (or multiple doses per day in divided doses) for adults. Thus, in some embodiments, the compound or pharmaceutical composition is administered at a dose level range in which the low end of the range is any amount between 0.1 mg/day and 400 mg/day and the high end of the range is any amount between 1 mg/day and 4000 mg/day (e.g., 5 mg/day and 100 mg/day, 150 mg/day and 500 mg/day). In some embodiments, the compound or pharmaceutical composition is administered at a dose level range in which the low end of the range is any amount between 0.1 mg/kg/day and 90 mg/kg/day and the high end of the range is any amount between 1 mg/kg/day and 100 mg/kg/day (e.g., 0.5 mg/kg/day and 2 mg/kg/day, 5 mg/kg/day and 20 mg/kg/day).

In some embodiments, the compound or pharmaceutical composition is administered at a weight base dose. In some embodiments, the dose level is about 0.001 to about 10,000 mg/kg/d. In some embodiments, the dose level is about 0.01 to about 1,000 mg/kg/d. In some embodiments, the dose level is about 0.01 to about 100 mg/kg/d. In some embodiments, the dose level is about 0.01 to about 10 mg/kg/d. In some embodiments, the dose level is about 0.1 to about 1 mg/kg/d. In some embodiments, the dose level is less than about 1 g/kg/d.

The dose level can be adjusted for intravenous administration. In such case, the compound or pharmaceutical composition can be administered in an amount of between about 0.01 µg/kg/min to about 100 µg/kg/min, about 0.05 µg/kg/min to about 95 µg/kg/min, about 0.1 µg/kg/min to about 90 µg/kg/min, about 1.0 µg/kg/min to about 80 µg/kg/min, about 10.0 µg/kg/min to about 70 µg/kg/min, about 20 µg/kg/min to about 60 µg/kg/min, about 30 µg/kg/min to about 50 µg/kg/min, about 0.01 µg/kg/min to about 1.0 µg/kg/min, about 0.01 µg/kg/min to about 10 µg/kg/min, about 0.1 µg/kg/min to about 1.0 µg/kg/min, about 0.1 µg/kg/min to about 10 µg/kg/min, about 1.0 µg/kg/min to about 5 µg/kg/min, about 70 µg/kg/min to about 100 µg/kg/min, about 80 µg/kg/min to about 90 µg/kg/min.

The dosing interval can be adjusted according to the needs of the individual. For longer intervals of administration, extended release or depot formulations can be used.

Kits Comprising the Compounds or Pharmaceutical Compositions

In some embodiments, the invention provides a kit comprising a compound or a pharmaceutical composition described herein.

In some embodiments, the kit further comprises instructions for using the compound or pharmaceutical composition. The instructions may be in any appropriate form, such as written or electronic form. In some embodiments, the instructions may be written instructions. In some embodiments, the instructions are contained in an electronic storage medium (e.g., magnetic diskette or optical disk). In some embodiments, the instructions include information as to the compound or pharmaceutical composition and the manner of administering the compound or pharmaceutical composition to an individual. In some embodiments, the instructions relate to a method of use described herein (e.g., treating, preventing and/or delaying onset and/or development of a disease or condition selected from cardiovascular diseases, ischemia, reperfusion injury, cancerous disease, pulmonary hypertension and conditions responsive to nitroxyl therapy).

In some embodiments, the kit further comprises suitable packaging. Where the kit comprises more than one compound or pharmaceutical composition, the compounds or pharmaceutical compositions may be packaged individually in separate containers, or combined in one container where cross-reactivity and shelf life permit.

Other than in the working examples, or where otherwise indicated, all numbers expressing quantities of ingredients, reaction conditions, and so forth used in the specification and claims are to be understood as being modified by the term "about". Accordingly, unless indicated to the contrary, such numbers are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding techniques.

While the numerical ranges and parameters setting forth the broad scope of the invention are approximations, the numerical values set forth in the working examples are reported as precisely as possible. Any numerical value, however, inherently contains certain errors necessarily resulting from the standard deviation found in their respective testing measurements.

EXAMPLES

The following examples are presented for illustrative purposes and should not serve to limit the scope of the invention.

General Synthetic Methods

All NMR are recorded on one of the following instruments; Bruker AVANCE 400 MHz spectrometer, Bruker 250, 360 or 500 operating at ambient probe temperature using an internal deuterium lock. Chemical shifts are reported in parts per million (ppm) at lower frequency relative to tetramethylsilane (TMS). Standard abbreviations are used throughout (s: singlet; br. s: broad singlet; d:

doublet; dd: doublet of doublets; t: triplet; q: quartet; quin: quintet; m: multiplet). Coupling constants are reported in Hertz (Hz).

Example 1

Synthesis of Compounds 1-15

N-Halo-N-acyloxy-amides (1-15)

N,O-bis-acylated hydroxylamines are synthesized by known literature methods. The N,O-bis-acylated hydroxylamine is dissolved in dichloromethane and 0.5 equivalents (equiv) of trihaloisocyanuric acid is added in the dark. Upon completion of the reaction (as indicated by TLC), the solution is filtered through celite. The filtrate is evaporated under reduced pressure at room temperature to give the desired products in typically 90-100% yield.

N-Chloro-N-benzoyloxy-benzamide (1)

$^1$H NMR (400 MHz, δ) 7.39 (4H, m), 7.49 (1H, m), 7.59 (1H, m), 7.79 (2H, d), 7.89 (12H, d); $^{13}$C NMR (100 MHz, δ) 125.98, 128.58, 128.90, 129.35, 129.94, 130.02, 133.23, 134.83, 163.36, 173.51; IR (KBr, cm$^{-1}$) 1730.0, 1770.2.

N-Chloro-N-(4-chlorobenzoyloxy)-4-chlorobenzamide (2)

$^1$H NMR (400 MHz, δ) 7.38 (2H, d), 7.40 (2H, d), 7.73 (2H, d), 7.86 (2H, d); IR (KBr, cm$^{-1}$) 1733.1, 1770.0.

N-Chloro-N-(4-nitrobenzoyl)-4-nitrobenzamide (3)

$^1$H NMR (400 MHz, δ) 7.99 (2H, d), 8.16 (2H, d), 8.30 (4H, m); IR (KBr, cm$^{-1}$) 1732.8, 1770.0.

N-Chloro-N-(4-nitrobenzoyl)-benzamide (4)

$^1$H NMR (400 MHz, δ) 7.34 (2H, m), 7.47 (1H, m), 7.71 (2H, d), 8.03 (2H, d), 8.19 (2H, d).

N-Chloro-N-(2,6-difluorobenzoyl)-benzamide (5)

$^1$H NMR (400 MHz, δ) 6.91 (2H, t) 7.40 (2H, m), 7.46 (1H, t), 7.52 (1H, t), 7.77 (2H, d).

N-Chloro-N-acetoxy-benzamide (6)

$^1$H NMR (400 MHz, δ) 1.99 (1H, s), 7.41 (2H, m), 7.54 (1H, m), 7.71 (2H, d); IR (KBr, cm$^{-1}$) 1722.2, 1804.1.

N-Chloro-N-dichloroacetyloxy-benzamide (7)

$^1$H NMR (400 MHz, δ) 7.48 (2H, m), 7.60 (1H, m), 7.78 (2H, d); IR (KBr, cm$^{-1}$) 1736.0, 1811.9.

N-Chloro-N-acetyloxy-acetamide (9)

$^1$H NMR (400 MHz, δ) 2.13 (3H, s), 2.17 (3H, s); IR (KBr, cm$^{-1}$) 1732.9, 1805.1.

N-Chloro-N-acetyloxy-tert-butyl-carbamate (10)

$^1$H NMR (400 MHz, δ) 1.51 (9H, s), 2.16 (3H, s); $^{13}$C NMR (100 MHz, δ) 18.49, 27.59, 86.76, 155.63, 167.32; IR (KBr, cm$^{-1}$) 1764.6, 1804.4.

N-Chloro-N-ethyl-carbonoxy-ethyl-carbamate (11)

$^1$H NMR (400 MHz, δ) 1.37 (6H, q), 4.37 (4H, t); IR (KBr, cm$^{-1}$) 1772.6, 1799.9.

N-Chloro-N-(trimethylacetyloxy)-trimethylacetamide (12)

$^1$H NMR (400 MHz, δ) 1.26 (9H, s), 1.28 (9H, s).

N-Chloro-N-(4-nitrobenzoyloxy)-tert-butyl-carbamate (13)

$^1$H NMR (400 MHz, δ) 1.53 (9H, s), 8.24 (2H, d), 8.32 (2H, d); $^{13}$C NMR (100 MHz, δ) 27.60, 87.53, 123.92, 131.26, 132.07, 151.28, 155.41, 161.74; IR (KBr, cm$^{-1}$) 1753.7, 1780.0.

N-Chloro-N-(acetyloxy)-trimethylacetamide (14)

$^1$H NMR (400 MHz, δ) 1.27 (9H, s), 2.21 (3H, s); $^{13}$C NMR (100 MHz, δ) 18.72, 27.48, 41.26, 166.26, 181.47; IR (KBr, cm$^{-1}$) 1731.3, 1811.0.

N-Bromo-N-acetyloxy-acetamide (15)

$^1$H NMR (400 MHz, δ) 2.21 (3H, s), 2.26 (3H, s); $^{13}$C NMR (100 MHz, δ) IR (KBr, cm$^{-1}$) 1702.7, 1798.0.

Example 2

Synthesis of Compounds 18-33

N-Sulfonyl-N-acyloxy-amides (18-33)

To N-sulfonyl-N-acyloxy-tert-butyl-carbamate (see protocol for 36-40 below), 5 equivalents trifluoroacetic acid are added and the mixture is stirred for five minutes. The mixture is washed several times with hexane. The resultant N-acyloxy-sulfonamide is purified by column chromatography. To a solution of the N-acyloxy-sulfonamide stirring in tetrahydrofuran, 1.1 equivalents of triethylamine is added. After five minutes, 1.1 equivalents of an appropriate acid chloride is added and the solution is stirred until completion of the reaction (as indicated by TLC). The solvent is removed under reduced pressure and the crude product is purified by column chromatography.

N-(4-Chlorobenzenesulfonyl)-N-acetyloxy-acetamide (18)[5]

$^1$H NMR (400 MHz, δ) 2.19 (3H, s), 2.30 (3H, s), 7.54 (2H, d), 7.97 (2H, d); $^{13}$C NMR (100 MHz, δ) 17.99, 22.60, 129.57, 130.73, 135.65, 141.78, 167.19, 167.68; IR (KBr, cm$^{-1}$) 1723.5, 1811.9.

[5] Compound 18 was previously reported by H. T. Nagasawa et al., *J. Med. Chem.* 1992, 35, 3648-3652.

N-(2-Bromobenzenesulfonyl)-N-acetyloxy-acetamide (19)

$^1$H NMR (400 MHz, δ) 2.20 (3H, s), 2.41 (3H, s), 7.51 (2H, m), 7.76 (1H, m), 8.22 (1H, m); $^{13}$C NMR (100 MHz, δ) 17.84, 23.48, 121.01, 127.97, 133.62, 135.53, 136.03, 136.50, 166.45, 166.56; IR (KBr, cm$^{-1}$) 1723.3, 1811.9; FAB-MS 335.95413 (M+H) (335.95347 cal.).

N-(2-Chlorobenzenesulfonyl)-N-acetyloxy-acetamide (20)

$^1$H NMR (400 MHz, δ) 2.18 (3H, s), 2.37 (3H, s), 7.46 (1H, t), 7.56 (2H, m), 8.16 (1H, d); $^{13}$C NMR (100 MHz, δ): 17.69, 23.24, 127.38, 132.36, 132.89, 133.13, 134.64, 135.64, 166.38, 166.53; IR (KBr, cm$^{-1}$) 1722.2, 1816.2; FAB-MS 292.00380 (M+H $^{35}$Cl) (292.00465), 294.00236 (M+H $^{37}$Cl) (294.00 170 cal.).

N-(2-Bromo-4,6-difluoro-benzenesulfonyl)-N-acetyloxy-acetamide (21)

$^1$H NMR (400 MHz, δ) 2.26 (3H, s), 2.47 (3H, s), 7.00 (1H, dd), 7.41 (1H, d); IR (KBr, cm$^{-1}$) 1728.9, 1815.9; FAB-MS 371.93531 (M+H $^{79}$Br) (371.93529 cal.).

N-(2,6-Dibromobenzenesulfonyl)-N-acetyloxy-acetamide (22)

$^1$H NMR (400 MHz, δ) 2.24 (3H, s), 2.45 (3H, s), 7.26 (1H, t), 2.81 (2H, d); $^{13}$C NMR (100 MHz, δ) 17.75, 23.46, 124.45, 134.76, 134.85, 136.48, 166.04, 166.27; IR (KBr, cm$^{-1}$) 1722.6, 1813.6; FAB-MS 413.86393 (M+H 2×$^{79}$Br) (413.86464 cal.).

N-(2,6-Dichlorobenzenesulfonyl)-N-acetyloxy-acetamide (23)

$^1$H NMR (400 MHz, δ) 2.24 (3H, s), 2.44 (3H, s), 7.45 (1H, t), 7.52 (2H, d); $^{13}$C NMR (100 MHz, δ) 17.77, 23.41, 131.55, 132.30, 134.45, 136.93; IR (KBr, cm$^{-1}$) 1718.8, 1813.6; FAB-MS 325.96597 (M+H $^{35}$Cl) (325.96567 cal.).

N-(2,6-Difluorobenzenesulfonyl)-N-acetyloxy-acetamide (24)

$^1$H NMR (400 MHz, δ) 2.23 (3H, s), 2.43 (3H, s), 7.10 (2H, m), 7.67 (1H, m); $^{13}$C NMR (100 MHz, δ) 17.60, 23.05, 113.5 (multiple F coupling), 137.24, 158.72, 161.32, 166.18, 166.34; IR (KBr, cm$^{-1}$) 1738.7, 1809.5; FAB-MS 294.02434 (M+H) (294.02478).

N-(2-Nitrobenzenesulfonyl)-N-acetyloxy-acetamide (25)

$^1$H NMR (400 MHz, δ) 2.29 (3H, s), 2.32 (3H, s), 7.78 (3H, m), 8.30 (1H, d); $^{13}$C NMR (100 MHz, δ) 17.74, 22.72, 124.84, 130.31, 132.29, 133.63, 135.81, 148.10, 166.86, 167.16; IR (KBr, cm$^{-1}$) 1728.8, 1813.5; FAB-MS 303.02861 (M+H) (303.02870 cal.).

N-(Chloromethylsulfonyl)-N-acetyloxy-acetamide (26)

$^1$H NMR (400 MHz, δ) 2.23 (3H, s), 2.26 (3H, s), 4.91 (2H, d); $^{13}$C NMR (100 MHz, δ) 17.56, 22.15, 56.49, 167.17, 168.27; IR (KBr, cm$^{-1}$) 1734.8, 1818.5.

N-(2,6-Dichlorobenzenesulfonyl)-N-acetyloxy-benzamide (28)

$^1$H NMR (400 MHz, δ) 2.19 (3H, s), 7.47 (6H, m), 7.78 (2H, d); IR (KBr, cm$^{-1}$) 1719.3, 1813.5; FAB-MS 387.98177 (M+H 2×$^{35}$Cl) (387.98132 cal.).

N-(2,6-Dichlorobenzenesulfonyl)-N-acetyloxy-benzyl-carbamate (29)

$^1$H NMR (400 MHz, δ) 2.22 (1H, s), 2.32 (2H, s), 5.23 (2H, s), 7.20-7.45 (8H, m); IR (KBr, cm$^{-1}$) 1762.4, 1815.4.

N-(2,6-Dichlorobenzenesulfonyl)-N-acetyloxy-dichloroacetamide (30)

$^1$H NMR (400 MHz, δ) 2.24 (3H, s), 6.65 (1H, s), 7.49 (3H, m); $^{13}$C NMR (100 MHz, δ) 17.58, 64.10, 132.19, 135.48, 136.91, 160.43, 165.88, 168.39; IR (KBr, cm$^{-1}$) 1732.9, 1825.5; FAB-MS 393.88707 (M+H) (393.8873).

N-(2,5-Dichlorobenzenesulfonyl)-N-acetyloxy-trimethylacetamide (31)

$^1$H NMR (400 MHz, δ) 1.30 (9H, s), 2.37 (3H, s), 7.51 (2H, d), 7.55 (2H, d), 8.20 (1H, s); $^{13}$C NMR (100 MHz, δ) 23.02, 26.62, 38.39, 131.17, 133.00, 133.33, 133.41, 135.34, 136.12, 166.55, 173.84; IR (KBr, cm$^{-1}$) 1717.2, 1796.2; FAB-MS 368.01253 (M+H 2×$^{35}$Cl) (368.01263 cal.). N-(2-Nitrobenzenesulfonyl)-N-acetyloxy-trimethylacetamide (32). $^1$H NMR (400 MHz, δ) 1.25 (9H, s), 2.25 (3H, s), 7.65-7.80 (3H, m), 8.25 (1H, d); IR (KBr, cm$^{-1}$) 1728.6, 1798.4.

N-(2,6-Dichlorobenzenesulfonyl)-N-acetyloxy-trimethylacetamide (33)

$^1$H NMR (400 MHz, δ) 1.19 (9H, s), 2.39 (3H, s), 7.39 (1H, m), 7.50 (2H, d); IR (KBr, cm$^{-1}$) 1692.4, 1812.1.

Example 3

Synthesis of Compounds 36-40

N-Sulfonyl-N-acyloxy-tert-butyl-carbamates (36-40)

N-Acyloxy-tert-butyl-carbamate is dissolved in anhydrous tetrahydrofuran and 1.05 equivalents of sodium hydride is added. The solution is stirred for five minutes until gas evolution is complete. To this solution 0.95 equivalents of an appropriate sulfonyl chloride is added and stirred until the reaction is complete (as indicated by TLC). The solvent is removed under reduced pressure and the crude product is purified by column chromatography.

N-(2-Bromobenzenesulfonyl)-N-acetyloxy-tert-butyl-carbamate (36)

$^1$H NMR (400 MHz, δ) 1.38 (9H, s), 2.33 (3H, s), 7.52 (2H, m), 7.80 (1H, d), 8.27 (1H, d).

N-(2,6-Dichlorobenzenesulfonyl)-N-acetyloxy-tert-butyl-carbamate (37)

$^1$H NMR (400 MHz, δ) 1.37 (9H, s), 2.29 (3H, s), 7.44-7.51 (3H, m); $^{13}$C NMR (100 MHz, δ) 17.60, 27.73, 86.91, 131.61, 133.81, 134.25, 136.44, 147.89, 167.20; IR (KBr, cm$^{-1}$) 1766.6, 1815.5.

N-(2,6-Dibromobenzenesulfonyl)-N-acetyloxy-tert-butyl-carbamate (38)

$^1$H NMR (400 MHz, δ) 1.28 (9H, s), 2.21 (3H, s), 7.21 (1H, t), 7.74 (2H, d); $^{13}$C NMR (100 MHz, δ) 17.94, 27.37,

N-(Methanesulfonyl)-N-4-nitrobenzoyloxy-tert-butyl-carbamate (39)

$^1$H NMR (400 MHz, δ) 1.52 (9H, s), 3.49 (3H, s), 8.27 (2H, d), 8.31 (2H, d); $^{13}$C NMR (100 MHz, δ) 27.85, 42.07, 87.40, 123.96, 131.22, 131.55, 148.72, 151.43, 162.78; IR (KBr, cm$^{-1}$) 1762.2, 1795.0.

N-(2,6-Dichlorobenzenesulfonyl)-N-4-nitrobenzoyloxy)-tert-butyl-carbamate (40)

$^1$H NMR (400 MHz, δ) 1.39 (9H, s), 7.50-7.56 (3H, m), 8.33 (4H, m); $^{13}$C NMR (100 MHz, δ) 27.76, 87.65, 123.93, 131.47, 131.64, 131.77, 134.02, 134.11, 136.52, 147.86, 151.33, 162.00.

Example 4

Synthesis of Compounds 41-47, 50, 51, 53-78, 103-111

Synthesis of N,O Disubstituted Hydroxylamine Intermediates (Scheme 1)

Scheme 1

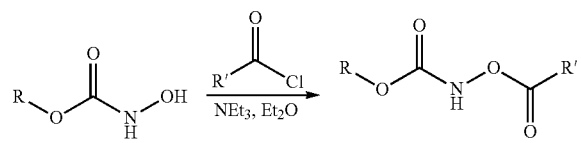

To a stirred solution of N-hydroxy carbamate (1 equiv) in diethyl ether (50 vol) cooled to 0° C. is sequentially added triethylamine (1 equiv) and a solution of an acid chloride (1 equiv) in diethyl ether. The reaction mixture is stirred at 0° C. until complete consumption of the starting material is observed by tlc after which time the reaction is filtered to remove triethylamine hydrochloride and the resulting filtrate is washed with sodium bicarbonate solution (10 vol). The resulting organics are dried over sodium sulfate, filtered and concentrated in vacuo. The crude material is either used directly without additional purification or purified by column chromatography eluting with heptane: ethyl acetate.

Synthesis of Compounds from N,O Disubstituted Hydroxylamine Intermediate (Scheme 2)

Scheme 2

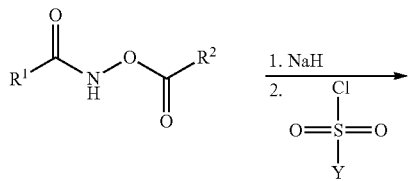

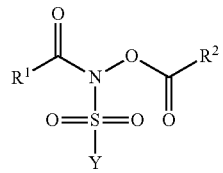

All compounds are synthesized via standard methods using the general method detailed by H. T. Nagasawa et al., *J. Med. Chem.* 1992, 35, 3648-3652. A solution of N,O-disubstituted hydroxylamine (1 equiv) in THF (5 vol) is added dropwise to a stirred solution of sodium hydride (60% dispersion in oil, 1 equiv) in THF (5 vol). Stirring is continued for 30 minutes, whereupon a sulfonyl chloride (1 equiv) is added. The reaction is stirred at room temperature until all starting material is consumed (monitored by tlc). The reaction is quenched by the addition of water (10 vol) and extracted into ether (30 vol). The combined organics are dried over sodium sulfate, filtered and concentrated in vacuo to yield the desired material, which is purified by silica column chromatography eluting with heptane: ethyl acetate.

Preparation of tert-butyl(acetyloxy)[(2-bromophenyl)sulfonyl]carbamate (41)

[(tert-Butoxy)carbonyl]amino acetate is prepared from acetyl chloride and N-tert-butoxycarbonyl hydroxylamine according to Scheme 1 and the method described by Carpino et al. *J. Am. Chem. Soc.* 1959, 955-957. (10 g, 100%), $^1$H NMR (500 MHz, DMSO-d$_6$) δ ppm 10.57 (1H, br. s.), 2.10 (3H, s), 1.41 (9H, s).

tert-Butyl(acetyloxy)[(2-bromophenyl)sulfonyl]carbamate (41) is prepared according to Scheme 2. A solution of [(tert-butoxy)carbonyl]amino acetate (0.68 g, 3.9 mmol) in THF (5 ml) is added dropwise to a stirred solution of sodium hydride (0.16 g of a 60% dispersion, 3.9 mmol) in THF (10 ml). Stirring is continued for 30 minutes, whereupon 2-bromobenzene sulfonyl chloride (1.0 g, 3.9 mmol) is added. The reaction mixture is stirred at room temperature for 3 hours after which time tlc (1:1 heptane: ethyl acetate) shows no starting material remains. The reaction mixture is quenched by the addition of water (30 ml) and extracted into ether (2×50 ml). The combined organics are dried over sodium sulfate, filtered and concentrated in vacuo to yield the desired material as a yellow oil, which is purified by silica column chromatography eluting with heptane: ethyl acetate (4:1; v:v). (0.96 g, 60%), $^1$H NMR (360 MHz, DMSO-d6) δ ppm 8.12-8.26 (1H, m), 7.87-8.06 (1H, m), 7.61-7.79 (2H, m), 2.32 (3H, s), 1.26 (9H, s).

Preparation of tert-butyl(acetyloxy){[2-(methylsulfonyl)phenyl]sulfonyl}carbamate (42)

tert-Butyl(acetyloxy){[2-(methylsulfonyl)phenyl]sulfonyl}carbamate (42) is prepared from 2-methylsulfonylbenzenesulfonyl chloride, sodium hydride and [(tert-butoxy)carbonyl]amino acetate according to Scheme 2. (0.5 g, 16%), $^1$H NMR (400 MHz, DMSO-d6) δ ppm 8.26-8.34 (1H, m), 8.17-8.25 (1H, m), 8.03-8.11 (2H, m), 3.46 (3H, s), 2.32 (3H, s), 1.28 (9H, s).

Preparation of tert-butyl(acetyloxy)[(3-bromothiophen-2-yl)sulfonyl]carbamate (43)

tert-Butyl(acetyloxy)[(3-bromothiophen-2-yl)sulfonyl]carbamate (43) is prepared from 3-bromothiophene-2-sulfonyl chloride, sodium hydride and [(tert-butoxy)carbonyl] amino acetate according to Scheme 2. (0.8 g, 35%), $^1$H NMR (250 MHz, CHLOROFORM-d) δ ppm 7.68 (1H, d, 5.3 Hz), 7.15 (1H, d, 5.2 Hz), 2.30 (3H, s), 1.48 (9H, s).

Preparation of tert-butyl {[2-(methylsulfonyl)phenyl]sulfonyl}(propanoyloxy)carbamate (44)

[(tert-Butoxy)carbonyl]amino propanoate is prepared from propionyl chloride and N-tert-butoxycarbonyl hydroxylamine according to Scheme 1 described by Carpino et al. *J. Am. Chem. Soc.* 1959, 955-957. (3.4 g, 48%), $^1$H NMR (250 MHz, DMSO-$d_6$) δ ppm 10.57 (1H, br. s.), 2.40 (2H, q, 7.5 Hz), 1.40 (9H, s), 1.07 (3H, t, 7.4 Hz).

tert-Butyl{[2-(methylsulfonyl)phenyl]sulfonyl}(propanoyloxy)carbamate (44) is prepared from 2-methylsulfonylbenzenesulfonyl chloride, sodium hydride and [(tert-butoxy)carbonyl]amino propanoate according to Scheme 2. (1.09 g, 68%), $^1$H NMR (250 MHz, DMSO-d6) δ ppm 8.16-8.37 (2H, m), 8.00-8.15 (2H, m), 3.46 (3H, s), 2.61 (2H, q, 7.5 Hz), 1.29 (9H, s), 1.15 (3H, t, 7.5 Hz).

Preparation of tert-butyl[(2-methylpropanoyl)oxy]{[2-(methylsulfonyl)phenyl]sulfonyl}carbamate (45)

[(tert-Butoxy)carbonyl]amino 2-methylpropanoate is prepared from isobutyryl chloride and N-tert-butoxycarbonyl hydroxylamine according to Scheme 1 using the method described by Carpino et al. *J. Am. Chem. Soc.* 1959, 955-957. (6.36 g, 83%), $^1$H NMR (250 MHz, DMSO-$d_6$) δ ppm 10.51 (1H, br. s.), 2.65 (1H, sept, 7.0 Hz), 1.40 (9H, s), 1.13 (6H, d, 7.0 Hz).

tert-Butyl [(2-methylpropanoyl)oxy]{[2-(methylsulfonyl)phenyl]sulfonyl}carbamate (45) is prepared from 2-methylsulfonylbenzenesulfonyl chloride, sodium hydride and [(tert-butoxy)carbonyl]amino 2-methylpropanoate according to Scheme 2. (1.2 g, 72%), $^1$H NMR (250 MHz, DMSO-d6) δ ppm 8.18-8.34 (2H, m), 8.00-8.14 (2H, m), 3.46 (3H, s), 2.86 (1H, sept, 7.1 Hz), 1.29 (9H, s), 1.21 (6H, d, 7.0 Hz).

Preparation of tert-butyl[(2,2-dimethylpropanoyl)oxy]{[2-(methylsulfonyl)phenyl]sulfonyl}carbamate (46)

[(tert-Butoxy)carbonyl]amino 2,2-dimethylpropanoate is prepared from trimethyl acetyl chloride and N-tert-butoxycarbonyl hydroxylamine according to Scheme 1 described by Carpino et al. *J. Am. Chem. Soc.* 1959, 955-957. (6.4 g, 78%), $^1$H NMR (250 MHz, DMSO-$d_6$) δ ppm 10.46 (1H, br. s.), 1.40 (9H, s), 1.20 (9H, s).

tert-Butyl [(2,2-dimethylpropanoyl)oxy]{[2-(methylsulfonyl)phenyl]sulfonyl}carbamate (46) is prepared from 2-methylsulfonylbenzenesulfonyl chloride, sodium hydride and [(tert-butoxy)carbonyl]amino 2,2-dimethylpropanoate according to Scheme 2. (1.5 g, 78%), $^1$H NMR (250 MHz, DMSO-d6) δ ppm 8.18-8.37 (2H, m), 7.94-8.15 (2H, m), 3.46 (3H, s), 1.30 (9H, s), 1.29 (9H, s).

Preparation of tert-butyl {[2-(methylsulfonyl)phenyl]sulfonyl}[(phenyl carbonyl)oxy]carbamate (47)

[(tert-Butoxy)carbonyl]amino benzoate is prepared from benzoyl chloride and N-tert-butoxycarbonyl hydroxylamine according to Scheme 1 described by Carpino et al. *J. Am. Chem. Soc.* 1959, 955-957. (7.2 g, 80%), $^1$H NMR (250 MHz, DMSO-$d_6$) δ ppm 10.89 (1H, br. s.), 7.90-8.12 (2H, m), 7.68-7.82 (1H, m), 7.51-7.65 (2H, m), 1.43 (9H, s).

tert-Butyl {[2-(methylsulfonyl)phenyl]sulfonyl}[(phenylcarbonyl)oxy]carbamate (47) is prepared from 2-methylsulfonylbenzenesulfonyl chloride, sodium hydride and [(tert-butoxy)carbonyl]amino benzoate according to Scheme 2. (1.7 g, 91%), $^1$H NMR (250 MHz, DMSO-d6) δ ppm 8.25-8.45 (2H, m), 8.03-8.20 (4H, m), 7.77-7.93 (1H, m), 7.59-7.73 (2H, m), 3.48 (3H, s), 1.29 (9H, s).

Preparation of benzyl (acetyloxy){[2-(methylsulfonyl)phenyl]sulfonyl}carbamate (50)

[(Benzyloxy)carbonyl]amino acetate is prepared from N-(benzyloxycarbonyl)hydroxylamine and acetyl chloride according to Scheme 1. (1.24 g, 33%), $^1$H NMR (500 MHz, CHLOROFORM-d) δ ppm 8.18 (1H, br. s.), 7.32-7.45 (5H, m), 5.22 (2H, s), 2.22 (3H, s).

Benzyl (acetyloxy){[2-(methylsulfonyl)phenyl]sulfonyl}carbamate (50) is prepared from 2-methylsulfonylbenzenesulfonyl chloride, sodium hydride and [(benzyloxy)carbonyl]amino acetate according to Scheme 2. (0.33 g, 28%), $^1$H NMR (500 MHz, CHLOROFORM-d) δ ppm 8.21-8.47 (2H, m), 7.79-7.88 (1H, m), 7.65-7.74 (1H, m), 7.30-7.41 (3H, m), 7.16-7.24 (2H, m), 5.18 (2H, br. s.), 3.31 (3H, s), 2.29 (3H, s).

Preparation of benzyl {[2-(methylsulfonyl)phenyl]sulfonyl}(propanoyloxy)carbamate (51)

[(Benzyloxy)carbonyl]amino propanoate is prepared from N-(benzyloxycarbonyl) hydroxylamine and propionyl chloride according to Scheme 1. (3.6 g, 89%), $^1$H NMR (500 MHz, CHLOROFORM-d) δ ppm 8.18 (1H, s), 7.32-7.43 (5H, m), 5.22 (2H, s), 2.50 (2H, q, 7.6 Hz), 1.22 (3H, t, 7.6 Hz).

Benzyl {[2-(methylsulfonyl)phenyl]sulfonyl}(propanoyloxy)carbamate (51) is prepared from 2-methylsulfonylbenzenesulfonyl chloride, sodium hydride and [(benzyloxy)carbonyl]-amino propanoate according to Scheme 2. (0.56 g, 50%), $^1$H NMR (500 MHz, CHLOROFORM-d) δ ppm 8.39 (1H, d, 7.9 Hz), 8.35 (1H, d, 7.9 Hz), 7.80-7.86 (1H, m), 7.68-7.73 (1H, m), 7.30-7.39 (3H, m), 7.18-7.23 (2H, m), 5.17 (2H, br. s.), 3.30 (3H, s), 2.58 (2H, br. s.), 1.23 (3H, t, 7.5 Hz).

Preparation of N-[(tert-butoxy)carbonyl][2-chloro-5-(dimethylcarbamoyl)benzene]sulfonamido 2,2-dimethylpropanoate (53)

4-Chloro-3-(chlorosulfonyl)benzoic acid

The following method for the chorosulfonylation of benzoic acids is described in *Bioorg. Med. Chem.* 2002, 639-656:

To a flask containing chlorosulfonic acid (17 ml, 250 mmol) cooled to 0° C. is added 4-chlorobenzoic acid (5.2 g, 33.3 mmol) portionwise. The reaction mixture is heated to 130° C. for 24 hours or until complete consumption of the starting material. The reaction mixture is cooled to ambient temperature before careful addition to ice. The resulting solid is filtered and washed with cold water (50 ml). The wet product is dissolved in diethyl ether (100 ml), dried over sodium sulfate, filtered and concentrated in vacuo to yield the title compound without need for additional purification. (6.1 g, 71%), $^1$H NMR (500 MHz, MeOD) δ ppm 8.57 (1H, s), 7.42-7.76 (2H, m).

4-Chloro-3-(chlorosulfonyl)benzoyl chloride

4-Chloro-3-(chlorosulfonyl)benzoic acid (6.1 g, 24 mmol) is suspended in toluene (50 ml). Thionyl chloride (3.5 ml, 47 mmol) is added dropwise, and the mixture is heated to reflux for 14 hours under nitrogen until complete consumption of the carboxylic acid is observed by LCMS. The reaction mixture is concentrated to dryness to afford the expected acid chloride which is used for next step without further purification.

2-Chloro-5-(dimethylcarbamoyl)benzene-1-sulfonyl chloride

The following method is described in *Journal of Pharmacy and Pharmacology* 1963, 202-211:
Dimethylamine hydrochloride (0.5 g, 6.2 mmol) is added to a stirred solution of 4-chloro-3-(chlorosulfonyl)benzoyl chloride (1.6 g, 5.88 mmol) in chlorobenzene (10 ml). The reaction mixture is heated to reflux for 2 hours, or until complete consumption of the starting material is observed by LCMS. The reaction mixture is concentrated to dryness and the residue is taken up in diethyl ether (20 ml). The precipitate is filtered and washed with diethyl ether (2×10 ml) to afford the title compound. (1.1 g, 64%), $^1$H NMR (500 MHz, DMSO-d6) δ ppm 7.86 (1H, d, 2.0 Hz), 7.43 (1H, d, 8.1 Hz), 7.34 (1H, dd, 8.1, 2.2 Hz), 2.97 (3H, br. s), 2.90 (3H, br. s).

N-[(tert-Butoxy)carbonyl][2-chloro-5-(dimethylcarbamoyl)benzene]sulfonamido 2,2-dimethylpropanoate (53) is synthesised from 2-chloro-5-(dimethylcarbamoyl)benzene-1-sulfonyl chloride, sodium hydride and [(tert-butoxy)carbonyl]amino 2,2-dimethylpropanoate according to Scheme 2. (0.5 g, 40%), $^1$H NMR (250 MHz, DMSO-d6) δ ppm 8.04 (1H, s), 7.46-7.79 (2H, m), 2.92 (3H, br. s.), 2.83 (3H, br. s.), 1.18 (9H, s) 1.12 (9H, s).

Preparation of N-[(tert-butoxy)carbonyl](2-methanesulfonylbenzene)sulfonamido 2-(acetyloxy)benzoate (54)

[(tert-Butoxy)carbonyl]amino 2-(acetyloxy)benzoate is prepared from acetylsalicyloyl chloride and N-tert-butoxycarbonyl hydroxylamine according to Scheme 1 described by Carpino et al. *J. Am. Chem. Soc.* 1959, 955-957. $^1$H NMR (250 MHz, DMSO-d6) δ ppm 10.89 (1H, br. s.), 7.97 (1H, dd, 7.8, 1.7 Hz), 7.75 (1H, td, 7.8, 1.8 Hz), 7.46 (1H, td, 7.6, 1.1 Hz), 7.31 (1H, dd, 8.1, 0.9 Hz), 2.27 (3H, s), 1.42 (9H, s).

N-[(tert-Butoxy)carbonyl](2-methanesulfonylbenzene)sulfonamido 2-(acetyloxy)benzoate (54) is synthesised from 2-methylsulfonylbenzenesulfonyl chloride, sodium hydride and [(tert-butoxy)carbonyl]amino 2-(acetyloxy)benzoate according to Scheme 2. (5.5 g, 89%), $^1$H NMR (250 MHz, DMSO-d6) δ ppm 8.34-8.43 (1H, m), 8.07-8.21 (3H, m), 7.94-8.05 (1H, m), 7.77 (1H, td, 7.9, 1.8 Hz), 7.56-7.66 (1H, m), 7.07-7.16 (1H, m), 3.45 (3H, s), 2.48 (3H, s.), 1.43 (9H, s).

Preparation of N-[(tert-butoxy)carbonyl]-1-benzofuran-2-sulfonamido 2,2-dimethylpropanoate (55)

N-[(tert-Butoxy)carbonyl]1-benzofuran-2-sulfonamido 2,2-dimethylpropanoate (55) is prepared from [(tert-butoxy)carbonyl]amino 2,2-dimethylpropanoate, sodium hydride and 1-benzofuran-2-sulfonyl chloride according to Scheme 2. (4.0 g, 87%), $^1$H NMR (250 MHz, DMSO-d6) δ ppm 8.06 (1H, d, 0.8 Hz), 7.92 (1H, d, 7.3 Hz), 7.81 (1H, dd, 8.5, 0.8 Hz), 7.64 (1H, ddd, 8.5, 7.2, 1.4 Hz), 7.42-7.53 (1H, m), 1.37 (9H, s), 1.28 (9H, s).

Preparation of N-[(tert-butoxy)carbonyl]-1-benzofuran-2-sulfonamido acetate (56)

N-[(tert-Butoxy)carbonyl]-1-benzofuran-2-sulfonamido acetate (56) is prepared from [(tert-butoxy)carbonyl]amino acetate, sodium hydride and 1-benzofuran-2-sulfonyl chloride according to Scheme 2. (3.1 g, 75%), $^1$H NMR (250 MHz, DMF) δ ppm 8.07 (1H, d, 0.9 Hz), 7.91 (1H, d, 7.3 Hz), 7.82 (1H, dd, 8.5, 0.8 Hz), 7.64 (1H, td, 7.8, 1.4 Hz), 7.41-7.52 (1H, m), 2.32 (3H, s), 1.37 (9H, s).

Preparation of N-[(tert-butoxy)carbonyl](2-bromobenzene)sulfonamido benzoate (57)

N-[(tert-Butoxy)carbonyl](2-bromobenzene)sulfonamido benzoate (57) is synthesised from 2-bromobenzenesulfonyl chloride, sodium hydride and [(tert-butoxy)carbonyl]amino benzoate according to Scheme 2. (4.8 g, 87%), $^1$H NMR (500 MHz, CHLOROFORM-d) δ ppm 8.34 (1H, dd, 7.6, 2.1 Hz), 8.12-8.22 (2H, m), 7.82 (1H, dd, 7.5, 1.7 Hz), 7.63-7.70 (1H, m), 7.48-7.57 (4H, m), 1.39 (9H, s).

Preparation of N-[(tert-butoxy)carbonyl]3-bromothiophene-2-sulfonamido 2,2-dimethylpropanoate (58)

N-[(tert-Butoxy)carbonyl]3-bromothiophene-2-sulfonamido 2,2-dimethylpropanoate (58) is synthesised from 3-bromothiophene-2-sulfonyl chloride (synthesised according to the method detailed in *Bioorganic and Medicinal Chemistry Letters* 1996, 6, 2651-2656), sodium hydride and [(tert-Butoxy)carbonyl]amino 2,2-dimethylpropanoate according to Scheme 2. (0.2 g, 12%), $^1$H NMR (500 MHz, DMSO-d6) δ ppm 8.25 (1H, d, 5.2 Hz), 7.44 (1H, d, 5.2 Hz), 1.39 (9H, s), 1.29 (9H, s).

Preparation of N-[(tert-butoxy)carbonyl]3-chlorothiophene-2-sulfonamido 2,2-dimethylpropanoate (59)

3-Chlorothiophene-2-sulfonyl chloride is synthesised according to the method detailed in *Bioorganic and Medicinal Chemistry Letters* 1996, 6, 2651-2656:
To a stirred solution of 3-chlorothiophene (10 g, 84 mmol) in dichloromethane (25 ml) cooled to 0° C. is added chlorosulfonic acid (16 ml, 252 mmol) dropwise. The reaction mixture is then stirred for 2 hours at 0° C. is and then carefully poured onto ice and extracted into dichloromethane (2×250 ml). The organics are combined and dried over sodium sulfate, filtered and concentrated in vacuo to afford the title compound as a mixture with the other isomer. Both isomers are separated and the title compound isolated by silica column chromatography eluting with hexane: ethyl acetate. (3.7 g, 20%), $^1$H NMR (500 MHz, CHLOROFORM-d) δ ppm 7.75 (1H, d, 5.3 Hz), 7.15 (1H, d, 5.3 Hz).

N-[(tert-Butoxy)carbonyl]3-chlorothiophene-2-sulfonamido 2,2-dimethylpropanoate (59) is synthesised from 3-chlorothiophene-2-sulfonyl chloride, sodium hydride and [(tert-butoxy)carbonyl]amino 2,2-dimethylpropanoate according to Scheme 2. (1.72 g, 94%), $^1$H NMR (500 MHz, DMSO-d6) δ ppm 8.29 (1H, d, 5.3 Hz), 7.40 (1H, d, 5.2 Hz), 1.39 (9H, s), 1.28 (9H, s).

Preparation of N-[(tert-butoxy)carbonyl](2-bromobenzene)sulfonamido 2-methylpropanoate (60)

N-[(tert-Butoxy)carbonyl](2-bromobenzene)sulfonamido 2-methylpropanoate (60) is prepared from 2-bromobenzene sulfonyl chloride, sodium hydride and [(tert-butoxy)carbonyl]amino 2-methylpropanoate according to Scheme 2. (1.96 g, 59%), $^1$H NMR (250 MHz, CHLOROFORM-d) δ ppm 8.23-8.37 (1H, m), 7.72-7.88 (1H, m), 7.42-7.59 (2H, m), 2.67-3.02 (1H, m), 1.37 (9H, s), 1.34 (3H, s), 1.32 (3H, s).

Preparation of N-[(tert-butoxy)carbonyl](2-bromobenzene)sulfonamido 2,2-dimethylpropanoate (61)

N-[(tert-Butoxy)carbonyl](2-bromobenzene)sulfonamido 2,2-dimethylpropanoate (61) is prepared from 2-bromobenzene sulfonyl chloride, sodium hydride and [(tert-butoxy)carbonyl]amino 2,2-dimethylpropanoate according to Scheme 2. (2.57 g, 75%), $^1$H NMR (250 MHz, CHLOROFORM-d) δ ppm 8.13-8.52 (1H, m), 7.71-7.96 (1H, m), 7.38-7.61 (2H, m), 2.64-3.03 (1H, m), 1.37 (9H, s), 1.33 (6H, d, 7.0 Hz).

Preparation of N-[(tert-butoxy)carbonyl](2-chlorobenzene)sulfonamido 2,2-dimethylpropanoate (62)

N-[(tert-Butoxy)carbonyl](2-chlorobenzene)sulfonamido 2,2-dimethylpropanoate (62) is prepared from 2-chlorobenzenesulfonyl chloride, sodium hydride and [(tert-butoxy)carbonyl]-amino 2,2-dimethylpropanoate according to Scheme 2. (4.1 g, 81%), $^1$H NMR (250 MHz, CHLOROFORM-d) δ ppm 7.63-7.70 (1H, m), 7.55-7.6 (2H, m), 7.40-7.50 (1H, m), 1.38 (9H, s), 1.37 (9H, s).

Preparation of N-[(tert-butoxy)carbonyl][2-chloro-5-(dimethyl carbamoyl)benzene]sulfonamido-acetate (63)

N-[(tert-Butoxy)carbonyl][2-chloro-5 (dimethylcarbamoyl)benzene]sulfonamidoacetate (63) is prepared from 2-chloro-5-(dimethylcarbamoyl)benzene-1-sulfonyl chloride, sodium hydride and [(tert-butoxy)carbonyl]amino acetate according to Scheme 2. (1.2 g, 95%), $^1$H NMR (500 MHz, DMSO-d$_6$) δ ppm 8.11 (1H, s), 7.87 (2H, s), 3.00 (3H, s), 2.91 (3H, s), 1.40 (3H, s), 1.29 (9H, s).

Preparation of N-[(tert-butoxy)carbonyl](2-chlorobenzene)sulfonamido 2-methylpropanoate (64)

N-[(tert-Butoxy)carbonyl](2-chlorobenzene)sulfonamido 2-methylpropanoate (64) is prepared from 2-chlorobenzene sulfonyl chloride, sodium hydride and [(tert-butoxy)carbonyl]amino 2-methylpropanoate according to Scheme 2. (3.4 g, 91%), $^1$H NMR (250 MHz, CHLOROFORM-d) δ ppm 8.16-8.29 (1H, m), 7.52-7.63 (2H, m), 7.39-7.51 (1H, m), 2.86 (1H, quin, 7.0 Hz), 1.38 (9H, s), 1.33 (6H, d, 7.0 Hz).

Preparation of N-[(tert-butoxy)carbonyl](2-bromobenzene)sulfonamido 2-phenylacetate (65)

[(tert-Butoxy)carbonyl]amino 2-phenylacetate is prepared from phenylacetyl chloride and N-tert-butoxycarbonyl hydroxylamine according to Scheme 1 using literature conditions. (8.8 g, 100%), $^1$H NMR (500 MHz, DMSO-d6) δ ppm 10.66 (1H, br. s.), 7.24-7.38 (5H, m), 3.80 (2H, s), 1.38 (9H, s).

N-[(tert-Butoxy)carbonyl](2-bromobenzene)sulfonamido 2-phenylacetate (65) is prepared from 2-bromobenzene sulfonyl chloride, sodium hydride and [(tert-butoxy)carbonyl]amino 2-phenylacetate according to Scheme 2. $^1$H NMR (500 MHz, DMSO-d6) δ ppm 8.16-8.23 (1H, m), 7.95-8.00 (1H, m), 7.66-7.75 (2H, m), 7.26-7.41 (5H, m), 4.04 (2H, s), 1.24 (9H, s).

Preparation of N-[(tert-butoxy)carbonyl](2-bromobenzene)sulfonamido 2-methyl-2-phenylpropanoate (66)

[(tert-butoxy)carbonyl]amino 2-methyl-2-phenylpropanoate

A solution of α,α dimethyl phenylacetic acid (2 g, 12.18 mmol) in thionyl chloride (20 ml) is heated to reflux for 1 hour after which time all of the starting acid has been consumed. The reaction mixture is concentrated in vacuo and the resulting acid chloride is used directly for the synthesis of [(tert-butoxy)carbonyl]amino 2-methyl-2-phenylpropanoate, which is prepared from the described acid chloride and N-tert-butoxycarbonyl hydroxylamine according to Scheme 1. (2.76 g, 81%), $^1$H NMR (500 MHz, CHLOROFORM-d) δ ppm 7.64 (1H, s), 7.29 (4H, dt, 15.6, 7.8 Hz), 7.12-7.23 (1H, m), 1.60 (6H, s), 1.38 (9H, s).

N-[(tert-Butoxy)carbonyl](2-bromobenzene)sulfonamido 2-methyl-2-phenyl propanoate (66) is prepared from 2-bromobenzene sulfonyl chloride, sodium hydride and [(tert-butoxy)carbonyl]amino 2-methyl-2-phenylpropanoate according to Scheme 2. (1.46 g, 82%), $^1$H NMR (500 MHz, CHLOROFORM-d) δ ppm 8.12-8.21 (1H, m), 7.65-7.78 (1H, m), 7.41-7.49 (4H, m), 7.37 (2H, t, 7.7 Hz), 7.26-7.31 (1H, m), 1.75 (6H, s), 1.36 (9H, s).

Preparation of N-[(tert-butoxy)carbonyl](2-bromobenzene)sulfonamido 1-phenylcyclopentane-1-carboxylate (67)

[(tert-Butoxy)carbonyl]amino 1-phenylcyclopentane-1-carboxylate

A solution of 1-phenyl cyclopentane carboxylic acid (2 g, 10.5 mmol) in thionyl chloride (20 ml) is heated to reflux for 1 hour after which time all of the starting acid has been consumed.

The reaction mixture is concentrated in vacuo and the resulting acid chloride used directly for the synthesis [(tert-butoxy)carbonyl]amino 1-phenylcyclopentane-1-carboxylate, which is prepared from the described acid chloride and N-tert-butoxycarbonyl hydroxylamine according to Scheme 1. (2.4 g, 75%), $^1$H NMR (250 MHz, CHLOROFORM-d) δ ppm 7.62 (1H, s), 7.18-7.49 (5H, m), 2.63-2.86 (2H, m), 1.93-2.11 (2H, m), 1.71-1.90 (4H, m), 1.45 (9H, s).

N-[(tert-Butoxy)carbonyl](2-bromobenzene)sulfonamido 1-phenylcyclopentane-1-carboxylate (67) is synthesised from 2-bromobenzene sulfonyl chloride, sodium hydride and [(tert-butoxy)carbonyl]amino 1-phenylcyclopentane-1-carboxylate according to Scheme 2. (1.41 g, 82%), $^1$H NMR (500 MHz, CHLOROFORM-d) δ ppm 8.09-8.18 (1H, m), 7.62-7.75 (1H, m), 7.38-7.49 (4H, m), 7.34 (2H, t, 7.6 Hz), 7.23-7.30 (1H, m), 2.68-2.94 (2H, m), 1.76-2.17 (6H, m), 1.29 (9H, s).

Preparation of 2-N-[(tert-butoxy)carbonyl](2-bromobenzene)sulfonamido-1-tert-butyl pyrrolidine-1,2-dicarboxylate (68)

2-[(tert-Butoxy)carbonyl]amino-1-tert-butyl pyrrolidine-1,2-dicarboxylate is synthesised using the method detailed in *Tetrahedron* 1994, 5049-5066. (1.78 g, 81%), $^1$H NMR (250 MHz, CHLOROFORM-d) δ ppm 7.56-8.33 (1H, s), 4.43 (1H, ddd, 15.6, 8.3, 4.3 Hz), 3.20-3.85 (2H, m), 2.11-2.39 (2H, m), 1.81-2.10 (2H, m), 1.56-1.65 (9H, s), 1.49 (9H, s).

2-N-[(tert-Butoxy)carbonyl](2-bromobenzene)sulfonamido-1-tert-butyl pyrrolidine-1,2-dicarboxylate (68) is synthesised from 2-bromobenzene sulfonyl chloride, sodium hydride and 2-[(tert-butoxy)carbonyl]amino 1-tert-butyl pyrrolidine-1,2-dicarboxylate according to Scheme 2. (0.97 g, 73%), $^1$H NMR (250 MHz, CHLOROFORM-d) δ ppm 8.21-8.32 (1H, m), 7.72-7.84 (1H, m), 7.41-7.58 (2H, m), 4.55-4.70 (1H, m), 3.53-3.68 (1H, m), 3.31-3.53 (1H, m), 2.22-2.42 (2H, m), 1.85-2.14 (2H, m), 1.44-1.50 (9H, s), 1.38 (9H, s).

Preparation of N-[(tert-butoxy)carbonyl](2-bromobenzene)sulfonamido 2-[4-(dimethylamino)phenyl]acetate (69)

[(tert-Butoxy)carbonyl]amino 2-[4-(dimethylamino)phenyl]acetate

To a solution of 4-dimethylamino phenyl acetic acid (2.0 g, 11.6 mmol) in DCM (20 ml) is added EDCI.HCl (3.2 g, 16.74 mmol) and triethylamine (4.7 ml, 33.48 mmol). The reaction is stirred for 30 minutes before addition of N-tert-butoxycarbonyl hydroxylamine (2.2 g, 16.74 mmol). The reaction is stirred for 18 hours then quenched with water (10 ml). The organics are separated, washed twice with water (2×5 ml), dried over sodium sulfate and concentrated in vacuo. Purification of the title compound is achieved by silica gel column chromatography eluting with heptane: ethyl acetate (4:1, v:v). (2.08 g, 63%), $^1$H NMR (250 MHz, CHLOROFORM-d) δ ppm 7.89 (1H, s), 7.11-7.23 (2H, m), 6.63-6.76 (2H, m), 2.94 (6H, s), 1.47 (9H, s).

N-[(tert-Butoxy)carbonyl](2-bromobenzene)sulfonamido 2-[4-(dimethylamino)phenyl]acetate (69) is synthesised from 2-bromobenzene sulfonyl chloride, sodium hydride and [(tert-butoxy)carbonyl]amino 2-[4-(dimethylamino)phenyl]acetate according to Scheme 2. (0.39 g, 23%), $^1$H NMR (500 MHz, CHLOROFORM-d) δ ppm 8.16-8.33 (1H, m), 7.74-7.82 (1H, m), 7.43-7.54 (2H, m), 7.21 (2H, d, 8.5 Hz), 6.71 (2H, d, 8.1 Hz), 3.80 (2H, s), 2.94 (6H, s), 1.34 (9H, s).

Preparation of N-[(tert-butoxy)carbonyl](2-bromobenzene)sulfonamido 1-acetylpyrrolidine-2-carboxylate (70)

[(tert-Butoxy)carbonyl]amino-1-acetyl-L-pyrrolidine-2-carboxylate is synthesised using the method detailed in *Tetrahedron* 1994, 5049-5066. (1.05 g, 36%), $^1$H NMR (250 MHz, CHLOROFORM-d) δ ppm 8.15 (1H, br. s.), 4.49-4.73 (1H, m), 3.60-3.74 (1H, m), 3.45-3.59 (1H, m), 2.13-2.41 (2H, m), 2.10 (3H, s), 1.91-2.08 (2H, m), 1.41-1.51 (9H, m).

N-[(tert-Butoxy)carbonyl](2-bromobenzene)sulfonamido 1-acetyl-L-pyrrolidine-2-carboxylate (70) is synthesised from 2-bromobenzene sulfonyl chloride, sodium hydride and [(tert-butoxy)carbonyl]amino-1-acetyl-L-pyrrolidine-2-carboxylate according to Scheme 2. (0.66 g, 35%), $^1$H NMR (500 MHz, CHLOROFORM-d) δ ppm 8.21-8.34 (1H, m), 7.75-7.83 (1H, m), 7.44-7.56 (2H, m), 4.51-4.65 (1H, m), 3.63-3.77 (1H, m), 3.45-3.62 (1H, m), 2.31-2.55 (2H, m), 2.15-2.31 (2H, m), 2.11 (3H, s), 1.49 (9H, s).

Preparation of N-[(tert-butoxy)carbonyl](2-bromobenzene)sulfonamido (2S)-2-phenylpropanoate (71)

[(tert-Butoxy)carbonyl]amino (2S)-2-phenylpropanoate is synthesised using the method detailed in *Tetrahedron* 1994, 5049-5066. (2.57 g, 73%), $^1$H NMR (500 MHz, CHLOROFORM-d) δ ppm 7.77 (1H, s), 7.33-7.37 (4H, m), 7.28-7.32 (1H, m), 3.90 (1H, q, 7.2 Hz), 1.60 (3H, d, 7.3 Hz), 1.45 (9H, s).

N-[(tert-Butoxy)carbonyl](2-bromobenzene)sulfonamido (2S)-2-phenylpropanoate (71) is synthesised from 2-bromobenzene sulfonyl chloride, sodium hydride and [(tert-butoxy)carbonyl]amino (2S)-2-phenylpropanoate according to Scheme 2. (0.36 g, 20%), $^1$H NMR (500 MHz, CHLOROFORM-d) δ ppm 8.10 (1H, d, 8.2 Hz), 7.81-7.91 (1H, m), 7.79 (1H, d, 8.2 Hz), 7.33-7.41 (5H, m), 6.95-7.05 (1H, m), 4.13 (1H, q, 7.1 Hz), 1.67 (3H, d, 7.2 Hz), 1.59 (9H, s).

Preparation of N-[(tert-butoxy)carbonyl](2-bromobenzene)sulfonamido (2R)-2-phenylpropanoate (72)

[(tert-Butoxy)carbonyl]amino (2R)-2-phenylpropanoate is synthesised using the method detailed in *Tetrahedron* 1994, 5049-5066. (0.92 g, 69%), $^1$H NMR (250 MHz, CHLOROFORM-d) δ ppm 7.78 (1H, s), 7.15-7.40 (5H, m), 3.90 (1H, q, 7.1 Hz), 1.60 (3H, d, 7.2 Hz), 1.45 (9H, s).

N-[(tert-Butoxy)carbonyl](2-bromobenzene)sulfonamido (2R)-2-phenylpropanoate (72) is synthesised from 2-bromobenzene sulfonyl chloride, sodium hydride and [(tert-butoxy)carbonyl]amino (2R)-2-phenylpropanoate according to Scheme 2. (0.66 g, 35%), $^1$H NMR (500 MHz, CHLOROFORM-d) δ ppm 8.02-8.36 (1H, m), 7.67-7.85 (1H, m), 7.28-7.53 (7H, m), 3.89-4.06 (1H, m), 1.66 (3H, d, 7.2 Hz), 1.37 (9H, s).

Preparation of N-[(tert-butoxy)carbonyl]-5-chlorothiophene-2-sulfonamido 2-methylpropanoate (73)

N-[(tert-Butoxy)carbonyl]-5-chlorothiophene-2-sulfonamido 2-methylpropanoate (73) is synthesised from 5-chlorothiophene sulfonyl chloride, sodium hydride and [(tert-butoxy)carbonyl]amino 2-methylpropanoate according to Scheme 2. (1.7 g, 100%), $^1$H NMR (500 MHz, CHLOROFORM-d) δ ppm 7.65 (1H, d, 4.1 Hz), 6.99 (1H, d, 4.1 Hz), 2.81 (1H, sept, 7.0 Hz), 1.49 (9H, s), 1.31 (6H, d, 7.0 Hz).

Preparation of N-[(tert-butoxy)carbonyl]-5-chlorothiophene-2-sulfonamido 2,2-dimethylpropanoate (74)

N-[(tert-Butoxy)carbonyl]-5-chlorothiophene-2-sulfonamido 2,2-dimethylpropanoate (74) is synthesised from 5-chlorothiophene sulfonyl chloride, sodium hydride and [(tert-butoxy)carbonyl]amino 2,2-dimethylpropanoate according to Scheme 2. (1.89 g, 100%), $^1$H NMR (500 MHz, CHLOROFORM-d) δ ppm 7.65 (1H, d, 4.1 Hz), 6.99 (1H, d, 4.1 Hz), 1.48 (9H, s), 1.35 (9H, s).

Preparation of N-[(tert-butoxy)carbonyl](3-methanesulfonylbenzene)sulfonamido 2,2-dimethylpropanoate (75)

N-[(tert-Butoxy)carbonyl](3-methanesulfonylbenzene)sulfonamido 2,2-dimethylpropanoate (75) is synthesised from 2-methanesulfonylbenzene sulfonyl chloride, sodium hydride and [(tert-butoxy)carbonyl]amino 2,2-dimethylpropanoate according to Scheme 2. (0.63 g, 37%), $^1$H NMR (500 MHz, CHLOROFORM-d) δ ppm 8.60 (1H, s), 8.35 (1H, d, 7.9 Hz), 8.26 (1H, d, 7.8 Hz), 7.81 (1H, t, 7.9 Hz), 1.43 (9H, s), 1.37 (9H, s).

Preparation of N-[(tert-butoxy)carbonyl](3-methanesulfonylbenzene)sulfonamido 2-methylpropanoate (76)

N-[(tert-Butoxy)carbonyl](3-methanesulfonylbenzene)sulfonamido 2-methyl propanoate (76) is synthesised from 2-methanesulfonylbenzene sulfonyl chloride, sodium hydride and [(tert-butoxy)carbonyl]amino 2-methylpropanoate according to Scheme 2. (1.3 g, 78%), $^1$H NMR (500 MHz, CHLOROFORM-d) δ ppm 8.60 (1H, t, 1.7 Hz), 8.35 (1H, d, 7.9 Hz), 8.26 (1H, d, 7.8 Hz), 7.82 (1H, t, 7.9 Hz), 2.78-2.88 (1H, m), 1.43 (9H, s), 1.33 (6H, d, 7.0 Hz).

Preparation of N-[(tert-butoxy)carbonyl]pyridine-3-sulfonamido 2,2-dimethylpropanoate (77)

N-[(tert-Butoxy)carbonyl]pyridine-3-sulfonamido 2,2-dimethylpropanoate (77) is synthesised from 3-pyridine sulfonyl chloride, sodium hydride and [(tert-butoxy)carbonyl]amino 2,2-dimethylpropanoate according to Scheme 2. (0.99 g, 58%), $^1$H NMR (500 MHz, CHLOROFORM-d) δ ppm 9.16-9.26 (1H, m), 8.89 (1H, d, 4.4 Hz), 8.36 (1H, d, 8.2 Hz), 7.54 (1H, dd, 8.2, 4.9 Hz), 1.42 (9H, s), 1.37 (9H, s)

Preparation of N-[(tert-butoxy)carbonyl]pyridine-3-sulfonamido 2-methylpropanoate (78)

N-[(tert-Butoxy)carbonyl]pyridine-3-sulfonamido 2-methylpropanoate (78) is synthesised from 3-pyridine sulfonyl chloride, sodium hydride and [(tert-butoxy)carbonyl]amino 2-methylpropanoate according to Scheme 2. (0.6 g, 37%), $^1$H NMR (500 MHz, CHLOROFORM-d) δ ppm 9.21 (1H, d, 1.6 Hz), 8.89 (1H, dd, 4.7, 1.3 Hz), 8.34 (1H, dd, 7.4, 1.4 Hz), 7.53 (1H, dd, 8.2, 4.9 Hz), 2.84 (1H, sept, 7.0 Hz), 1.42 (9H, s), 1.32 (6H, d, 6.9 Hz).

Tert-butyl(acetyloxy) [(3-bromothiophen-2-yl)sulfonyl]carbamate (103) is prepared from 3-bromothiophene-2-sulfonyl chloride, sodium hydride and [(tert-butoxy)carbonyl]aminoacetate according to Scheme 2. δH (250 MHz, CHLOROFORM-d) 7.68 (1H, d, 5.3 Hz), 7.15 (1H, d, 5.2 Hz), 2.30 (3H, s), 1.48 (9H, s).

N-[(tert-Butoxy)carbonyl]1-benzofuran-2-sulfonamido 2,2-dimethylpropanoate (104) is prepared from [(tert-butoxy)carbonyl]amino 2,2-dimethylpropanoate, sodium hydride and 1-benzofuran-2-sulfonyl chloride according to Scheme 2. δH (250 MHz, DMSO-d6) 8.06 (1H, d, 0.8 Hz), 7.92 (1H, d, 7.3 Hz), 7.81 (1H, dd, 8.5, 0.8 Hz), 7.64 (1H, ddd, 8.5, 7.2, 1.4 Hz), 7.42-7.53 (1H, m), 1.37 (9H, s), 1.28 (9H, s).

N-[(tert-Butoxy)carbonyl]1-benzofuran-2-sulfonamido acetate (105) is prepared from [(tert-butoxy)carbonyl]amino acetate, sodium hydride and 1-benzofuran-2-sulfonyl chloride according to Scheme 2. δH (250 MHz, DMF) 8.07 (1H, d, 0.9 Hz), 7.91 (1H, d, 7.3 Hz), 7.82 (1H, dd, 8.5, 0.8 Hz), 7.64 (1H, td, 7.8, 1.4 Hz), 7.41-7.52 (1H, m), 2.32 (3H, s), 1.37 (9H, s).

N-[(tert-Butoxy)carbonyl]3-bromothiophene-2-sulfonamido 2,2-dimethylpropanoate (106) is synthesised from 3-bromothiophene-2-sulfonyl chloride (synthesised according to the method detailed in Bioorganic and Medicinal Chemistry Letters 1996, 6, 2651-2656), sodium hydride and [(tert-Butoxy)carbonyl]amino 2,2-dimethylpropanoate according to Scheme 2. δH (500 MHz, DMSO-d6) 8.25 (1H, d, 5.2 Hz), 7.44 (1H, d, 5.2 Hz), 1.39 (9H, s), 1.29 (9H, s).

N-[(tert-Butoxy)carbonyl]3-chlorothiophene-2-sulfonamido 2,2-dimethylpropanoate (107) is synthesised from 3-chlorothiophene-2-sulfonyl chloride, sodium hydride and [(tert-butoxy)carbonyl]amino 2,2-dimethylpropanoate according to Scheme 2. δH (500 MHz, DMSO-d6) 8.29 (1H, d, 5.3 Hz), 7.40 (1H, d, 5.2 Hz), 1.39 (9H, s), 1.28 (9H, s).

3-Chlorothiophene-2-sulfonyl chloride is synthesised according to the method detailed in Bioorganic and Medicinal Chemistry Letters 1996, 6, 2651-2656. To a stirred solution of 3-chlorothiophene (10 g, 84 mmol) in dichloromethane (25 ml) cooled to 0° C. is added chlorosulfonic acid (16 ml, 252 mmol) dropwise. After 2 hours at 0° C., the reaction mixture is carefully poured onto ice and extracted into dichloromethane (2×250 ml). The organics are combined and dried over sodium sulfate, filtered and concentrated in vacuo to afford the title compound as a mixture with the other isomer. Both isomers are separated and the title compound isolated by silica column chromatography eluting with hexane:ethyl acetate (3.7 g, 20%). δH (500 MHz, CHLOROFORM-d) 7.75 (1H, d, 5.3 Hz), 7.15 (1H, d, 5.3 Hz).

N-[(tert-Butoxy)carbonyl]5-chlorothiophene-2-sulfonamido 2-methylpropanoate (108) is synthesised from 5-chlorothiophene sulfonyl chloride, sodium hydride and [(tert-butoxy)carbonyl]amino 2-methylpropanoate according to Scheme 2. δH (500 MHz, CHLOROFORM-d) 7.65 (1H, d, 4.1 Hz), 6.99 (1H, d, 4.1 Hz), 2.81 (1H, sept, 7.0 Hz), 1.49 (9H, s), 1.31 (6H, d, 7.0 Hz).

N-[(tert-Butoxy)carbonyl]5-chlorothiophene-2-sulfonamido 2,2-dimethylpropanoate (109) is synthesised from 5-chlorothiophene sulfonyl chloride, sodium hydride and [(tert-butoxy)carbonyl]amino 2,2-dimethylpropanoate according to Scheme 2. δH (500 MHz, CHLOROFORM-d) 7.65 (1H, d, 4.1 Hz), 6.99 (1H, d, 4.1 Hz), 1.48 (9H, s), 1.35 (9H, s).

N-[(tert-Butoxy)carbonyl]pyridine-3-sulfonamido 2,2-dimethylpropanoate (110) is synthesised from 3-pyridine sulfonyl chloride, sodium hydride and [(tert-butoxy)carbonyl]amino 2-methylpropanoate according to Scheme 2. δH (500 MHz, CHLOROFORM-d) 9.16-9.26 (1H, m), 8.89 (1H, d, 4.4 Hz), 8.36 (1H, d, 8.2 Hz), 7.54 (1H, dd, 8.2, 4.9 Hz), 1.42 (9H, s), 1.37 (9H, s)

N-[(tert-Butoxy)carbonyl]pyridine-3-sulfonamido 2-methylpropanoate (111) is synthesised from 3-pyridine sulfonyl chloride, sodium hydride and [(tert-butoxy)carbonyl]amino 2-methylpropanoate according to Scheme 2. δH (500 MHz, CHLOROFORM-d) 9.21 (1H, d, 1.6 Hz), 8.89 (1H, dd, 4.7, 1.3 Hz), 8.34 (1H, dd, 7.4, 1.4 Hz), 7.53 (1H, dd, 8.2, 4.9 Hz), 2.84 (1H, sept, 7.0 Hz), 1.42 (9H, s), 1.32 (6H, d, 6.9 Hz).

Example 5

Synthesis of Compounds 48 and 49

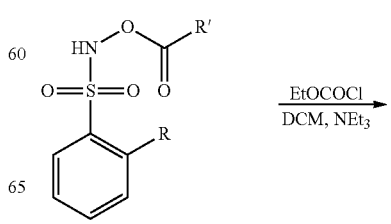

Scheme 3

-continued

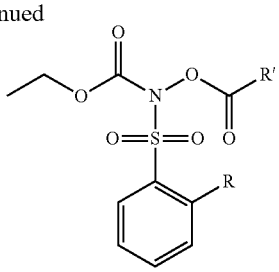

Preparation of ethyl (acetyloxy){[2-(methylsulfonyl)phenyl]sulfonyl}-carbamate (48)

N-(Acetyloxy)-2-(methylsulfonyl)benzenesulfonamide

To a solution of tert-butyl(acetyloxy){[2-(methylsulfonyl)phenyl]sulfonyl}carbamate (0.5 g, 1.27 mmol) in DCM (10 ml) is added trifluoroacetic acid (4 ml) and the resulting solution stirred at room temperature until complete removal of the BOC group is identified by LC-MS (2 hours). The crude reaction mixture is concentrated in vacuo and the resulting solid purified by trituration with diethyl ether. (0.24 g, 64%), $^1$H NMR (400 MHz, DMSO-d6) δ ppm 10.63 (1H, br. s.), 8.28 (1H, dd, 7.5, 1.6 Hz), 8.21 (1H, dd, 7.5, 1.6 Hz), 8.00-8.11 (2H, m), 3.47 (3H, s), 2.03 (3H, s).

Ethyl (acetyloxy){[2-(methylsulfonyl)phenyl]sulfonyl}-carbamate (48) is prepared according to Scheme 3. To a stirred solution of N-(acetyloxy)-2-(methylsulfonyl)benzenesulfonamide (0.085 g, 0.29 mmol) in dichloromethane (5 ml) is added triethylamine (50 1, 0.35 mmol) and ethyl chloroformate (30 1, 0.32 mmol). The reaction mixture is stirred for 3 hours before quenching with water (1 ml). The organics are separated and dried over sodium sulfate, filtered and concentrated in vacuo to yield the title compound which is purified by silica column chromatography, eluting with 40% ethyl acetate: heptane. (60 mg, 57%), $^1$H NMR (250 MHz, CHLOROFORM-d) δ ppm 8.47-8.58 (1H, m), 8.34-8.45 (1H, m), 7.82-7.94 (2H, m), 4.25 (2H, q, 7.2 Hz), 3.42 (3H, s), 2.31 (3H, s), 1.25 (3H, t, 7.2 Hz).

Preparation of ethyl (acetyloxy)[(2-bromophenyl)sulfonyl]carbamate (49)

Ethyl (acetyloxy)[(2-bromophenyl)sulfonyl]carbamate (49) is prepared from ethyl chloroformate and N-(acetyloxy)-2-bromobenzenesulfonamide according to Scheme 3. δH (250 MHz, CHLOROFORM-d) δ 8.23-8.37 (1H, m), 7.74-7.85 (1H, m), 7.45-7.60 (2H, m), 4.21 (2H, q, 7.2 Hz), 2.34 (3H, s), 1.19 (3H, t, 7.2 Hz).

Example 6

Synthesis of Compound 52

Scheme 4

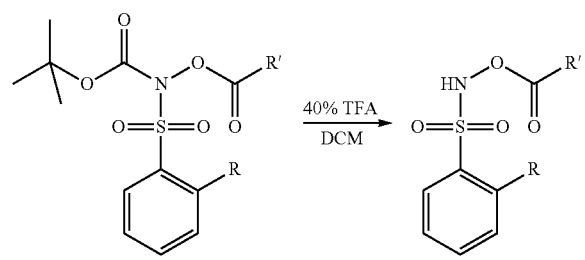

To a solution of the compound formed in Scheme 2 in DCM is added trifluoroacetic acid. The reaction is stirred for 3 h at room temperature and concentrated in vacuo to yield the title compound as a clear, colourless gum. Purification is achieved by trituration from heptane: ethyl acetate.

Scheme 5

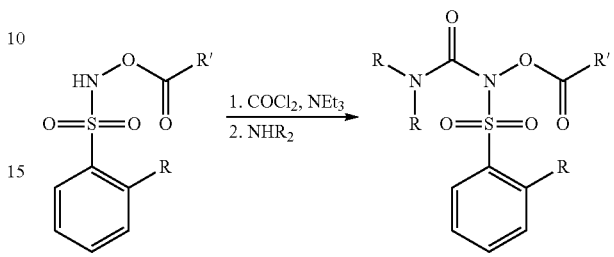

N-[(2,2-Dimethylpropanoyl)oxy]-4-methyl-N-{[2 (methylsulfonyl)phenyl]sulfonyl}piperazine-1-carboxamide (52) is prepared from (2-methanesulfonylbenzene)sulfonamido 2,2-dimethylpropanoate and N-methyl piperazine according to Scheme 5. To a solution of the compound formed in Scheme 4 in DCM cooled to 0° C. is added triethylamine (2 equiv). The solution is stirred at this temperature for 5 minutes before phosgene (a 1.9M solution in toluene, 1.5 equiv) is added. The solution is stirred for a further 45 minutes before quenching with water. The organics are dried over sodium sulfate, filtered and concentrated in vacuo. The crude carbamoyl chloride is redissolved in DCM and triethylamine (1.1 equiv) and a secondary amine (1 equiv) is added. The reaction is stirred at room temperature for 1 h before quenching with water. The organics are dried over sodium sulfate, filtered and concentrated in vacuo. Purification is achieved by trituration with heptane: ethyl acetate. δH (500 MHz, CHLOROFORM-d) δ 8.42 (2H, ddd, 12.3, 7.3, 2.1 Hz), 7.83-7.92 (2H, m), 3.75-3.87 (4H, m), 3.37 (3H, s), 2.53 (4H, t, 4.1 Hz), 2.34 (3H, s), 1.25 (9H, s).

Example 7

Synthesis of Compounds 79-102

Scheme 6

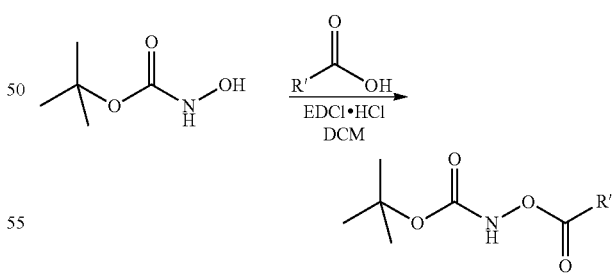

To a stirred solution of N-tert-butoxycarbonyl hydroxylamine (1 equiv) and a carboxylic acid (1 equiv) in DCM (10 vol) is added EDCl.HCl (1 equiv). The reaction mixture is stirred at room temperature until complete consumption of the starting material is observed by tlc. The reaction mixture is washed with water (2×10 vol), dried over sodium sulfate, filtered and concentrated in vacuo. The crude material is purified by column chromatography eluting with heptane: ethyl acetate.

Scheme 7

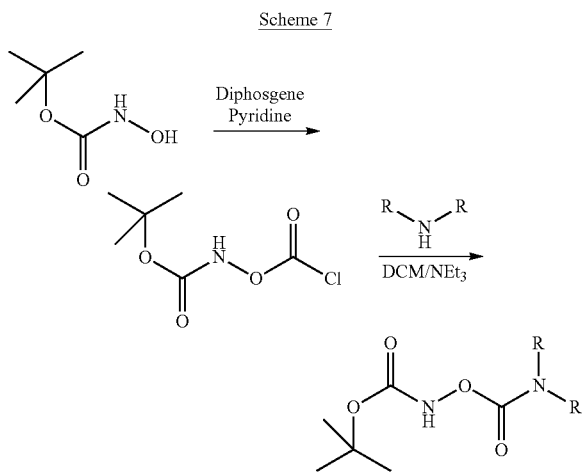

To a solution of tert-butyl N-hydroxycarbamate (1 equiv) in THF (20 vol) is added diphosgene (0.48 equiv) followed by pyridine (1 equiv) dropwise. The reaction mixture is stirred until all starting material is consumed (monitored by tlc), filtered and concentrated in vacuo. The residue is dissolved in DCM (10 vol) and added drop wise to a solution of amine (1 equiv), and triethylamine (1 equiv per basic centre in compound) in DCM (10 vol) at 0° C. The reaction mixture is stirred at room temperature (reaction progress monitored by tlc), before being washed with water (2×10 vol) and re-extracted with further aliquots of DCM (20 vol). The crude product is dried over sodium sulfate, filtered and concentrated in vacuo. The compound is purified directly by either silica column chromatography eluting with heptane: ethyl acetate or DCM: methanol followed by trituration where necessary.

Scheme 8

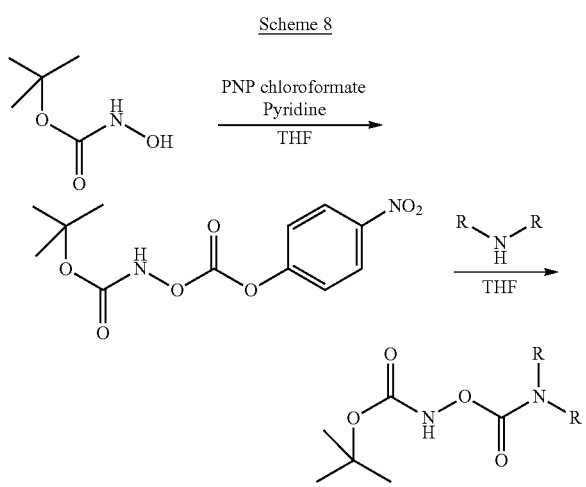

To a solution of tert-butyl N-hydroxycarbamate (1 equiv) in THF (4 vol) and pyridine (1 equiv) at 0° C. is added para-nitrophenyl chloroformate (1 equiv) in THF (2.5 vol) drop wise. The reaction mixture is stirred until all starting material is consumed (monitored by tlc) before being filtered and the amine (1 equiv) is added. The reaction mixture is stirred at room temperature (reaction progress monitored by tlc) and concentrated in vacuo. Compounds without basic centres are dissolved in DCM and washed with NaHCO$_3$ solution (2×10 vol) before being dried over sodium sulfate, filtered and concentrated in vacuo The compound is purified directly by either silica column chromatography eluting with heptane:ethyl acetate or DCM:methanol followed by trituration where necessary or reverse phase preparative HPLC.

Scheme 9

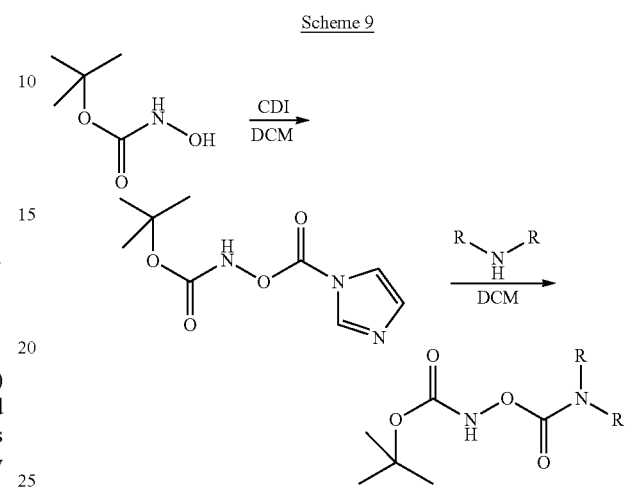

To a solution of tert-butyl N-hydroxycarbamate (0.9 equiv) in DCM (10 vol) is added carbonyldiimidazole (1 equiv). The reaction is stirred at room temperature for 1 hour when the amine (1 equiv) is added. The reaction mixture is stirred at room temperature until starting material is consumed (monitored by tlc) and washed with water (2×5 vol) before being dried over sodium sulfate, filtered and concentrated in vacuo. The compound is purified directly by either silica column chromatography eluting with heptane: ethyl acetate or DCM: methanol

Scheme 10

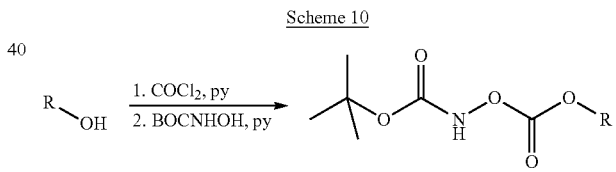

To a solution of an alcohol (1 equiv) in THF (10 vol) cooled to 5° C. is sequentially added a 20% solution of phosgene in toluene (1 equiv) and pyridine (1 equiv). The reaction is stirred for 5 minutes before addition of tert-butyl N-hydroxycarbamate (1 equiv) and pyridine (1 equiv). Stirring is continued at room temperature until all starting material is consumed (monitored by tlc) before the reaction mixture is filtered through Celite™ and the resulting organics concentrated in vacuo. The crude reaction is diluted with diethyl ether (20 vol), washed with 0.1N HCl (5 vol) and water (5 vol), dried over sodium sulfate, filtered and concentrated in vacuo and purified by either silica column chromatography eluting with heptane: ethyl acetate or reverse phase preparative HPLC.

Scheme 11

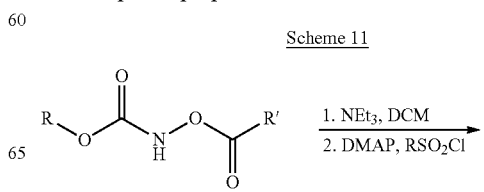

-continued

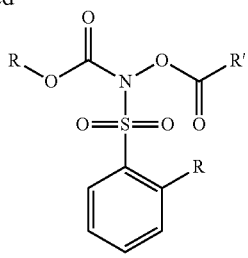

To a solution of N,O-disubstituted hydroxylamine (1 equiv) in DCM (20 vol) and triethylamine (1 equiv) is added dimethylaminopyridine (0.1 equiv) and a sulfonyl chloride (1 equiv). The reaction mixture is stirred at room temperature until complete consumption of the sulfonyl chloride is observed by tlc, whereupon the reaction mixture is quenched by the addition of water (10 vol) and extracted into DCM (10 vol). The combined organics are washed with water (10 vol), dried over sodium sulfate, filtered and concentrated in vacuo and either used directly without additional purification or purified directly by either silica column chromatography eluting with heptane: ethyl acetate or reverse phase preparative HPLC.

Preparation of N-[(tert-butoxy)carbonyl](2-methanesulfonylbenzene)sulfonamido (2S)-2-{[(tert butoxy)carbonyl](methyl)amino}-4-methylpentanoate (79)

[(tert-Butoxy)carbonyl]amino (2S)-2-{[(tert-butoxy)carbonyl](methyl)amino}-4-methylpentanoate is prepared from (2S)-2-{[(tert-butoxy)carbonyl](methyl)amino}-4-methylpentanoic acid and N-tert-butoxycarbonyl hydroxylamine according to Scheme 6. The compound exists as rotomers and is reported as such. (1.8 g, 58%), $^1$H NMR (500 MHz, CHLOROFORM-d) δ ppm 7.49-8.06 (1H, m), 4.75-5.10 (1H, m), 2.86 (3H, d, 7.8 Hz), 1.66-1.88 (2H, m), 1.54-1.64 (1H, m), 1.50 (9H, s), 1.47 (9H, d, 3.7 Hz), 0.96 (6H, dd, 10.7, 6.6 Hz).

N-[(tert-Butoxy)carbonyl](2-methanesulfonylbenzene)sulfonamido (2S)-2-{[(tert butoxy) carbonyl](methyl)amino}-4-methylpentanoate (79) is synthesised from 2-methanesulfonylbenzene sulfonyl chloride and [(tert-butoxy)carbonyl]amino (2S)-2-{[(tert-butoxy)carbonyl](methyl)amino}-4-methylpentanoate according to Scheme 11. (0.51 g, 63%), $^1$H NMR (500 MHz, CHLOROFORM-d) δ ppm 8.34-8.48 (2H, m), 7.80-7.90 (2H, m), 4.94-5.31 (1H, m), 3.42 (3H, d, 9.3 Hz), 2.77-2.92 (3H, m), 1.73-1.93 (2H, m), 1.58-1.68 (1H, m), 1.47 (9H, d, 6.4 Hz), 1.41 (9H, s), 0.98 (6H, t, 7.4 Hz).

Preparation of N-[(tert-butoxy)carbonyl](2-methanesulfonylbenzene)sulfonamido (2R)-2-{[(tert-butoxy)carbonyl](methyl)amino}propanoate (80)

[(tert-Butoxy)carbonyl]amino (2R)-2-{[(tert-butoxy)carbonyl](methyl)amino}propanoate is prepared from (2R)-2-{[(tert-butoxy)carbonyl](methyl)amino}propanoic acid and N-tert-butoxycarbonyl hydroxylamine according to Scheme 6. The compound exists as rotomers and is reported as such. (0.95 g, 60%), $^1$H NMR (500 MHz, CHLOROFORM-d) δ ppm 7.81-7.95 (1H, m), 4.60-5.04 (1H, m), 2.85-2.93 (3H, m), 1.40-1.54 (18H, m), 1.22-1.33 (3H, m).

N-[(tert-Butoxy)carbonyl](2-methanesulfonylbenzene)sulfonamido (2R)-2-{[(tert-butoxy)carbonyl](methyl)amino}propanoate (80) is synthesised from 2-methanesulfonyl benzene sulfonyl chloride and [(tert-butoxy)carbonyl]amino (2R)-2-{[(tert-butoxy) carbonyl](methyl)amino}propanoate according to Scheme 11. (0.71 g, 44%), $^1$H NMR (500 MHz, CHLOROFORM-d) δ ppm 8.23-8.50 (2H, m), 7.78-7.99 (2H, m), 4.79-5.34 (1H, m), 3.39-3.51 (3H, m), 2.59-2.95 (3H, m), 1.47 (9H, s), 1.41 (9H, s), 1.27 (3H, t, 7.2 Hz).

Preparation of N-[(tert-butoxy)carbonyl](2-methanesulfonylbenzene)sulfonamido (2S)-2-{[(tert-butoxy)carbonyl](methyl)amino}propanoate (81)

[(tert-Butoxy)carbonyl]amino (2S)-2-{[(tert-butoxy)carbonyl](methyl)amino}-propanoate is prepared from (2S)-2-{[(tert-butoxy)carbonyl](methyl)amino}propanoic acid and N-tert-butoxycarbonyl hydroxylamine according to Scheme 6. (0.96 g, 61%), The compound exists as rotomers and is reported as such. $^1$H NMR (500 MHz, CHLOROFORM-d) δ ppm 7.73-7.89 (1H, m), 4.61-5.04 (1H, m), 2.86-2.96 (3H, m), 1.41-1.53 (21H, m).

N-[(tert-Butoxy)carbonyl](2-methanesulfonylbenzene) sulfonamido (2S)-2-{[(tert-butoxy)carbonyl](methyl)amino}propanoate (81) is synthesised from 2-methanesulfonyl benzene sulfonyl chloride [(tert-butoxy)carbonyl]amino (2S)-2-{[(tert-butoxy)carbonyl](methyl)amino}propanoate according to Scheme 11. (0.03 g, 18%), $^1$H NMR (500 MHz, CHLOROFORM-d) δ ppm 8.21-8.53 (2H, m), 7.73-8.02 (2H, m), 4.81-5.40 (1H, m), 3.36-3.51 (3H, m), 2.60-2.98 (3H, m), 1.47 (9H, s), 1.33-1.44 (12H, m).

Preparation of N-[(tert-butoxy)carbonyl](2-methanesulfonylbenzene)sulfonamido 2-{[(tertbutoxy)carbonyl](methyl)amino}acetate (82)

[(tert-Butoxy)carbonyl]amino 2-{[(tert-utoxy)carbonyl](methyl)amino}acetate is prepared from {[(tert-butoxy)carbonyl](methyl)amino}acetate and N-tert-butoxycarbonyl hydroxylamine according to Scheme 6. The compound exists as rotomers and is reported as such. (1.5 g, 93%), $^1$H NMR (500 MHz, CHLOROFORM-d) δ ppm 7.92 (1H, d, m), 4.03-4.23 (2H, m), 2.95-3.01 (3H, m), 1.41-1.54 (18H, m).

N-[(tert-Butoxy)carbonyl](2-methanesulfonylbenzene) sulfonamido 2-{[(tert-butoxy)carbonyl](methyl)amino}acetate (82) is synthesised from 2-methanesulfonyl benzene sulfonyl chloride and [(tert-butoxy)carbonyl]amino 2-{[(tert-butoxy)carbonyl](methyl)amino}-acetate according to Scheme 11. (1.3 g, 51%), $^1$H NMR (500 MHz, CHLOROFORM-d) δ ppm 8.48 (1H, dd, 7.5, 1.5 Hz), 8.35-8.44 (1H, m), 7.81-7.93 (2H, m), 3.90-4.63 (2H, m), 3.42 (3H, d, J=2.0 Hz), 2.97 (3H, d, 14.2 Hz), 1.41-1.50 (18H, m) Preparation of N-[(tert-butoxy)carbonyl](2-methanesulfonylbenzene)sulfonamido (2S)-2-{[(tert-butoxy)carbonyl](methyl)amino}-3-methylbutanoate (83) [(tert-Butoxy)carbonyl]amino (2S)-2-{[(tert-butoxy)carbonyl](methyl)amino}-3-methylbutanoate is prepared from (2S)-2-{[(tert-butoxy)carbonyl](methyl)amino}-3-methylbutanoate and N-tert-butoxycarbonyl hydroxylamine according to Scheme 6. The compound exists as rotomers and is reported as such. (1.18 g, 42%), $^1$H NMR (500 MHz, CHLOROFORM-d) δ ppm 7.50-8.11 (1H, m), 4.02-4.94 (1H, m), 3.49-3.50 (3H, m), 2.07-2.41 (1H, m), 1.37-1.55 (18H, m), 0.83-1.17 (6H, m).

N-[(tert-Butoxy)carbonyl](2-methanesulfonylbenzene) sulfonamido (2S)-2-{[(tert-butoxy)carbonyl](methyl)amino}-3-methylbutanoate (83) is synthesised from 2-methanesulfonyl benzene sulfonyl chloride [(tert-butoxy)carbonyl]amino (2S)-2-{[(tert-butoxy)carbonyl]-(methyl)amino}-3-methylbutanoate according to Scheme 11. 0.68 g, 68%), $^1$H NMR (250 MHz, CHLOROFORM-d) δ ppm 8.31-8.50 (2H, m), 7.77-7.97 (2H, m), 4.25-5.02 (1H, m), 3.31-3.47 (3H, m), 2.79-2.93 (3H, m), 2.21-2.41 (1H, m), 1.36-1.52 (18H, m), 1.03-1.12 (3H, m), 0.91-1.00 (3H, m)

Preparation of N-[(tert-butoxy)carbonyl][(4-chlorophenyl)methane]sulfonamido 2,2-dimethylpropanoate (84)

N-[(tert-Butoxy)carbonyl][(4-chlorophenyl)methane]sulfonamido 2,2 dimethyl propanoate (84) is prepared from (4-chlorophenyl)methanesulfonyl chloride and [(tert-butoxy)carbonyl]amino 2,2-dimethylpropanoate according to Scheme 11. (0.4 g, 32%), $^1$H NMR (500 MHz, CHLOROFORM-d) δ ppm 7.33-7.43 (4H, m), 4.56-5.04 (2H, m), 1.55 (9H, s), 1.29 (9H, s).

Preparation of N-[(benzyloxy)carbonyl](2-methanesulfonylbenzene)sulfonamido 2,2-dimethylpropanoate (85)

[(Benzyloxy)carbonyl]amino 2,2-dimethylpropanoate

To a solution of benzyl hydroxycarbamate (1 g, 5.98 mmol) in DCM (20 ml) is added triethylamine (0.6 g, 5.98 mmol) and 2,2-dimethylpropanoyl chloride (0.74 ml, 5.98 mmol). After 2 hours the reaction mixture is quenched by the addition of water (10 ml) and the organics are extracted into DCM (2×20 ml), dried over sodium sulfate, filtered and concentrated in vacuo to yield the title compound as a yellow oil which is used without any further purification. (1.6 g, 100%), $^1$H NMR (500 MHz, CHLOROFORM-d) δ ppm 8.02 (1H, br. s.), 7.29-7.43 (5H, m), 5.22 (2H, s), 1.30 (9H, s).

N-[(Benzyloxy)carbonyl](2-methanesulfonylbenzene)sulfonamido 2,2-dimethylpropanoate (85) is prepared from 2-methylsulfonylbenzenesulfonyl chloride and [(benzyloxy)carbonyl]amino 2,2-dimethylpropanoate according to Scheme 11. (0.9 g, 15%), $^1$H NMR (500 MHz, CHLOROFORM-d) δ ppm 8.42 (1H, dd, 8.0, 0.9 Hz), 8.35 (1H, dd, 7.9, 1.3 Hz), 7.83 (1H, td, 7.6, 1.3 Hz), 7.72 (1H, td, 7.7, 1.3 Hz), 7.30-7.36 (3H, m), 7.21 (2H, dd, 7.4, 1.9 Hz), 5.15 (2H, d, 19.7 Hz), 3.32 (3H, s), 1.32 (9H, s).

Preparation of N-[(tert-butoxy)carbonyl](2-methanesulfonylbenzene)sulfonamido N,N-dimethylcarbamate (86)

[(tert-Butoxy)carbonyl]amino N,N-dimethylcarbamate is prepared from tert-butyl N-hydroxycarbamate and dimethyl carbamoyl chloride according to Scheme 1. (2.4 g, 78%), $^1$H NMR (500 MHz, CHLOROFORM-d) δ ppm 7.82 (1H, br. s.), 3.02 (3H, s), 2.98 (3H, s), 1.49 (9H, s)

N-[(tert-Butoxy)carbonyl](2-methanesulfonylbenzene)sulfonamido-N,N-dimethyl carbamate (86) is prepared from [(tert-butoxy)carbonyl]amino N,N-dimethylcarbamate and 2-methylsulfonylbenzenesulfonyl chloride according to Scheme 11. (0.45 g, 42%), $^1$H NMR (500 MHz, CHLOROFORM-d) δ ppm 8.54-9.01 (1H, m), 8.32-8.44 (1H, m), 7.76-7.90 (2H, m), 3.42 (3H, s), 3.09 (3H, s), 3.03 (3H, s), 1.41 (9H, s).

Alternatively, N-[(tert-butoxy)carbonyl](2-methanesulfonylbenzene)-sulfonamido-N,N-dimethyl carbamate (86) is prepared via the following method:

A solution of [(tert-butoxy)carbonyl]amino N,N-dimethylcarbamate (1g, 4.9 mmol) in THF (5 ml) is added dropwise to a stirred solution of sodium hydride (60% dispersion in oil, 0.24 g, 5.2 mmol) in THF (25 ml). Stirring is continued for 30 minutes, whereupon 2-methylsulfonylbenzenesulfonyl chloride (1.35 g, 5.4 mmol) is added. The reaction mixture is stirred at room temperature for 3 hours after which time tlc (1:1 heptane: ethyl acetate) showed no starting material remained. The reaction mixture is quenched by the addition of water (5 ml) and extracted into diethyl ether (2×20 ml). The combined organics are dried over sodium sulfate, filtered and concentrated in vacuo to yield the desired material, which is purified by silica column chromatography eluting with heptane: ethyl acetate (1:1; v:v) (1.1 g, 53%).

Preparation of N-[(tert-butoxy)carbonyl](2-bromobenzene)sulfonamido N,N-dimethylcarbamate (87)

N-[(tert-Butoxy)carbonyl](2-bromobenzene)sulfonamido N,N-dimethylcarbamate (87) is prepared from [(tert-butoxy)carbonyl]amino N,N-dimethylcarbamate and 2-bromobenzenesulfonyl chloride according to Scheme 11. (0.655 g, 37%), $^1$H NMR (250 MHz, CHLOROFORM-d) δ ppm 8.25-8.37 (1H, m), 7.71-7.82 (1H, m), 7.44-7.55 (2H, m), 3.02 (3H, s), 2.99 (3H, s), 1.50 (9H, s).

Preparation of N-[(tert-butoxy)carbonyl](2-methanesulfonylbenzene)sulfonamido morpholine-4-carboxylate (88)

[(tert-Butoxy)carbonyl]amino morpholine-4-carboxylate is prepared from morpholine-4-carbonyl chloride and according to Scheme 1. (1.71 g, 105%), $^1$H NMR (500 MHz, CHLOROFORM-d) δ ppm 7.78 (1H, s), 3.66-3.78 (4H, m), 3.46-3.65 (4H, m), 1.50 (9H, s).

N-[(tert-Butoxy)carbonyl](2-methanesulfonylbenzene)sulfonamido morpholine-4-carboxylate (88) is prepared from [(tert-butoxy)carbonyl]amino morpholine-4-carboxylate and 2-methylsulfonylbenzenesulfonyl chloride according to Scheme 11. (1.12 g, 61%), $^1$H NMR (500 MHz, CHLOROFORM-d) δ ppm 8.54-8.66 (1H, m), 8.32-8.43 (1H, m), 7.74-7.91 (2H, m), 3.49-3.86 (8H, m), 3.41 (3H, s), 1.43 (9H, s).

Preparation N-[(tert-butoxy)carbonyl](2-methanesulfonylbenzene)sulfonamido 4-acetylpiperazine-1-carboxylate (89)

[(tert-Butoxy)carbonyl]amino 4-acetylpiperazine-1-carboxylate is prepared according to Scheme 7. To a solution of tert-butyl N-hydroxycarbamate (1.0 g, 7.44 mmol) in THF (20 ml) is added diphosgene (0.44 ml, 3.57 mmol) followed by pyridine (0.6 ml, 7.44 mmol) drop wise. The reaction mixture is stirred for 1 hour at room temperature, filtered and concentrated. The residue is dissolved in DCM (10 ml) and added drop wise to a solution of 4-acetylpiperazine (0.95 g, 7.44 mmol), in triethylamine (1.0 ml, 7.44 mmol) and DCM (10 ml) at 0° C. The reaction mixture is stirred at room temperature for 18 hours. The reaction mixture is washed with water (2×2 ml), dried over sodium sulfate, filtered and concentrated in vacuo. The title compound is purified directly by silica column chromatography eluting with ethyl acetate yielding the title compound as a white solid. (0.75 g, 35%), $^1$H NMR (500 MHz, CHLOROFORM-d) δ ppm 7.70 (1H, br. s.), 3.24-3.68 (8H, m), 2.06 (3H, s), 1.43 (9H, s).

N-[(tert-Butoxy)carbonyl](2-methanesulfonylbenzene)sulfonamido 4-acetylpiperazine-1-carboxylate (89) is prepared from [(tert-butoxy)carbonyl]amino 4-acetylpiperazine-1-carboxylate and 2-methylsulfonylbenzenesulfonyl chloride according to Scheme 11. (0.89 g, 70%), $^1$H NMR (500 MHz, CHLOROFORM-d) δ ppm 8.45-8.62 (1H, m), 8.23-8.37 (1H, m), 7.72-7.83 (2H, m), 3.35-3.75 (8H, m), 3.32 (3H, s), 2.04-2.10 (3H, m), 1.35 (9H, s)

Preparation of N-[(tert-butoxy)carbonyl](2-methanesulfonylbenzene)sulfonamido N-cyclohexyl-N-methylcarbamate (90)

tert-Butyl N-{[cyclohexyl(methyl)carbamoyl]oxy}carbamate is prepared according to Scheme 8.

To a solution of tert-butyl N-hydroxycarbamate (2.0 g, 15.0 mmol) in THF (8 ml) and pyridine (1.2 ml, 15.0 mmol)) at 0° C. is added para-nitrophenyl chloroformate (3.0 g, 15.0 mmol) in THF (7.5 ml) drop wise. The reaction mixture is stirred for 1 hour before being filtered and N-methylcyclohexanamine (1.96 ml, 15.0 mmol) added. The reaction mixture is stirred at room temperature for 18 hours and concentrated in vacuo. Dissolved in DCM (20 ml) and washed with NaHCO$_3$ solution (2×5 ml) before being dried over sodium sulfate, filtered and concentrated in vacuo, the title compound is purified directly by silica column chromatography eluting with DCM: methanol and taken to the next step with no further purification (0.81 g).

N-[(tert-Butoxy)carbonyl](2-methanesulfonylbenzene)sulfonamido N-cyclohexyl-N-methylcarbamate (90) is prepared from 2-ethylsulfonylbenzenesulfonyl chloride and tert-butyl N-{[cyclohexyl(methyl)carbamoyl]oxy}carbamate according to Scheme 11. (0.44 g, 6% over two steps), $^1$H NMR (500 MHz, CHLOROFORM-d) δ ppm 8.52-8.65 (1H, m), 8.23-8.36 (1H, m), 7.69-7.82 (2H, m), 3.79-4.00 (1H, m), 3.34 (3H, s), 2.86 (3H, s), 0.90-1.88 (19H, m).

Preparation of 1-N-[(tert-butoxy)carbonyl](2-methanesulfonylbenzene)sulfonamido 4-tert-butyl piperazine-1,4-dicarboxylate (91)

1-[(tert-Butoxy)carbonyl]amino 4-tert-butyl piperazine-1,4-dicarboxylate is prepared from tert-butyl N-hydroxycarbamate and tert-butyl piperazine-1-carboxylate according to Scheme 8. (0.75 g, 35%), $^1$H NMR (250 MHz, CHLOROFORM-d) δ ppm 7.76 (1H, s), 3.43-3.62 (8H, m), 1.50 (9H, s), 1.48 (9H, s).

1-N-[(tert-Butoxy)carbonyl](2-methanesulfonylbenzene)sulfonamido 4-tert-butyl piperazine-1,4-dicarboxylate (91) is prepared from 2-methylsulfonylbenzenesulfonyl chloride and 1-[(tert-butoxy)carbonyl]amino 4-tert-butyl piperazine-1,4-dicarboxylate according to Scheme 11. (0.86 g, 57%), $^1$H NMR (500 MHz, CHLOROFORM-d) δ ppm 8.52-8.67 (1H, m), 8.31-8.49 (1H, m), 7.76-7.96 (2H, m), 3.45-3.78 (8H, m), 3.40 (3H, s), 1.48 (9H, s), 1.42 (9H, s).

Preparation of N-[(tert-butoxy)carbonyl](2-methanesulfonylbenzene)sulfonamido N-(2-methoxyethyl)carbamate (92)

[(tert-Butoxy)carbonyl]amino N-(2-methoxyethyl)carbamate is prepared from tert-butyl N-hydroxycarbamate and (2-methoxyethyl)(methyl)amine according to Scheme 7. (0.58 g, 32%), $^1$H NMR (500 MHz, CHLOROFORM-d) δ ppm 7.79 (1H, s), 3.46-3.64 (4H, m), 3.36 (3H, d, 4.4 Hz), 3.06 (3H, d, 10.6 Hz), 1.50 (9H, s)

N-[(tert-Butoxy)carbonyl](2-methanesulfonylbenzene)sulfonamido N-(2-methoxyethyl) carbamate (92) is prepared from 2-methylsulfonylbenzenesulfonyl chloride and [(tert-butoxy)carbonyl]amino N-(2-methoxyethyl)carbamate according to Scheme 11 (0.58 g, 53%), $^1$H NMR (500 MHz, CHLOROFORM-d) δ ppm 8.63-8.73 (1H, m), 8.29-8.42 (1H, m), 7.86 (2H, dd, 5.8, 3.2 Hz), 3.50-3.75 (4H, m), 3.43 (3H, d, 4.4 Hz), 3.38 (3H, d, 4.6 Hz), 3.14 (3H, d, 14.0 Hz), 1.42 (9H, s).

Preparation of N-[(tert-butoxy)carbonyl](2-methanesulfonylbenzene)sulfonamido N,N diethylcarbamate (93)

[(tert-Butoxy)carbonyl]amino N,N-diethylcarbamate is prepared from tert-butyl N-hydroxycarbamate and diethyl carbamoyl chloride according to Scheme 1. (0.67 g, 39%), $^1$H NMR (500 MHz, CHLOROFORM-d) δ ppm 7.84 (1H, br. s.), 3.33 (4H, q, 7.1 Hz), 1.48 (9H, s), 1.11-1.28 (6H, m).

N-[(tert-Butoxy)carbonyl](2-methanesulfonylbenzene)sulfonamido N,N diethylcarbamate (93) is prepared from [(tert-butoxy)carbonyl]amino N,N-diethylcarbamate and 2-methylsulfonylbenzenesulfonyl chloride according to Scheme 11. (0.47 g, 36%), $^1$H NMR (500 MHz, CHLOROFORM-d) δ ppm 8.55-8.70 (1H, m), 8.29-8.36 (1H, m), 7.77-7.87 (2H, m), 3.18-3.52 (7H, m), 1.35 (9H, s), 1.22 (3H, t, 7.1 Hz), 1.16 (3H, t, 7.0 Hz).

Preparation of N-[(tert-butoxy)carbonyl](2-methanesulfonylbenzene)sulfonamido N-methoxy-N-methylcarbamate (94)

[(tert-Butoxy)carbonyl]amino N-methoxy-N-methylcarbamate is prepared from tert-butyl N-hydroxycarbamate and N-Methoxy-N-methylcarbamoyl chloride according to Scheme 1. (2.48 g, 100%), $^1$H NMR (500 MHz, CHLOROFORM-d) δ ppm 7.83 (1H, s), 3.76 (3H, s), 3.23 (3H, s), 1.48 (9H, s).

N-[(tert-Butoxy)carbonyl](2-methanesulfonylbenzene)sulfonamido N-methoxy-N-methylcarbamate (94) is prepared from [(tert-butoxy)carbonyl]amino N-methoxy-N-methylcarbamate and 2-methylsulfonylbenzenesulfonyl chloride according to Scheme 11. $^1$H NMR (500 MHz, CHLOROFORM-d) δ ppm 8.55-8.63 (1H, m), 8.34-8.42 (1H, m), 7.81-7.88 (2H, m), 3.80 (3H, s), 3.42 (3H, s), 3.30 (3H, s), 1.42 (9H, s).

Preparation of tert-butyl N-[(2-methanesulfonylbenzene)sulfonyl]-N-{[methyl(pyridin-3-ylmethyl) carbamoyl]oxy}carbamate (95)

tert-Butyl N-{[methyl(pyridin-3-ylmethyl)carbamoyl]oxy}carbamate is prepared from tert-butyl N-hydroxycarbamate and methyl(pyridin-3-ylmethyl)amine according to Scheme 1. This material is used in the synthesis of tert-butyl N-[(2-methanesulfonylbenzene)sulfonyl]-N-{[methyl(pyridin-3-ylmethyl)carbamoyl]oxy}carbamate without further purification (0.52 g).

tert-Butyl N-[(2-methanesulfonylbenzene)sulfonyl]-N-{[methyl(pyridin-3-ylmethyl) carbamoyl]oxy}carbamate (95) is prepared from tert-butyl N-{[methyl(pyridin-3-ylmethyl)carbamoyl]oxy}carbamate and 2-methylsulfonylbenzenesulfonyl chloride according to Scheme 7. (0.26 g, 7% over two steps), $^1$H NMR (500 MHz, CHLOROFORM-d) δ ppm 8.54-8.82 (3H, m), 8.28-8.46 (1H, m), 7.94-8.19 (1H, m), 7.80-7.94 (2H, m), 7.54 (1H, br. s.), 4.53-4.84 (2H, m), 3.42 (3H, s), 2.93-3.18 (3H, m), 1.44 (9H, s).

Preparation of tert-butyl 2-{[2-(tert-butoxy)-2-oxoethyl][(N-[(tert-butoxy)carbonyl](2-methanesulfonylbenzene)sulfonamido oxy)carbonyl] amino}acetate (96)

tert-Butyl 2-{[2-(tert-butoxy)-2-oxoethyl][({[(tert-butoxy)carbonyl]amino}oxy)carbonyl]amino}acetate is prepared from tert-butyl N-hydroxycarbamate and di-tert-butyl 2,2'-iminodiacetate according to Scheme 9. (2.46 g, 59.7%), $^1$H NMR (500 MHz, CHLOROFORM-d) δ ppm 7.72 (1H, s), 4.08 (2H, s), 4.04 (2H, s), 1.41-1.51 (27H, m).

tert-Butyl 2-{[2-(tert-butoxy)-2-oxoethyl][({N-[(tert-butoxy)carbonyl](2-methane sulfonylbenzene) sulfonamido}oxy)carbonyl]amino}acetate (96) is prepared from tert-butyl 2-{[2-(tert-butoxy)-2-oxoethyl][({[(tert-butoxy)carbonyl]amino}oxy)carbonyl]amino}acetate and 2-methylsulfonylbenzenesulfonyl chloride according to Scheme 11. (0.74 g, 13.6%), $^1$H NMR (500 MHz, CHLOROFORM-d) δ ppm 8.48-8.55 (1H, m), 8.27-8.31 (1H, m), 7.71-7.80 (2H, m), 3.90-4.13 (4H, m), 3.33 (3H, s), 1.42 (9H, s), 1.40 (9H, s), 1.34 (9H, s).

Preparation of 4-{[({N-[(tert-butoxy)carbonyl](2-methanesulfonyl benzene)sulfonamido}oxy)carbonyl]oxy}oxane (97)

4-{[({[(tert-Butoxy)carbonyl]amino}oxy)carbonyl]oxy}oxane is prepared according to Scheme 9. To a solution of tetrahydropyran-4-ol (2 g, 19.6 mmol) in THF (20 mL) cooled to 5° C. is sequentially added a 20% solution of phosgene in toluene (10.3 mL, 19.6 mmol) and pyridine (1.6 mL, 19.6 mmol). The reaction is stirred for 5 minutes before addition of tert-butyl N-hydroxycarbamate (2.6 g, 19.6 mmol) and pyridine (1.6 mL, 19.6 mmol). Stirring is continued for 30 minutes at room temperature before the reaction mixture is filtered through Celite™ and the resulting organics concentrated in vacuo. The crude reaction is diluted with diethyl ether (50 mL), washed with 0.1N HCl (10 ml) and water (10 ml), dried over sodium sulfate, filtered and concentrated in vacuo. Purification is achieved by silica gel column chromatography eluting with heptane: ethyl acetate (1:1; v:v) to yield the title compound as a clear, colourless oil. (3.64 g, 71%), $^1$H NMR (500 MHz, CHLOROFORM-d) δ ppm 7.78 (1H, s), 4.92 (1H, tt, 8.4, 4.0 Hz), 3.88-3.98 (2H, m), 3.55 (2H, ddd, 11.8, 8.7, 3.1 Hz), 1.98-2.09 (2H, m), 1.80 (2H, m), 1.50 (9H, s).

4-{[({N-[(tert-Butoxy)carbonyl](2methanesulfonylbenzene)sulfonamido}oxy)-carbonyl]oxy}oxane (97) is prepared from 4-{[({[(tertbutoxy)carbonyl]amino}oxy)-carbonyl]oxy}oxane and 2-methylsulfonylbenzenesulfonyl chloride according to Scheme 11. (0.5 g, 27% yield), $^1$H NMR (250 MHz, CHLOROFORM-d) δ ppm 8.36-8.49 (2H, m), 7.83-7.90 (2H, m), 4.91-5.04 (1H, m), 3.87-4.02 (2H, m), 3.51-3.64 (2H, m), 3.43 (3H, s), 1.98-2.13 (2H, m), 1.74-1.94 (2H, m), 1.58 (9H, s).

Preparation of 4-{[({N-[(tert-butoxy)carbonyl](2-bromobenzene)sulfonamido}oxy)carbonyl]-oxy}oxane (98)

4-{[({N-[(tert-Butoxy)carbonyl](2-bromobenzene) sulfonamido}oxy)carbonyl]oxy}oxane (98) is synthesised from 2-bromobenzene sulfonyl chloride and 4-{[({[(tert-butoxy)carbonyl]amino}oxy)carbonyl]oxy}oxane according to Scheme 11. (1.17 g, 77%), $^1$H NMR (500 MHz, CHLOROFORM-d) δ ppm 8.22-8.30 (1H, m), 7.76-7.84 (1H, m), 7.47-7.57 (2H, m), 4.98-5.11 (1H, m), 3.91-4.02 (2H, m), 3.52-3.64 (2H, m), 1.98-2.14 (2H, m), 1.73-1.93 (2H, m), 1.39 (9H, s).

Preparation of 1-({[(tert-butoxy)carbonyl][(methoxycarbonyl)oxy]amino}sulfonyl)-2-methanesulfonyl benzene (99)

2-({[(Methoxycarbonyl)oxy]carbamoyl}oxy)-2-methylpropane

To a solution of tert-butyl N-hydroxycarbamate (1.4 g, 10.6 mmol) in DCM (10 ml) is added triethylamine (1.5 ml, 10.6 mmol) at 0° C. Methyl chloroformate (814 µl, 10.6 mmol) is added drop wise. Reaction stirred for 18 hours at room temperature before being washed with water (2×10 ml), NaHCO$_3$ (2×10 ml), dried over magnesium sulfate and concentrated in vacuo to give the title product as an oil. (1.76 g, 87%), $^1$H NMR (500 MHz, CHLOROFORM-d) δ ppm 7.71 (1H, br. s.), 3.92 (3H, s), 1.50 (9H, s).

1-({[(tert-Butoxy)carbonyl][(methoxycarbonyl)oxy] amino}sulfonyl)-2-methanesulfonyl benzene (99) is prepared from 2-({[(methoxycarbonyl)oxy]-carbamoyl}oxy)-2-methylpropane according to Scheme 11. (0.96 g, 60%), $^1$H NMR (500 MHz, CHLOROFORM-d) δ ppm 8.38-8.47 (2H, m), 7.82-7.90 (2H, m), 3.99 (3H, s), 3.42 (3H, s), 1.40-1.47 (9H, m).

Preparation of 1-({[(tert-butoxy)carbonyl]({[(2-methoxyethoxy)carbonyl]oxy})amino}sulfonyl)-2-methanesulfonylbenzene (100)

1-{[({[(tert-Butoxy)carbonyl]amino}oxy)carbonyl] oxy}-2-methoxyethane

To a solution of tert-butyl N-hydroxycarbamate (1.5 g, 11.3 mmol) in DCM (50 ml) is added triethylamine (1.6 ml, 11.3 mmol) at 0° C. Chloro(2-methoxyethoxy)methanone (1.56 g, 11.3 mmol) is added dropwise. Reaction is stirred for 18 hours at room temperature before being washed with water (2×10 ml), NaHCO$_3$ (2×10 ml), dried (MgSO$_4$) and concentrated in vacuo to give the title product as an oil. (0.67 g, 25%), $^1$H NMR (500 MHz, CHLOROFORM-d) δ ppm 7.74-8.46 (1H, m), 4.23-4.73 (2H, m), 3.45-3.84 (2H, m), 3.34 (3H, s), 1.41 (9H, s).

1-({[(tert-Butoxy)carbonyl]({[(2-methoxyethoxy)carbonyl]oxy})amino}-sulfonyl)-2-methanesulfonylbenzene (100) is prepared from 1-{[({[(tert-butoxy)carbonyl] amino}oxy) carbonyl]oxy}-2-methoxyethane and 2-methylsulfonyl benzenesulfonyl chloride according to Scheme 11. (0.59 g, 46%), $^1$H NMR (500 MHz, CHLOROFORM-d) δ ppm 8.16-8.80 (2H, m), 7.54-8.02 (2H, m), 4.47-4.47 (2H, m), 3.66 (2H, d, 4.1 Hz), 3.41 (3H, s), 3.38 (3H, s), 1.42 (9H, s)

Preparation of 1-({[(tert-butoxy)carbonyl]({[2-(2-methoxyethoxy)ethoxy]carbonyl}oxy)-amino}sulfonyl)-2-methanesulfonylbenzene (101)

1-(2-{[({[(tert-Butoxy)carbonyl]amino}oxy)carbonyl] oxy}ethoxy)-2-methoxyethane is prepared from tert-butyl N-hydroxycarbamate and 2-(2-methoxyethoxy)ethanol using 20% solution of phosgene in toluene according to Scheme 10. (9.95 g, 82%), $^1$H NMR (250 MHz, CHLORO- FORM-d) δ ppm 7.88 (1H, s), 4.36-4.45 (2H, m), 3.72-3.80 (2H, m), 3.61-3.68 (2H, m), 3.51-3.58 (2H, m), 3.37 (3H, s), 1.49 (9H, s).

1-({[(tert-Butoxy)carbonyl]({[2-(2-methoxyethoxy)ethoxy]carbonyl}oxy)-amino}sulfonyl)-2-methanesulfonylbenzene (101) is prepared from 1-(2-{[({[(tert-butoxy)carbonyl]amino}oxy)carbonyl]oxy}ethoxy)-2-methoxyethane and 2-methylsulfonyl benzene sulfonyl chloride according to Scheme 11. (2.72 g, 70%), $^1$H NMR (500 MHz, CHLOROFORM-d) δ ppm 8.40 (2H, ddd, 12.7, 7.5, 1.5 Hz), 7.86 (2H, m), 4.37-4.56 (2H, m), 3.71-3.85 (2H, m), 3.62-3.71 (2H, m), 3.50-3.60 (2H, m), 3.43 (3H, s), 3.39 (3H, s), 1.43 (9H, s).

Preparation of 1-({[(tert-butoxy)carbonyl]({[(1,3-diethoxypropan-2-yl)oxy]carbonyl}oxy)-amino}sulfonyl)-2-methanesulfonylbenzene (102)

2-{[({[(tert-Butoxy)carbonyl]amino}oxy)carbonyl]oxy}-1,3-diethoxypropane is prepared from tert-butyl N-hydroxycarbamate and 1,3-diethoxypropan-2-ol using 20% solution of phosgene in toluene according to Scheme 10. (10.37 g, 85%), $^1$H NMR (500 MHz, CHLOROFORM-d) δ ppm 7.73 (1H, s), 5.03 (1H, quin, 5.2 Hz), 3.64 (4H, dd, 5.1, 2.7 Hz), 3.48-3.57 (4H, m), 1.50 (9H, s), 1.19 (6H, t, 7.0 Hz).

1-({[(tert-Butoxy)carbonyl]({[(1,3-diethoxypropan-2-yl)oxy]carbonyl}oxy)-amino}sulfonyl)-2-methanesulfonylbenzene (102) is prepared from 2-{[({[(tert-butoxy)carbonyl]amino}oxy)carbonyl]oxy}-1,3-diethoxypropane and 2-methylsulfonyl benzene sulfonyl chloride according to Scheme 11. (2.3 g, 47%), $^1$H NMR (500 MHz, CHLOROFORM-d) δ ppm 8.39 (2H, ddd, 12.2, 7.5, 1.5 Hz), 7.84 (2H, m), 5.06 (1H, quin, 5.1 Hz), 3.68 (4H, t, 4.9 Hz), 3.48-3.61 (4H, m), 1.43 (9H, s), 1.27 (3H, t, 7.2 Hz), 1.19 (3H, t, 6.9 Hz).

Example 8

HNO Production Via N$_2$O Quantification

Nitrous oxide is produced via the dimerization and dehydration of HNO, and is the most common marker for HNO production (Fukuto, J. M. et al., Chem. Res. Toxicol. 2005, 18, 790-801). HNO, however, can also be partially quenched by oxygen to yield a product that does not produce N$_2$O (see Mincione, F. et al., J. Enzyme Inhibition 1998, 13, 267-284; and Scozzafava, A. et al., J. Med. Chem. 2000, 43, 3677-3687.) Using Angeli's salt (AS) as a benchmark, the relative amounts of N$_2$O released from compounds are examined via gas chromatography (GC) headspace analysis.

The ability of compounds to donate HNO is assessed. Results are provided in Table 3. N$_2$O results are reported relative to Angeli's salt. All decompositions are carried out at 37° C. under argon.

TABLE 3

| Compound | % N$_2$O DI[6] | % N$_2$O pH 7.4[7] | % N$_2$O pH 10.3[8] | % N$_2$O[9] esterase | Decomp. Time[10] |
|---|---|---|---|---|---|
| 1 | 29 | 1 | | | <3 h |
| 2 | 32 | 1 | | | <3 h |
| 3 | 56 | 4 | | | <3 h |
| 4 | 59 | 5 | | | <3 h |
| 5 | 48 | | | | <3 h |
| 6 | | 2 | | | <3 h |
| 7 | | 7 | | | <3 h |
| 8 | | 2 | | | <3 h |
| 9 | 80 | 15 | | | <3 h |
| 10 | 98 | 39 | | | <3 h |
| 11 | 31 | 12 | | | <3 h |
| 12 | 37 | 1 | | | <3 h |
| 13 | 9 | | | | <3 h |
| 14 | 48 | 6 | | | <3 h |
| 15 | | 7 | | | <3 h |
| 18 | | 4 | | | <3 h |
| 19 | | 35 | | | <2 h (20 min) |
| 20 | | 23 | | | <3 h |
| 21 | | 39 | | | <3 h |
| 22 | | 71 | | | <2 h (20 min) |
| 23 | | 56 | 56 | 57 | <3 h (40 min) |
| 24 | | 23 | | | <3 h (30 min) |
| 25 | | 13 | | | <3 h |
| 26 | | 13 | | | <3 h |
| 27 | | 57 | | | <3 h |
| 28 | | 17 | 44 | | <3 h |
| 29 | | 21 | 52 | 83 | <3 h |
| 30 | | 3 | 8 | | <3 h |
| 31 | | 5 | | | <20 h |
| 32 | | 0 | | | >20 h |
| 33 | | 1 | 33 | | <20 h |
| 36 | | 7 | | 67 | <2 h |
| 37 | | 4 | | 85 | <3 h |
| 38 | | 3 | 37 | 73 | <3 h |
| 40 | | 0 | | | <3 h |

[6]Compound incubated in DI water.
[7]Compound incubated in PBS buffer, pH 7.4.
[8]Compound incubated in pH. 10.3 carbonate buffer.
[9]Compound incubated in PBS buffer, pH 7.4 with 2-4 mg added esterase.
[10]Time required for complete decomposition of compound incubated in PBS buffer, pH 7.4 as determined by HPLC; when measured, an approximate half-life is reported in parentheses.

Example 8A

HNO Production Via N$_2$O Quantification

Compounds are tested in the assay described in Example 7, with the following modification. Test compounds are assessed with and also without the addition of Pig Liver Esterase (PLE) at 37° C. for 90 minutes in PBS buffer at pH 7.4. Certain compounds described herein are tested and show detectable levels of HNO. Certain compounds described herein exhibit enhanced HNO production in the presence of PLE. Compound stability is also determined by assessing the half-life of the compounds in PBS at 37° C. at pH 7.4 with and without the addition of PLE according to methods known in the art, e.g., in PCT publication No. PCT/US2007/0067 10.

Example 9

In Vitro Model to Determine Ability of Compounds or Pharmaceutical Compositions to Treat, Prevent and/or Delay Onset and/or Development of a Disease or Condition Cardiovascular Diseases or Conditions In vitro models of cardiovascular disease can also be used to determine the ability of any of the compounds and pharmaceutical compositions described herein to treat, prevent and/or delay the onset and/or the development of a cardiovascular disease or condition in an individual. An exemplary in vitro model of heart disease is described below.

In-vitro models could be utilized to assess vasorelaxation properties of the compounds and pharmaceutical compositions. Isometric tension in isolated rat thoracic aortic ring segment can be measured as described previously by Crawford, J. H. et al., *Blood* 2006, 107, 566-575. Upon sacrifice, aortic ring segments are excised and cleansed of fat and adhering tissue. Vessels are then cut into individual ring segments (2-3 mm in width) and suspended from a force-displacement transducer in a tissue bath. Ring segments are bathed at 37° C. in a bicarbonate-buffered, Krebs-Henseleit (K-H) solution of the following composition (mM): NaCl 118; KCl 4.6; NaHCO3 27.2; KH2PO4 1.2; MgSO4 1.2; CaCl2 1.75; Na2EDTA 0.03; and glucose 11.1 and perfused continuously with 21% O2/5% CO2/74% N2. A passive load of 2 g is applied to all ring segments and maintained at this level throughout the experiments. At the beginning of each experiment, indomethacin-treated ring segments are depolarized with KCl (70 mM) to determine the maximal contractile capacity of the vessel. Rings are then washed extensively and allowed to equilibrate. For subsequent experiments, vessels are submaximally contracted (50% of KCl response) with phenylephrine (PE, $3\times10^{-8}$-$10^{-7}$ M), and L-NMMA, 0.1 mM, is also added to inhibit eNOS and endogenous NO production. After tension development reaches a plateau, compounds or pharmaceutical compositions are added cumulatively to the vessel bath and effects on tension monitored.

In vitro models can be utilized to determine the effects of the compounds and pharmaceutical compositions in changes in developed force and intracellular calcium in heart muscles. Developed force and intracellular calcium can be measured in rat trabeculae from normal or diseased (i.e. rats with congestive heart failure or hypertrophy) as described previously (Gao W. D. et al., *Circ. Res.* 1995, 76:1036-1048). Rats (Sprague-Dawley, 250-300 g) are used in these experiments. The rats are anesthetized with pentobarbital (100 mg/kg) via intra-abdominal injection, the heart exposed by mid-sternotomy, rapidly excised and placed in a dissection dish. The aorta is cannulated and the heart perfused retrograde (~15 mM/min) with dissecting Krebs-Henseleit (H-K) solution equilibrated with 95% O2 and 5% CO2. The dissecting K-H solution is composed of (mM): NaCl 120, NaHCO3 20, KCl 5, MgCl2 1.2, glucose 10, CaCl2 0.5, and 2,3-butanedione monoximine (BDM) 20, pH 7.35-7.45 at room temperature (21-22° C.). Trabeculae from the right ventricle of the heart are dissected and mounted between a force transducer and a motor arm and superfused with normal K-H solution (KCl, 5 mM) at a rate of ~10 ml/min and stimulated at 0.5 Hz. Dimensions of the muscles are measured with a calibration reticule in the ocular of the dissection microscope (×40, resolution ~1 0 μm).

Force is measured using a force transducer system and is expressed in millinewtons per square millimeter of cross-sectional area. Sarcomere length is measured by laser diffraction. Resting sarcomere length is set at 2.20-2.30 μm throughout the experiments.

Intracellular calcium is measured using the free acid form of fura-2 as described in previous studies (Gao et al., 1994; Backx et al., 1995; Gao et al., 1998). Fura-2 potassium salt is microinjected iontophoretically into one cell and allowed to spread throughout the whole muscle (via gap junctions). The tip of the electrode (~0.2 μm in diameter) is filled with fura-2 salt (1 mM) and the remainder of the electrode is filled with 150 mM KCl. After a successful impalement into a superficial cell in non-stimulated muscle, a hyperpolarizing current of 5-10 nA is passed continuously for ~15 min. Fura-2 epifluorescence is measured by exciting at 380 and 340 nm. Fluorescent light is collected at 510 nm by a photomultiplier tube. The output of photomultiplier is collected and digitized. Ryanodine (1.0 μM) is used to enable steady-state activation. After 15 min of exposure to ryanodine, different levels of tetanizations are induced briefly (~4-8 seconds) by stimulating the muscles at 10 Hz at varied extracellular calcium (0.5-20 mM). All experiments are performed at room temperature (20-22° C.).

Diseases or Conditions Implicating Ischemia/Reperfusion

In vitro models can also be used to determine the ability of any of the compounds and pharmaceutical compositions described herein to treat, prevent and/or delay the onset and/or the development of a disease or condition implicating ischemia/reperfusion injury in an individual.

Cancer

Antitumor activities of the compounds described herein can be assessed using in vitro proliferation assays of tumor cells using well-known methods, such as described in Norris A. J. et al. *Intl. J. Cancer* 2008, 122:1905-1910.

Cells of an appropriate cell line, e.g. human breast cancer cell line MCF-7, are seeded in 96-well tissue culture microtiter plates at ~4000 cells per well for an overnight incubation. Serial 10-fold dilutions of test compounds are added, and the cells are incubated for 72 h. The cell viability is determined using the CellTiter-Glo™ Luminescent Cell Viability Assay (Promega; Madison, Wis.). $IC_{50}$ is measured as the concentration of drug required for inhibiting cell growth by 50%.

Example 10

In Vivo and/or Ex Vivo Models to Determine Ability of Compounds and Pharmaceutical Compositions to Treat, Prevent and/or Delay Onset and/or Development of a Disease or Condition Cardiovascular Diseases or Condition In vivo models of cardiovascular disease can also be used to determine the ability of any of the compounds and pharmaceutical compositions described herein to treat, prevent and/or delay the onset and/or the development of a cardiovascular disease or condition in an individual. An exemplary animal model of heart disease is described below.

In vivo cardiovascular effects obtained with a compound or pharmaceutical composition may be assessed in a control (normal) dog. The study is conducted in adult (25 kg) mongrel (male) dogs chronically instrumented for conscious hemodynamic analysis and blood sampling, as previously described (Katori, T. et al., *Circ. Res.* 2005, 96, 234-243.). Micromanometer transducers in the left ventricle provide pressure, while right atrial and descending aortic catheters provide fluid-pressures and sampling conduits. Endocardial sonomicrometers (anteriorposterior, septal-lateral) measure short-axis dimensions, a pneumatic occluder around the inferior vena cave facilitated pre-load manipulations for pressure-relation analysis. Epicardial pacing leads are placed on the right atrium, and another pair is placed on the right ventricle free wall linked to a permanent pacemaker to induce rapid pacing-cardiac failure. After 10 days of recovery, animals are evaluated at baseline sinus rhythm and with atrial pacing (120-160 bpm). Measurements include conscious hemodynamic recordings for cardiac mechanics.

Compounds described herein are administrated to a healthy control dog at the dose of 1-5 μg/kg/min and the resulting cardiovascular data is obtained.

Demonstration that a compound described herein improves cardiac hemodynamics in hearts with congestive failure: After completing protocols under baseline conditions, congestive heart failure is induced by tachypacing (210 bpm×3 weeks, 240 bpm×1 week), as previously described (Katori, T. et al., *Circ. Res.* 2005, 96: 234-243.). Briefly, end-diastolic pressure and dP/dt$_{max}$ are measured weekly to monitor failure progression. When animals demonstrate a rise in EDP more than 2×, and dP/dt$_{max}$ of >50% baseline, they are deemed ready for congestive heart failure studies.

The values for test compounds and pharmaceutical compositions are obtained after 15 min continuous i.v. infusion (2.5 or 1.25 μg/kg/min) in control and heart failure preparations, respectively, both in the absence and in the presence of volume restoration. For comparison, the same hemodynamic measurements are obtained with AS in heart failure preparations.

Diseases or Conditions Implicating Ischemia/Reperfusion

Ex-vivo models of ischemia/reperfusion can also be used to determine the ability of any of the compounds described herein to treat, prevent and/or delay the onset and/or the development of a disease or condition implicating ischemia/reperfusion injury in an individual. An exemplary ex vivo model of ischemia/reperfusion injury is described below.

Male Wistar rats are housed in identical cages and allowed access to tap water and a standard rodent diet ad libitum. Each animal is anesthetized with 1 g/kg urethane i.p. 10 min after heparin (2,500 U, i.m.) treatment. The chest is opened, and the heart is rapidly excised, placed in ice-cold buffer solution and weighed. Isolated rat hearts are attached to a perfusion apparatus and retrogradely perfused with oxygenated buffer solution at 37° C. The hearts are instrumented as previously described in Rastaldo et al., *Am. J. Physiol.* 2001, 280, H2823-H2832, and Paolocci et al., *Am. J. Physiol.* 2000, 279, H1982-H1988. The flow is maintained constant (approximately 9 mL/min/g wet weight) to reach a typical coronary perfusion pressure of 85-90 mmHg. A constant proportion of 10% of the flow rate is applied by means of one of two perfusion pumps (Terumo, Tokyo, Japan) using a 50 mL syringe connected to the aortic cannula. Drug applications are performed by switching from the syringe containing buffer alone to the syringe of the other pump containing the drug (compound or pharmaceutical composition described herein) dissolved in a vehicle at a concentration 10× to the desired final concentration in the heart. A small hole in the left ventricular wall allows drainage of the thebesian flow, and a polyvinyl-chloride balloon is placed into the left ventricle and connected to an electromanometer for recording of left ventricular pressure (LVP). The hearts are electrically paced at 280-300 bpm and kept in a temperature-controlled chamber (37° C.). Coronary perfusion pressure (CPP) and coronary flow are monitored with a second electromanometer and an electromagnetic flow-probe, respectively, both placed along the perfusion line. Left ventricular pressure, coronary flow and coronary perfusion pressure are recorded using a TEAC R-7 1 recorder, digitized at 1000 Hz and analyzed off-line with DataQ-Instruments/CODAS software, which allow quantification of the maximum rate of increase of LVP during systole (dP/dt$_{max}$).

Hearts are perfused with Krebs-Henseleit solution gassed with 95% O2 and 5% CO2 of the following composition: 17.7 mM sodium bicarbonate, 127 mM NaCl, 5.1 mM KCl, 1.5 mM CaCl2, 1.26 mM MgCl2, 11 mM D-glucose, supplemented with 5 μg/mL lidocaine.

The test compound or pharmaceutical compositions are diluted in buffer immediately prior to use. Hearts are allowed to stabilize for 30 min, and baseline parameters are recorded. Typically, coronary flow is adjusted within the first 10 min and kept constant from thereon. After 30 min stabilization, hearts are randomly assigned to one of the treatment groups, and subjected to 30 min global, no-flow ischemia, followed by 30 min of reperfusion (I/R). Pacing of the hearts is stopped at the beginning of the ischemic period and restarted after the third minute of reperfusion.

Hearts in a control group are perfused with a buffer for an additional 29 min after stabilization. Treated hearts are exposed to a test compound or pharmaceutical composition (e.g., 1 M final concentration for about 20 min followed by a 10 min buffer wash-out period).

In all hearts, pacing is suspended at the onset of ischemia and restarted 3 minutes following reperfusion. As isolated heart preparations may deteriorate over time (typically after 2-2.5 hours perfusion), the re-flow duration is limited to 30 minutes in order to minimize the effects produced by crystalloid perfusion on heart performance, and consistently with other reports.

Accessment of ventricular function: To obtain the maximal developed LVP, the volume of the intra-ventricular balloon is adjusted to an end-diastolic LVP of 10 mmHg during the stabilization period, as reported in Paolocci, supra, and Hare et al., *J. Clin. Invest.* 1998, 101, 1424-31. Changes in developed LVP, dP/dt$_{max}$ and the end-diastolic value induced by the IR protocol are continuously monitored. The difference between the end-diastolic LVP (EDLVP) before the end of the ischemic period and during pre-ischemic conditions is used as an index of the extent of contracture development. Maximal recovery of developed LVP and dP/dt$_{max}$ during reperfusion is compared with respective pre-ischemic values.

Assessment of myocardial injury: Enzyme release is a measure of severe myocardial injury that has yet to progress to irreversible cell injury. Samples of coronary effluent (2 mL) are withdrawn with a catheter inserted into the right ventricle via the pulmonary artery. Samples are taken immediately before ischemia and at 3, 6, 10, 20 and 30 min of reperfusion. LDH release is measured as previously described by Bergmeyer et al., *Verlag Chemie* 1974. Data are expressed as cumulative values for the entire reflow period.

To corroborate the data relative to myocardial injury, determined by LDH release, infarct areas are also assessed in a blinded fashion. At the end of the course (30 min reperfusion), each heart is rapidly removed from the perfusion apparatus, and the LV dissected into 2-3 mm circumferential slices. Following 15 min of incubation at 37° C. in 0.1% solution of nitro blue tetrazolium in phosphate buffer as described in Ma et al., *Proc. Natl. Acad. Sci.* 1999, 96, 14617-14622, unstained necrotic tissue is separated from the stained viable tissue. The areas of viable and necrotic tissue are carefully separated by an independent observer who is not aware of the origin of the hearts. The weight of the necrotic and non-necrotic tissues is then determined and the necrotic mass expressed as a percentage of total left ventricular mass.

Data may be subjected to statistical methods such as ANOVA followed by the Bonferroni correction for post hoc t tests.

Cancer

Anticancer activities of compounds described herein can be assessed using in vivo mouse xenograft models using methods described in Norris A. J. et al., *Intl. J. Cancer* 2008, 122, 1905-1910 and Stoyanovsky, D. A. et al., *J. Med. Chem.* 2004, 47, 210-217).

Mice are inoculated with appropriate tumor cells by subcutaneous injection into the lower flank. Therapy can be started after 1-3 weeks when the tumors have reached an average volume of ~50-60 mm³. Tumor diameters are measured with digital calipers, and the tumor volume is calculated. The anti-tumor efficacy of test compounds is assessed by comparison of tumor size in test group to that in the control group.

Example 11

In Vivo Animal Studies (Acute Treatment, Intravenous Infusion)

This example demonstrates the efficacy of compounds and pharmaceutical compositions described herein to lower pulmonary artery pressure in rats with monocrotaline-induced PH.

Rats (250-250 g) are anesthetized via an intra-muscular (i.m.) injection of ketamine/xylazine (80/10 mg/kg). A half dose (40 mg/kg ketamine/5 mg/kg xylazine) is given as supplemental anesthesia as needed. Animals are placed on a heating pad set to maintain body temperature at approximately 37° C. Body temperature is monitored throughout the experiment. Once consciousness is lost, a pressure transducer is inserted into a femoral artery to measure arterial blood pressure. A fluid filled catheter is inserted through the right jugular vein into the pulmonary artery to measure pulmonary artery pressure via a pressure transducer. A cannula is placed into the left jugular vein for dosing.

Figure 2:
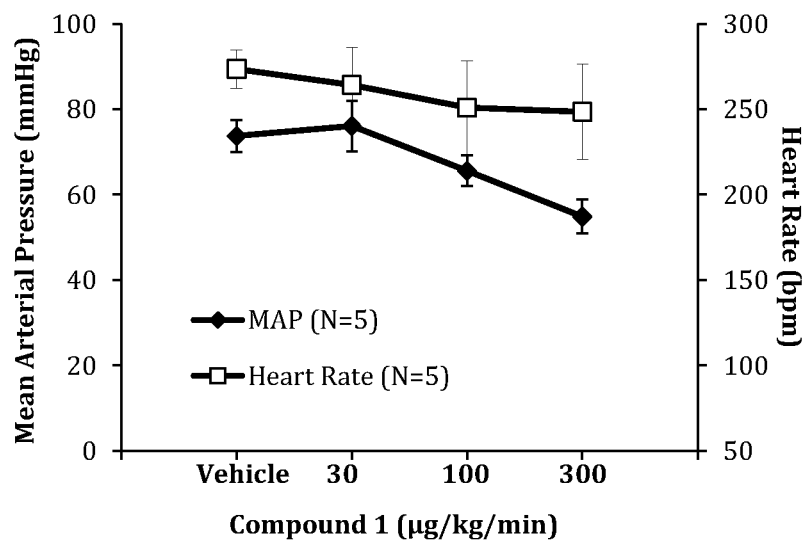
FIG. 2 shows the intravenous effects of a nitroxyl (HNO) donor on mean arterial pressure (MPAP) and heart rate in rats.
Figure 3:
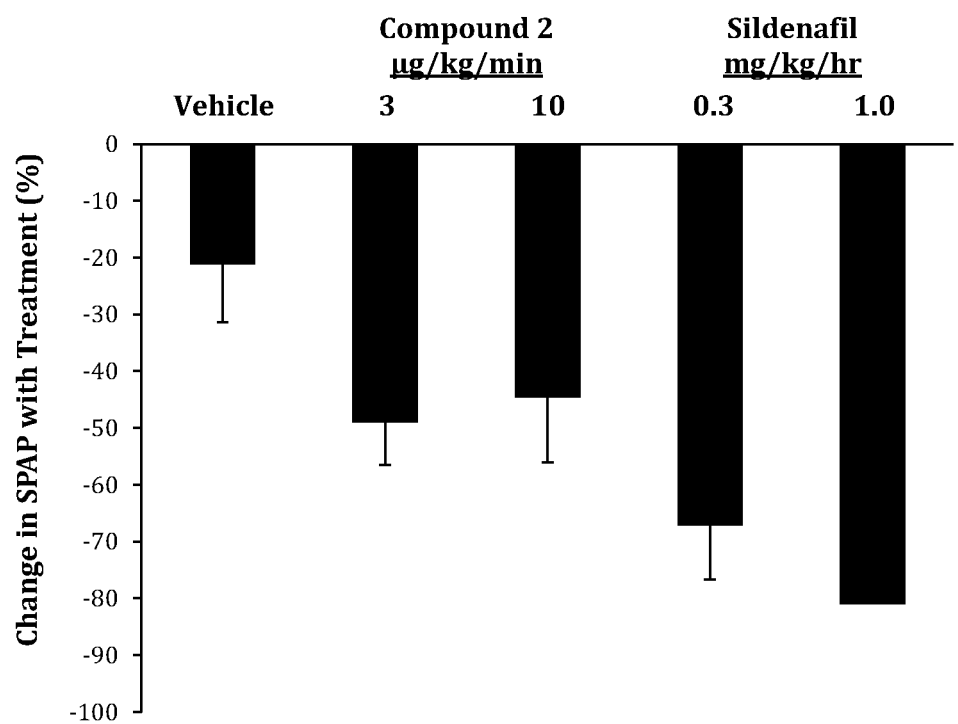
FIG. 3 shows the intravenous effects of a nitroxyl (HNO) donor on mean change in systolic pulmonary arterial pressure (SPAP) during hypoxic period relative to normoxic period compared to sildenafil citrate in dogs.

Monocrotaline is administered via a single subcutaneous injection (60 mg/kg) approximately 3 weeks prior to the terminal procedure. A baseline pulmonary artery pressure of >30 mmHg is required to initiate study of the compounds described herein. A nitroxy donor or a compound or pharmaceutical composition as described herein is administered intravenously in a dose-escalation manner in 20 minute intervals from doses of 10 to 300 µg/kg/min. Hemodynamic indices, including MAP (mean arterial pressure), SAP (systolic arterial pressure), DAP (diastolic arterial pressure), HP (heart rate), MPAP (mean pulmonary arterial pressure), SPAP (systolic arterial pressure), DPAP (diastolic pulmonary arterial pressure), are measured. The results of test compounds are illustrated in FIG. 1, FIG. 2 and FIG. 3.

For the terminal procedure, after surgical instrumentation and an approximate 10 minute pre-dose equilibration period, test compound or pharmaceutical composition solutions are infused via jugular vein catheter. At the end of the experiment, rats are euthanized under anesthesia via pentobarbital overdose.

Example 12

In Vivo Animal Studies (Acute Treatment, Intravenous Infusion or Inhaled Administration)

This example demonstrates the efficacy of the compounds and pharmaceutical compositions described herein to lower pulmonary artery pressure in dogs with hypoxia-induced PH.

Healthy dogs (10-15 kg) are anesthetized with pentobarbital (20-40 mg/kg. intravenously) and anesthesia is maintained by continuous infusion of pentobarbital at rate of 5-10 mg/kg/h. Dogs are intubated via a tracheotomy, and artificially respired (while monitoring inspired oxygen and expired $CO_2$). The left femoral vein and artery are cannulated for dose administration and arterial blood pressure recording. The right jugular vein is cannulated with a pulmonary artery pressure catheter (Swan Ganz catheter), to measure both pulmonary arterial pressure (PAP) and pulmonary wedge pressure (PWP). This catheter is also used for measurement of cardiac output via thermodilution techniques following rapid injection of cold 5 mL saline. Electrocardiograms are monitored throughout the experiment.

During the baseline and control measurements inspired oxygen is maintained at 40%. Hypoxia is induced by adding nitrogen to the respiratory gas at a rate sufficient to reduce respired oxygen to 10% (FiO2=10%). Each hypoxic condition is maintained for 15-30 minutes and then normoxic (FiO2=40%) control condition is returned. Each dose of test compound or pharmaceutical composition is intravenously administered during the 30 minute hypoxic condition; no drug is infused during the subsequent normoxia until the next dose is given. Test compounds or pharmaceutical compositions are given intravenously in the range of 1 to 100 µg/kg/min and various hemodynamic indices are recorded. Alternatively, in this experiment test compounds or pharmaceutical compostions are administered using an inhalation nebulizer at dose levels of 0.1-1 g/kg in 5-10 time period during each hypoxia period.

Example 13

In Vivo Animal Studies (Chronic Treatment, Continuous Intravenous Infusion)

This example demonstrates the efficacy of the compounds and pharmaceutical compositions described herein to retard the progression of disease in rats with monocrotaline-induced PH.

Rats (200-250 g) are surgically implanted with a pressure transducer equipped telemetry transmitter. The transmitter assembly is secured internally; the fluid-filled catheter is placed into the jugular vein with the tip of the pressure transducer positioned in the right ventricle for collection of right ventricular pressure (RVP) data. Additionally, all animals, with the exception of the sham group, are implanted with femoral vein cannulas for the purposes of dosing.

Monocrotaline (MCT) is administered to vehicle-control animals by subcutaneous injection. One week following the MCT injection, the vehicle-control animals are administered saline or a low or high dose of a test compound or pharmaceutical composition by continuous intravenous infusion for two weeks. The test and vehicle control article are administered by external pump. Weekly clinical observations are performed on animals.

For cardiovascular evaluations, RVP data is collected with animals allowed free movement in the home cage. The animals are monitored for at least 24 hours prior to MCT administration. RVP is also monitored at 24 hours following the end of the two week infusion, and occurs for at least 24 hours. All animals are necropsied at the end of the study. Weights of lungs and pulmonary artery, heart and each individual chamber are evaluated. The weights of the heart, LV, RV, and ratio to body weight are reported. The small pulmonary arteries from each animal are evaluated for medial thickness, neointima, and smooth muscle hypertrophy.

Example 14

In Vivo Animal Studies (Chronic Treatment, Oral Administration)

This example demonstrates the efficacy of the compounds and pharmaceutical compositions described herein to retard the progression of disease in rats with monocrotaline-induced PH.

The general methodology for this experiment is similar to that of Example 12 above. One difference is that the route of administration is oral, with a dosing regimen of once to four times daily at dose levels of 0.1-1 g/kg.

Example 15

In Vivo Animal Studies (Chronic Treatment, Continuous Intravenous Infusion)

This example demonstrates the efficacy of the compounds and pharmaceutical compositions described herein to reverse the progression of disease in rats with monocrotaline-induced PH.

In this study, rats (200-250 g) rats are surgically implanted with a pressure transducer equipped telemetry transmitter. The transmitter assembly is secured internally; the fluid-filled catheter is placed into the jugular vein with the tip of the pressure transducer positioned in the right ventricle for collection of right ventricular pressure (RVP) data. Additionally, all animals, with exception of sham group, are implanted with femoral vein cannulas for the purposes of dosing.

The vehicle and control article, monocrotaline (MCT), are administered by subcutaneous injection. Three weeks following the MCT injection, animals are administered saline or a low or high dose of a test compound or pharmaceutical composition by continuous intravenous infusion for three weeks. The test compound or pharmaceutical composition and vehicle control article are administered by external pump. Weekly clinical observations are performed on the animals.

For cardiovascular evaluations, RVP data is collected with animals allowed free movement in the home cage. The animals are monitored for at least 24 hours prior to MCT administration. RVP is also monitored for at least 24 hours following the end of the two week infusion. All animals are necropsied at the end of the study. Weights of lungs and pulmonary artery, heart and each individual chamber are evaluated. The weights of the heart, LV, RV, and ratio to body weight are reported. The small pulmonary arteries from each animal are evaluated for medial thickness, neointima, and smooth muscle hypertrophy.

Example 16

In Vivo Animal Studies (Chronic Treatment, Oral Administration)

This example demonstrates the efficacy of the compounds and pharmaceutical compositions described herein to reverse the progression of disease in rats with monocrotaline-induced PH.

The general methodology is similar to that of Example 14, with the exception that the route of administration is oral, with a dosing regimen of one to four times daily at dose levels of 0.1-1 g/kg.

Example 17

In Vivo Animal Studies (Chronic Treatment, Inhaled Administration)

This example demonstrates the efficacy of the compounds and pharmaceutical compositions described herein to retard progression of disease in rats with monocrotaline-induced PH.

The general methodology is similar to that of Example 12 above, with the exception that the route of administration is via inhalation, with a dosing regimen of one to four times daily at dose levels of 0.1-1 g/kg.

Example 18

In Vivo Animal Studies (Chronic Treatment, Inhaled Administration)

This example demonstrates the efficacy of the compounds and pharmaceutical compositions described herein to reverse the progression of disease in rats with monocrotaline-induced PH.

The general methodology is similar to that of Example 12, with the exception that the route of administration is via inhalation, with a dosing regimen of one to four times daily at dose levels of 0.1-1 g/kg.

Example 19

In Vivo Animal Studies (Acute Treatment, Intravenous Infusion and Inhaled Administration)

This example demonstrates the efficacy of the compounds and pharmaceutical compositions described herein to lower pulmonary artery pressure in dogs with thromboxane-induced PH.

Experimental PH is induced by continuous infusion of a thromboxane A2 receptor agonist analog (for example U46619, Tocris Bioscience). The thromboxane A2 receptor agonist analog infusion rate (0.1-1 mg/kg/min) is adjusted to maintain a systolic pulmonary artery pressure (PAP) at 40 mmHg in anesthetized and mechanically ventilated dogs. The left femoral vein and artery are cannulated for dose administration and arterial blood pressure recording. The right jugular vein is cannulated with a pulmonary artery pressure catheter (Swan Ganz catheter), to measure both pulmonary arterial pressure (PAP) and pulmonary wedge pressure (PWP). This catheter is also used for measurement of cardiac output via thermodilution techniques following rapid injection of cold 5 mL saline. Electrocardiograms are monitored throughout the experiment.

Once a stable steady-state in hemodynamic is achieved, various doses of the test compounds or pharmaceutical compositions are given intravenously at dose rates in the range of 1 to 100 µg/kg/min and various hemodynamic indices are recorded. Alternatively, in this experiment the test compounds or pharmaceutical compositions are administered using an inhalation nebulizer at dose levels of 0.1-1 g/kg in 5-10 time period.

Example 20

In Vivo Human Studies (Acute Treatment, Intravenous Infusion and Inhaled Administration)

This example demonstrates the efficacy of HNO donors to lower pulmonary artery pressure in human subjects with various causes of pulmonary hypertension.

Patients (either gender) with various causes of pulmonary hypertension are selected for this study. Baseline hemodynamic characteristics of the patients are assessed by collected various hemodynamic indices utilizing right heart catheterization (e.g. right atrial pressure, mean pulmonary artery pressure, cardiac index), and blood gas profiling. Cardiac rhythm is monitored using continuous electrocardiography, and arterial pressure is monitored using a pressure cuff. Patients are tested for reversibility of pulmonary hypertension using nitric oxide (NO) by inhalation. Hemodynamic indices are then reassessed. Once all indices have returned to baseline upon cessation of NO delivery, and a baseline is established, various doses of HNO donors are given intravenously at dose rates in the range of 1 to 100 μg/kg/min (either continuous dose or in a dose-escalation fashion) and various hemodynamic indices are recorded. Alternatively, in this experiment HNO donors are administered using an inhalation nebulizer at dose levels of 0.1-1 g/kg in 5-10 minute time period. Hemodynamic indices are assessed at various time points during the infusion period. A few patients receive placebo instead of HNO donor in a double-blind randomized fashion. From the data collected during various periods of the trial, the pulmonary and systemic vascular resistances are calculated.

Example 21

Human Clinical Trials to Determine Ability of Compounds or Pharmaceutical Compositions to Treat, Prevent and/or Delay Onset and/or Development of a Disease or Condition Any of the compounds and pharmaceutical compositions described herein can also be tested in humans to determine the ability of the compounds or pharmaceutical compositions to treat, prevent and/or delay the onset and/or the development of a disease or condition. Standard methods can be used for these clinical trials. In one exemplary method, individuals with a disease or condition described herein, such as congestive heart failure, are enrolled in a tolerability, pharmacokinetics and pharmacodynamics phase I study of a therapy using the compounds described herein in standard protocols. Then a phase II, double-blind randomized controlled trial is performed to determine the efficacy of the compounds using standard protocols.

It will be apparent to those skilled in the art that specific embodiments of the invention may be directed to one, some or all of the above- and below-indicated embodiments in any combination.

While the invention has been described in some detail by way of illustration and example for purposes of clarity of understanding, it should be understood by those skilled in the art that various changes may be made and equivalents may be substituted without departing from the true spirit and scope of the invention. Therefore, the description and examples should not be construed as limiting the scope of the invention.

All references, publications, patents, and patent applications disclosed herein are hereby incorporated by reference in their entirety.

What is claimed is:
1. A compound of formula (I)

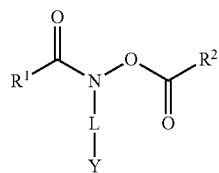

(I)

or a pharmaceutically acceptable salt thereof wherein:

L is a bond, —SO$_2$— or —O—;

Y is alkyl, aryl, heteroaryl or benzyl, wherein said alkyl, aryl, heteroaryl and benzyl are substituted with one or more substituents independently selected from W;

W is halo, —CN, —NO$_2$, —COR$^3$, —COOR$^3$, —CONR$^3$R$^4$, —CH(C(O)R$^3$)$_2$, —SO$_2$R$^3$ or —COX, wherein X is halo, and R$^3$ and R$^4$ are independently alkyl or aryl, or R$^3$ and R$^4$ are taken together to form a cycloalkyl or heterocycloalkyl, wherein said cycloalkyl and heterocycloalkyl are unsubstituted or substituted with one or more substituents;

R$^1$ is hydrogen, alkyl, heterocycloalkyl, aryl, benzyl, alkoxy, aryloxy, benzyloxy, —NR$^5$R$^6$, —N(OR$^5$)R$^6$, —NR$^5$C(O)R$^6$ or —O-heterocycloalkyl, wherein said alkyl, heterocycloalkyl, aryl, benzyl, alkoxy, aryloxy, benzyloxy, —N(OR$^5$)R$^6$, —NR$^5$C(O)R$^6$ and —O— heterocycloalkyl are unsubstituted or substituted with one or more substituents;

R$^2$ is hydrogen, alkyl, heterocycloalkyl, aryl, benzyl, aryloxy, benzyloxy, —NR$^5$R$^6$, —N(OR$^5$)R$^6$, —NR$^5$C(O)R$^6$ or —O-heterocycloalkyl, wherein said alkyl, heterocycloalkyl, aryl, benzyl, aryloxy, benzyloxy, —N(OR$^5$)R$^6$, —NR$^5$C(O)R$^6$ and —O-heterocycloalkyl are unsubstituted or substituted with one or more substituents; and R$^5$ and R$^6$ are independently alkyl or aryl, where said alkyl and aryl are unsubstituted or substituted with one or more substituents;

provided that when L is —SO$_2$—, R$^2$ is phenyl or alkyl, and Y is phenyl substituted with one substituent selected from W, then W is not 4-chloro or 4-nitro; and provided that when L is —SO$_2$—, R$^2$ is alkyl, and Y is phenyl substituted with two or three substituents independently selected from W, then two of the substituents are not 3-nitro and 5-nitro.

2. The compound of claim 1, wherein L is —SO$_2$—.

3. The compound of claim 1, wherein Y is aryl substituted with one or more substituents independently selected from W.

4. The compound of claim 1, wherein Y is aryl substituted with one, two or three substituents independently selected from W.

5. The compound of claim 1, wherein Y is phenyl substituted with one or more substituents independently selected from W.

6. The compound of claim 1, wherein Y is heteroaryl and said heteroaryl is unsubstituted or substituted with one or more substituents independently selected from W.

7. The compound of claim 1, wherein Y is benzyl and said benzyl is substituted with one or more substituents independently selected from W.

8. The compound of claim 1, wherein W is halo, —SO$_2$R$^3$ or —NO$_2$.

9. The compound of claim 1, wherein W is chloro, bromo, fluoro or —NO$_2$.

10. The compound of claim 1, wherein R$^1$ is alkyl, heterocycloalkyl, alkoxy, phenyl or benzyloxy, wherein said alkyl, heterocycloalkyl, alkoxy, phenyl and benzyoxy are unsubstituted or substituted with one or more substituents independently selected from halo, alkyl, nitro, alkylsulfonyl and trihalomethyl; and R$^2$ is alkyl, heterocycloalkyl, phenyl or benzyloxy, wherein said alkyl, heterocycloalkyl, phenyl and benzyoxy are unsubstituted or substituted with one or more substituents independently selected from halo, alkyl, nitro, alkylsulfonyl and trihalomethyl.

11. The compound of claim 1, wherein:
R¹ is alkyl, heterocycloalkyl, alkoxy, phenyl or benzyloxy, wherein said alkyl is unsubstituted or substituted with one or more halos, and said heterocycloalkyl is unsubstituted or substituted with alkyl; and
R² is alkyl or aryl.

12. The compound of claim 1, wherein $R^5$ and $R^6$ are independently $C_1$-$C_6$ alkyl and said alkyl is unsubstituted or substituted with one or more substituents.

13. The compound of claim 1, wherein $R^5$ and $R^6$ are independently $C_1$-$C_6$ alkyl and said alkyl is unsubstituted or substituted with one or more substituents independently selected from alkoxy, heteroaryl and —C(O)OR¹¹.

14. The compound of claim 2, wherein Y is alkyl, wherein said alkyl is substituted with one or more substituents independently selected from W.

15. The compound of claim 2, wherein Y is alkyl, wherein said alkyl is substituted with one or more halos.

16. The compound of claim 12, wherein R¹ is alkyl, heterocycloalkyl, alkoxy, phenyl, benzyl or benzyloxy, wherein said alkyl, heterocycloalkyl, alkoxy, phenyl, benzyl and benzyloxy are unsubstituted or substituted with one or more substituents independently selected from halo, alkyl, nitro, alkylsulfonyl, trihalomethyl, phenyl, —C(O)OR¹¹, —C(O)R¹³, —OC(O)R¹³, —NR¹¹R¹², —NR¹¹C(O)OR¹³ and —OR¹¹; and
R² is alkyl, heterocycloalkyl, phenyl, benzyl or benzyloxy, wherein said alkyl, heterocycloalkyl, phenyl, benzyl and benzyloxy are unsubstituted or substituted with one or more substituents independently selected from halo, alkyl, nitro, alkylsulfonyl, trihalomethyl, phenyl, —C(O)OR¹¹, —C(O)R¹³, —OC(O)R¹³, —NR¹¹R¹², —NR¹¹C(O)OR¹³ and —OR¹¹.

17. The compound of claim 12, wherein:
R¹ is alkyl or alkoxy; and
R² is alkyl or phenyl, wherein said phenyl is unsubstituted or substituted with one or more substituents independently selected from halo, nitro, alkylsulfonyl and trihalomethyl.

18. A compound selected from:
N-(4-bromobenzenesulfonyl)-N-acetyloxy-acetamide,
N-(2-bromobenzenesulfonyl)-N-acetyloxy-acetamide,
N-(2-chlorobenzenesulfonyl)-N-acetyloxy-acetamide,
N-(2-bromo-4,6-difluoro-benzenesulfonyl)-N-acetyloxy-acetamide,
N-(2,6-dibromobenzenesulfonyl)-N-acetyloxy-acetamide,
N-(2,6-dichlorobenzenesulfonyl)-N-acetyloxy-acetamide,
N-(2,6-difluorobenzenesulfonyl)-N-acetyloxy-acetamide,
N-(2-nitrobenzenesulfonyl)-N-acetyloxy-acetamide,
N-(2,6-dichlorobenzenesulfonyl)-N-acetyloxy-benzamide,
N-(2,6-dichlorobenzenesulfonyl)-N-acetyloxy-benzylcarbamate,
N-(2,6-dichlorobenzenesulfonyl)-N-acetyloxy-dichloroacetamide,
N-(2,5-dichlorobenzenesulfonyl)-N-acetyloxy-trimethylacetamide,
N-(2-nitrobenzenesulfonyl)-N-acetyloxy-trimethylacetamide,
N-(2,6-dichlorobenzenesulfonyl)-N-acetyloxy-trimethylacetamide,
N-(2-bromobenzenesulfonyl)-N-acetyloxy-tert-butyl-carbamate,
N-(2,6-dichlorobenzene sulfonyl)-N-acetyloxy-tert-butyl-carbamate,
N-(2,6-dibromobenzenesulfonyl)-N-acetyloxy-tert-butyl-carbamate,
N-(2,6-dichlorobenzene sulfonyl)-N-4-nitrobenzoyloxy)-tert-butyl-carbamate,
tert-butyl (acetyloxy)[(2-bromophenyl)sulfonyl]carbamate,
tert-butyl (acetyloxy){[2-(methylsulfonyl)phenyl]sulfonyl}carbamate,
tert-butyl {[2-(methylsulfonyl)phenyl]sulfonyl}(propanoyloxy)carbamate,
tert-butyl [(2-methylpropanoyl)oxy]{[2-(methylsulfonyl)phenyl]sulfonyl}carbamate,
tert-butyl [(2,2-dimethylpropanoyl)oxy]{[2-(methylsulfonyl)phenyl]sulfonyl}-carbamate,
tert-butyl {[2-(methylsulfonyl)phenyl]sulfonyl}[(phenylcarbonyl)oxy]carbamate,
ethyl(acetyloxy) {[2-(methylsulfonyl)phenyl]sulfonyl}-carbamate,
ethyl(acetyloxy)[(2-bromophenyl)sulfonyl]carbamate,
benzyl(acetyloxy){[2-(methylsulfonyl)phenyl]sulfonyl}carbamate,
benzyl{[2-(methylsulfonyl)phenyl]sulfonyl}(propanoyloxy)carbamate;
N-[(2,2-dimethylpropanoy)oxy]-4-methyl-N-{[2-(methylsulfonyl)phenyl]sulfonyl}-piperazine-1-carboxamide;
N-[(tert-butoxy)carbonyl](2-methanesulfonylbenzene)sulfonamido 2-(acetyloxy)benzoate;
N-[(tert-butoxy)carbonyl]1-benzofuran-2-sulfonamido 2,2-dimethylpropanoate;
N-[(tert-butoxy)carbonyl]1-benzofuran-2-sulfonamido acetate;
N-[(tert-butoxy)carbonyl](2-bromobenzene)sulfonamido benzoate;
N-[(tert-butoxy)carbonyl]3-bromothiophene-2-sulfonamido 2,2-dimethylpropanoate;
N-[(tert-butoxy)carbonyl]3-chlorothiophene-2-sulfonamido 2,2-dimethylpropanoate;
N-[(tert-butoxy)carbonyl](2-bromobenzene)sulfonamido 2-methylpropanoate;
N-[(tert-butoxy)carbonyl](2-bromobenzene)sulfonamido 2,2-dimethylpropanoate;
N-[(tert-butoxy)carbonyl](2-chlorobenzene)sulfonamido 2,2-dimethylpropanoate;
N-[(tert-butoxy)carbonyl][2-chloro-5-(dimethylcarbamoyl)benzene]sulfonamidoacetate;
N-[(tert-butoxy)carbonyl](2-chlorobenzene)sulfonamido 2-methylpropanoate;
N-[(tert-butoxy)carbonyl](2-bromobenzene)sulfonamido 2-phenylacetate;
N-[(tert-butoxy)carbonyl](2-bromobenzene)sulfonamido 2-methyl-2-phenylpropanoate;
N-[(tert-butoxy)carbonyl](2-bromobenzene)sulfonamido 1-phenylcyclopentane-1-carboxylate;
2-N-[(tert-butoxy)carbonyl](2-bromobenzene)sulfonamido 1-tert-butyl pyrrolidine-1,2-dicarboxylate;
N-[(tert-butoxy)carbonyl](2-bromobenzene)sulfonamido 2-[4-(dimethylamino)phenyl]acetate;
N-[(tert-butoxy)carbonyl](2-bromobenzene)sulfonamido 1-acetylpyrrolidine-2-carboxylate;
N-[(tert-butoxy)carbonyl](2-bromobenzene)sulfonamido (2S)-2-phenylpropanoate;
N-[(tert-butoxy)carbonyl](2-bromobenzene)sulfonamido (2R)-2-phenylpropanoate;
N-[(tert-butoxy)carbonyl]-5-chlorothiophene-2-sulfonamido 2-methylpropanoate;

N-[(tert-butoxy)carbonyl]-5-chlorothiophene-2-sulfonamido 2,2-dimethylpropanoate;
N-[(tert-butoxy)carbonyl](3-methanesulfonylbenzene) sulfonamido 2,2-dimethylpropanoate;
N-[(tert-butoxy)carbonyl](3-methanesulfonylbenzene) sulfonamido 2-methylpropanoate;
N-[(tert-butoxy)carbonyl]pyridine-3-sulfonamido 2,2-dimethylpropanoate;
N-[(tert-butoxy)carbonyl]pyridine-3-sulfonamido 2-methylpropanoate;
N-[(tert-butoxy)carbonyl](2-methanesulfonylbenzene) sulfonamido (2S)-2-{[(tert butoxy) carbonyl](methyl)amino}-4-methylpentanoate;
N-[(tert-butoxy)carbonyl](2-methanesulfonylbenzene) sulfonamido (2R)-2-{[(tert-butoxy)carbonyl](methyl)amino}propanoate;
N-[(tert-butoxy)carbonyl](2-methanesulfonylbenzene) sulfonamido (2S)-2-{[(tert-butoxy)carbonyl](methyl)amino}propanoate;
N-[(tert-butoxy)carbonyl](2-methanesulfonylbenzene) sulfonamido 2-{[(tertbutoxy)carbonyl](methyl)amino}acetate;
N-[(tert-butoxy)carbonyl](2-methanesulfonylbenzene) sulfonamido (2S)-2-{[(tert-butoxy)carbonyl](methyl)amino}-3-methylbutanoate;
N-[(tert-butoxy)carbonyl][(4-chlorophenyl)methane]sulfonamido 2,2-dimethylpropanoate;
N-[(benzyloxy)carbonyl](2-methanesulfonylbenzene)sulfonamido 2,2-dimethylpropanoate;
N-[(tert-butoxy)carbonyl](2-methanesulfonylbenzene) sulfonamido N,N-dimethylcarbamate;
N-[(tert-butoxy)carbonyl](2-bromobenzene)sulfonamido N,N-dimethylcarbamate;
N-[(tert-butoxy)carbonyl](2-methanesulfonylbenzene) sulfonamido morpholine-4-carboxylate;
N-[(tert-butoxy)carbonyl](2-methanesulfonylbenzene) sulfonamido 4-acetylpiperazine-1-carboxylate;
tert-butyl N-{[cyclohexyl(methyl)carbamoyl]oxy}-N-[(2-methanesulfonylbenzene)sulfonyl]carbamate;
1-N-[(tert-butoxy)carbonyl](2-methanesulfonylbenzene) sulfonamido 4-tert-butyl piperazine-1,4-dicarboxylate;
N-[(tert-butoxy)carbonyl](2-methanesulfonylbenzene) sulfonamido N-(2-methoxyethyl) carbamate;
N-[(tert-butoxy)carbonyl](2-methanesulfonylbenzene) sulfonamido N,N diethylcarbamate;
N-[(tert-butoxy)carbonyl](2-methanesulfonylbenzene) sulfonamido N-methoxy-N-methylcarbamate;
tert-butyl N-[(2-methanesulfonylbenzene)sulfonyl]-N-{[methyl(pyridin-3-ylmethyl)carbamoyl]oxy}carbamate;
tert-butyl 2-{[2-(tert-butoxy)-2-oxoethyl][({N-[tert-butoxy)carbonyl](2-methanesulfonylbenzene) sulfonamido}oxy)carbonyl]amino}acetate;
4-{[({N-[(tert-butoxy)carbonyl](2-methanesulfonylbenzene) sulfonamido}oxy)-carbonyl]oxy}oxane;
4-{[({N-[(tert-butoxy)carbonyl](2-bromobenzene) sulfonamido}oxy)carbonyl]oxy}oxane;
1-({[(tert-butoxy)carbonyl][(methoxycarbonyl)oxy]amino}sulfonyl)-2-methanesulfonyl benzene;
1-({[(tert-butoxy)carbonyl]({[(2-methoxyethoxy)carbonyl]oxy})amino}sulfonyl)-2-methanesulfonylbenzene;
1-({[(tert-butoxy)carbonyl]({[2-(2-methoxyethoxy)ethoxy]carbonyl}oxy)amino}-sulfonyl)-2-methanesulfonylbenzene;
1-({[tert-butoxy)carbonyl]({[(1,3-diethoxypropan-2-yl)oxy]carbonyl}oxy)amino}-sulfonyl)-2-methanesulfonylbenzene;
tert-butyl(acetyloxy)[(3-bromothiophen-2-yl)sulfolnyl] carbamate;
N-[(tert-butoxy)carbonyl]1-benzofuran-2-sulfonamido 2,2-dimethylpropanoate;
N-[(tert-butoxy)carbonyl]1-benzofuran-2-sulfonamido acetate;
N-[(tert-butoxy)carbonyl]3-bromothiophene-2-sulfonamido 2,2-dimethylpropanoate;
N-[(tert-butoxy)carbonyl]3-chlorothiophene-2-sulfonamido 2,2-dimethylpropanoate;
N-[(tert-butoxy)carbonyl]5-chlorothiophene-2-sulfonamido 2-methylpropanoate;
N-[(tert-butoxy)carbonyl]5-chlorothiophene-2-sulfonamido 2,2-dimethylpropanoate;
N-[(tert-butoxy)carbonyl]pyridine-3-sulfonamido 2,2-dimethylpropanoate;
N-[(tert-butoxy)carbonyl]pyridine-3-sulfonamido 2-methylpropanoate; and
pharmaceutically acceptable salts thereof.

19. A compound of formula (Ia)

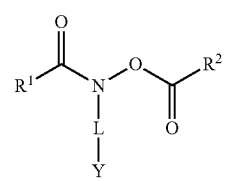

or a pharmaceutically acceptable salt thereof wherein:
L is a bond, —$SO_2$— or —O—;
Y is a heteroaryl, wherein said heteroaryl is unsubstituted or substituted with one or more substituents independently selected from W;
W is halo, —CN, —$NO_2$, —$COR^3$, —$COOR^3$, —$CONR^3R^4$, —$CH(C(O)R^3)_2$, —$SO_2R^3$ or —COX, wherein X is halo, and $R^3$ and $R^4$ are independently alkyl or aryl, or $R^3$ and $R^4$ are taken together to form a cycloalkyl or heterocycloalkyl, wherein said cycloalkyl or heterocycloalkyl are unsubstituted or substituted with one or more substituents;
$R^1$ and $R^2$ are independently hydrogen, alkyl, heterocycloalkyl, aryl, benzyl, alkoxy, aryloxy, benzyloxy or —$NR^5R^6$, wherein said alkyl, heterocycloalkyl, aryl, benzyl, alkoxy, aryloxy, and benzyloxy are unsubstituted or substituted with one or more substituents independently selected from halo, alkyl, nitro, alkylsulfonyl and trihalomethyl; and
$R^5$ and $R^6$ are independently alkyl or aryl.

20. A pharmaceutical composition comprising:
a compound of claim 1; and
a pharmaceutically acceptable excipient.

21. A method of treating a disease or condition selected from cardiovascular diseases, ischemia, reperfusion injury, cancerous disease, pulmonary hypertension and conditions responsive to nitroxyl therapy, comprising administering a compound of claim 1 to a subject in need thereof.

22. The method of claim 21, wherein the disease or condition is a cardiovascular disease.

23. The method of claim 22, wherein the cardiovascular disease is heart failure.

24. The method of claim 23, wherein the heart failure is congestive heart failure.

25. The method of claim 23, wherein the heart failure is acute congestive heart failure.

26. The method of claim 23, wherein the heart failure is acute decompensated heart failure.

27. The method of claim 21, wherein the disease or condition is ischemia or reperfusion injury.

28. The method of claim 21, wherein the disease or condition is a cancerous disease.

29. The method of claim 21, wherein the disease or condition is breast cancer, pancreatic cancer, prostate cancer or colorectal cancer.

30. A method of modulating in vivo nitroxyl levels, comprising administering a compound of claim 1 to a subject in need thereof.

31. A kit comprising:
 a compound of claim 1; and
 instructions for treating a condition that is responsive to nitroxyl therapy.

\* \* \* \* \*

UNITED STATES PATENT AND TRADEMARK OFFICE
CERTIFICATE OF CORRECTION

PATENT NO. : 9,458,127 B2
APPLICATION NO. : 14/667622
DATED : October 4, 2016
INVENTOR(S) : John P. Toscano et al.

It is certified that error appears in the above-identified patent and that said Letters Patent is hereby corrected as shown below:

In the Specification

Column 1, Line 3, immediately after the title, please add the following paragraph:
STATEMENT OF GOVERNMENTAL INTEREST
This invention was made with government support under grant number CHE-0911305, awarded by the National Science Foundation. The government has certain rights in the invention.

Signed and Sealed this
Twentieth Day of February, 2018

Andrei Iancu
*Director of the United States Patent and Trademark Office*